(12) United States Patent
Yamamoto

(10) Patent No.: US 8,952,035 B2
(45) Date of Patent: Feb. 10, 2015

(54) COMBINATION OF ANTI-ANGIOGENIC SUBSTANCE AND ANTI-TUMOR PLATINUM COMPLEX

(75) Inventor: Yuji Yamamoto, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 680 days.

(21) Appl. No.: 12/741,682

(22) PCT Filed: Nov. 7, 2008

(86) PCT No.: PCT/JP2008/070321
§ 371 (c)(1),
(2), (4) Date: May 6, 2010

(87) PCT Pub. No.: WO2009/060945
PCT Pub. Date: May 14, 2009

(65) Prior Publication Data
US 2010/0239688 A1 Sep. 23, 2010

(51) Int. Cl.
*A61K 31/47* (2006.01)
*A61K 33/24* (2006.01)
*C07D 215/48* (2006.01)

(52) U.S. Cl.
CPC .................................. *C07D 215/48* (2013.01)
USPC .......................................... 514/312; 424/649

(58) Field of Classification Search
CPC .............................. A61K 31/47; A61K 33/24
USPC .......................................... 514/312; 424/649
See application file for complete search history.

(56) References Cited

U.S. PATENT DOCUMENTS

| | | | |
|---|---|---|---|
| 4,526,988 A | 7/1985 | Hertel et al. |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,180,818 A | 1/1993 | Cech et al. |
| 5,445,934 A | 8/1995 | Fodor et al. |
| 5,464,826 A | 11/1995 | Grindey et al. |
| 5,487,889 A | 1/1996 | Eckert et al. |
| 5,624,937 A | 4/1997 | Reel et al. |
| 5,650,376 A | 7/1997 | Badaye et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,261,776 B1 | 7/2001 | Pirrung et al. |
| 6,346,398 B1 | 2/2002 | Pavco et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,576,424 B2 | 6/2003 | Fodor et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,253,286 B2 | 8/2007 | Funahashi et al. |
| 7,435,590 B2 | 10/2008 | Komurasaki |
| 7,485,658 B2 | 2/2009 | Bolger et al. |
| 7,495,104 B2 | 2/2009 | Miwa et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,855,290 B2 | 12/2010 | Matsushima et al. |

(Continued)

FOREIGN PATENT DOCUMENTS

| | | |
|---|---|---|
| CN | 1473041 A | 2/2004 |
| CN | 1478078 | 2/2004 |

(Continued)

OTHER PUBLICATIONS

Carlomagno et al., "ZD6474, an Orally Available Inhibitor of KDR Tyrosine Kinase Actvity, Efficiently Blocks Oncogenic RET Kinases", Cancer Research 62:7284-7290 (2002).
US Office Action directed at U.S. Appl. No. 12/301,353 issued on Jan. 24, 2011, 42 pages.
Zhang et al., "Overexpression of Platelet-Derived Growth Factor Receptor a in Endothelial Cells of Hepatocellular Carcinoma Associated with High Metastatic Potential", Clinical Cancer Research 11:8557-8563 (2005).
European Search Report for Appln No. 07806561.2.
Anonymous, Scientific Discussion, Internet Citation, Jan. 1, 2004, p. 1/61-p. 61/61, XP007918143.
Bastin et al., "Salt Selection and Optimisation for Pharmaceutical New Chemical Entities," Organic Process Research and Development, Cambridge, GB, vol. 4, No. 5, Jan. 1, 2000, p. 427-p. 435, XP002228592.

(Continued)

*Primary Examiner* — Raymond Henley, III
(74) *Attorney, Agent, or Firm* — Fish & Richardson P.C.

(57) ABSTRACT

The problems of the present invention are to find a pharmaceutical composition and a method for treating cancer that exhibit excellent anti-tumor effect. Excellent anti-tumor effect is achieved when 4-(3-chloro-4-(cyclopropylaminocarbonyl)aminophenoxy)-7-methoxy- 6 quinolinecarboxamide or an analogous compound thereof, a pharmacologically acceptable salt thereof or a solvate thereof is used in combination with an anti-tumor platinum complex.

6 Claims, 5 Drawing Sheets

(56) References Cited

U.S. PATENT DOCUMENTS

| | | | |
|---|---|---|---|
| 7,973,160 B2 | 7/2011 | Funahashi et al. |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,580,254 B2 | 11/2013 | Adam et al. |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0152759 A1 | 8/2004 | Abrams et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0189629 A1 | 8/2006 | Bolger et al. |
| 2006/0292192 A1 | 12/2006 | Hasenzahl et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2008/0214604 A1 | 9/2008 | Furitsu et al. |
| 2008/0241835 A1 | 10/2008 | Mehraban et al. |
| 2009/0047278 A1 | 2/2009 | Owa et al. |
| 2009/0047365 A1 | 2/2009 | Owa et al. |
| 2009/0053236 A1 | 2/2009 | Yamamoto et al. |
| 2009/0202541 A1 | 8/2009 | Bruns et al. |
| 2009/0247576 A1 | 10/2009 | Kamata et al. |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0118470 A1 | 5/2011 | Funahashi et al. |
| 2011/0158983 A1 | 6/2011 | Bascomb et al. |
| 2011/0293615 A1 | 12/2011 | Yamamoto |
| 2012/0077842 A1 | 3/2012 | Bando |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0296365 A1 | 11/2013 | Bando |

FOREIGN PATENT DOCUMENTS

| | | |
|---|---|---|
| CN | 1890220 A | 1/2007 |
| CN | 101001629 | 7/2007 |
| CN | 101029022 | 9/2007 |
| CN | 101198590 | 6/2008 |
| CN | 101316590 | 12/2008 |
| CN | 101454311 | 6/2009 |
| CN | 101616671 | 12/2009 |
| CN | 102470133 | 5/2012 |
| EP | 0 297 580 | 1/1989 |
| EP | 0405425 | 1/1991 |
| EP | 0602851 | 6/1994 |
| EP | 0684820 | 6/1995 |
| EP | 0795556 | 9/1997 |
| EP | 0837063 | 4/1998 |
| EP | 0870842 | 10/1998 |
| EP | 930305 | 7/1999 |
| EP | 930310 | 7/1999 |
| EP | 3040486 | 3/2000 |
| EP | 3088018 | 7/2000 |
| EP | 1029853 | 8/2000 |
| EP | 1044969 | 10/2000 |
| EP | 543942 | 1/2001 |
| EP | 1153920 | 11/2001 |
| EP | 0712863 | 2/2002 |
| EP | 3420549 | 4/2003 |
| EP | 1331005 A1 | 7/2003 |
| EP | 1382604 | 1/2004 |
| EP | 1411046 | 4/2004 |
| EP | 1415987 | 5/2004 |
| EP | 1447405 | 1/2005 |
| EP | 1 522 540 | 4/2005 |
| EP | 1 535 910 | 6/2005 |
| EP | 1552833 | 7/2005 |
| EP | 1566379 | 8/2005 |
| EP | 1604665 | 12/2005 |
| EP | 1683785 | 7/2006 |
| EP | 1698623 | 9/2006 |
| EP | 1797877 | 6/2007 |
| EP | 1797881 | 6/2007 |
| EP | 1859797 | 11/2007 |
| EP | 1894918 | 3/2008 |
| EP | 1925676 | 5/2008 |
| EP | 1925941 | 5/2008 |
| EP | 1949902 | 7/2008 |
| EP | 1964837 | 9/2008 |
| EP | 2119707 | 11/2009 |
| EP | 2133094 | 12/2009 |
| EP | 2133095 | 12/2009 |
| GB | 2253848 | 9/1992 |
| IN | 236500 | 11/2009 |
| JP | 63-028427 | 2/1988 |
| JP | 01-022874 | 1/1989 |
| JP | 02-291295 | 12/1990 |
| JP | 04-341454 | 11/1992 |
| JP | 06-153952 | 6/1994 |
| JP | 07-176103 | 7/1995 |
| JP | 08-045927 | 2/1996 |
| JP | 08-048078 | 2/1996 |
| JP | 09-023885 | 1/1997 |
| JP | 09-234074 | 9/1997 |
| JP | 11-501343 | 2/1999 |
| JP | 11-143429 | 5/1999 |
| JP | 11-158149 | 6/1999 |
| JP | 11-322596 | 11/1999 |
| JP | 11322596 A | 11/1999 |
| JP | 2000-328080 | 11/2000 |
| JP | 2001-131071 | 5/2001 |
| JP | 2002-003365 | 1/2002 |
| JP | 2002-114710 | 4/2002 |
| JP | 2002-536414 | 10/2002 |
| JP | 2003-012668 | 1/2003 |
| JP | 2003-026576 | 1/2003 |
| JP | 2003-525595 | 9/2003 |
| JP | 2004-513964 | 5/2004 |
| JP | 2004-155773 | 6/2004 |
| JP | 2004-531549 | 10/2004 |
| JP | 2005-501074 | 1/2005 |

(56) References Cited

FOREIGN PATENT DOCUMENTS

| | | |
|---|---|---|
| JP | 2005-504111 | 2/2005 |
| JP | 2005-520834 | 7/2005 |
| JP | 3712393 | 8/2005 |
| JP | 2005-272474 | 10/2005 |
| JP | 2006-508981 | 3/2006 |
| JP | 2006-515884 | 6/2006 |
| KR | 10-0589032 | 6/2006 |
| WO | 86/03222 | 6/1986 |
| WO | 92/20642 | 11/1992 |
| WO | WO9409010 A1 | 4/1994 |
| WO | 95/15758 | 6/1995 |
| WO | 95/19774 | 7/1995 |
| WO | 96/09294 | 3/1996 |
| WO | 96/26997 | 9/1996 |
| WO | 96/30347 | 10/1996 |
| WO | 96/33980 | 10/1996 |
| WO | 96/39145 | 12/1996 |
| WO | 96/40142 | 12/1996 |
| WO | 97/03069 | 1/1997 |
| WO | 97/13760 | 4/1997 |
| WO | 97/13771 | 4/1997 |
| WO | 97/17329 | 5/1997 |
| WO | 97/21437 | 6/1997 |
| WO | 97/38984 | 10/1997 |
| WO | 97/48693 | 12/1997 |
| WO | 98/00134 | 1/1998 |
| WO | 98/02434 | 1/1998 |
| WO | 98/02437 | 1/1998 |
| WO | 98/02438 | 1/1998 |
| WO | 98/13350 | 4/1998 |
| WO | 98/14437 | 4/1998 |
| WO | 98/23613 | 6/1998 |
| WO | 98/32436 | 7/1998 |
| WO | 98/35958 | 8/1998 |
| WO | 98/37079 | 8/1998 |
| WO | 98/50346 | 11/1998 |
| WO | 98/52558 | 11/1998 |
| WO | 99/00357 | 1/1999 |
| WO | 99/32106 | 7/1999 |
| WO | 99/32110 | 7/1999 |
| WO | 99/32111 | 7/1999 |
| WO | 99/32436 | 7/1999 |
| WO | 99/35132 | 7/1999 |
| WO | 99/35146 | 7/1999 |
| WO | 99/43654 | 9/1999 |
| WO | 99/62890 | 12/1999 |
| WO | 00/31048 | 6/2000 |
| WO | 00/42012 | 7/2000 |
| WO | 00/43366 | 7/2000 |
| WO | 00/43384 | 7/2000 |
| WO | 00/44728 | 8/2000 |
| WO | 00/47212 | 8/2000 |
| WO | 00/50405 | 8/2000 |
| WO | 00/71097 | 11/2000 |
| WO | 01/02369 | 1/2001 |
| WO | 01/23375 | 4/2001 |
| WO | 01/27081 | 4/2001 |
| WO | 01/32926 | 5/2001 |
| WO | 01/36403 | 5/2001 |
| WO | 01/40217 | 6/2001 |
| WO | 01/45689 | 6/2001 |
| WO | 01/47890 | 7/2001 |
| WO | 01/47931 | 7/2001 |
| WO | 01/60814 | 8/2001 |
| WO | 02/16348 | 2/2002 |
| WO | WO 02/32872 | 4/2002 |
| WO | 02/41882 | 5/2002 |
| WO | WO 02/36117 | 5/2002 |
| WO | WO 02/44156 | 6/2002 |
| WO | 02/072578 | 9/2002 |
| WO | 02/080975 | 10/2002 |
| WO | 02/088110 | 11/2002 |
| WO | 02/092091 | 11/2002 |
| WO | 03/006462 | 1/2003 |
| WO | 03/013529 | 2/2003 |
| WO | 03/024386 | 3/2003 |
| WO | 03/027102 | 4/2003 |
| WO | 03/028711 | 4/2003 |
| WO | 03/033472 | 4/2003 |
| WO | 03/050090 | 6/2003 |
| WO | 03/074045 | 9/2003 |
| WO | 03/079020 | 9/2003 |
| WO | 2004/006862 | 1/2004 |
| WO | 2004/020434 | 3/2004 |
| WO | 2004/032872 | 4/2004 |
| WO | 2004/032937 | 4/2004 |
| WO | 2004/035052 | 4/2004 |
| WO | 2004/039782 | 5/2004 |
| WO | 2004/041308 | 5/2004 |
| WO | 2004/043472 | 5/2004 |
| WO | 2004/045523 | 6/2004 |
| WO | 2004/064730 | 8/2004 |
| WO | 2004/078144 | 9/2004 |
| WO | 2004/080462 | 9/2004 |
| WO | 2004/080966 | 9/2004 |
| WO | 2004/101526 | 11/2004 |
| WO | 2005/004870 | 1/2005 |
| WO | 2005/021537 | 3/2005 |
| WO | 2005/027972 | 3/2005 |
| WO | 2005/030140 | 4/2005 |
| WO | 2005/044788 | 5/2005 |
| WO | 2005/051366 | 6/2005 |
| WO | 2005/056764 | 6/2005 |
| WO | WO 2005-063713 | 7/2005 |
| WO | 2005/082854 | 9/2005 |
| WO | 2005/092896 | 10/2005 |
| WO | 2005/117887 | 12/2005 |
| WO | 2006/030826 | 3/2006 |
| WO | 2006/030941 | 3/2006 |
| WO | 2006/030947 | 3/2006 |
| WO | 2006/062984 | 6/2006 |
| WO | 2006/090930 | 8/2006 |
| WO | WO 2006/090931 | 8/2006 |
| WO | 2006/036941 | 12/2006 |
| WO | 2006/137474 | 12/2006 |
| WO | 2007/000347 | 1/2007 |
| WO | 2007/014335 | 2/2007 |
| WO | 2007/015569 | 2/2007 |
| WO | 2007/015578 | 2/2007 |
| WO | 2007/023768 | 3/2007 |
| WO | 2007/040565 | 4/2007 |
| WO | 2007/052849 | 5/2007 |
| WO | 2007/052850 | 5/2007 |
| WO | 2007/061127 | 5/2007 |
| WO | 2007/061130 | 5/2007 |
| WO | 2007/136103 | 11/2007 |
| WO | 2008/023698 | 2/2008 |
| WO | WO2008026748 A1 | 3/2008 |
| WO | 2008/088088 | 7/2008 |
| WO | 2008/093855 | 8/2008 |
| WO | 2009/060945 | 5/2009 |
| WO | 2009/077874 | 6/2009 |
| WO | 2009/096377 | 8/2009 |
| WO | WO2009140549 A1 | 11/2009 |

OTHER PUBLICATIONS

Berge et al., Journal of Pharmaceutical Sciences, American Pharmaceutical Association, Washington, US, vol. 66, No. 1, Jan. 1, 1977, p. 1-p. 19, XP002550655.
Gould et al., International Journal of Pharmaceutics, Elsevier, BV, NL, vol. 33, No. 1-3, Nov. 1, 1986, p. 201-p. 217, XP025813036.
Morris et al., "An integrated approach to the selection of optimal salt form for a new drug candidate," International Journal of Pharmaceutics, Elsevier, BV, NL, vol. 105, No. 3, May 9, 1994, p. 209-p. 217, XP023724810.
Ocqueteau et al., "Expression of the CD117 Antigen (C-Kit) on Normal and Myelomatous Plasma cells", British Journal of Haematology, 95:489-493 (1996).
Paz and Zhu, "Development of Angiogenesis Inhibitors to Vascular Endothelial Growth Factor Receptor 2. Current Status and Future Perspectiv", Frontiers in Bioscience 10:1415-1439 (2005).
Pritzker, "Cancer Biomarkers: Easier Said Than Done", Clinical Chemistry 48(8):1147-1150 (2002).

(56) References Cited

OTHER PUBLICATIONS

Raimondo et al., "Angiogenic factors in multiple myeloma: higher levels in bone marrow than in peripheral blood", Haematologica, 85:800-805 (2000).
Tong et al., "Vascular Normalization by Vascular Endothelial Growth Factor Receptor 2 Blockade Induces a Pressure Gradient Across the Vasculature and Improves Drug Penetration in Tumors", Cancer Research 64:3731-3736 (2004).
US Office Action directed at U.S. Appl. No. 11/997,543 issued May 19, 2011.
US Office Action directed at U.S. Appl. No. 12/094,492 issued on Mar. 24, 2011.
US Office Action directed at U.S. Appl. No. 12/864,817 issued on May 19, 2011.
Zhu et al., Molecular Targets for Therapy (MTT), "Inhibition of human leukemia in an animal . . . activity", Leukemia 17:604-611 (2003).
Chesi et al., "Activated fibroblast growth factor receptor 3 is an oncogene that contributes to tumor progression in mulitple myeloma", Blood 97(3):729-736 (2001).
Search report directed at EP application No. 03791389.4, issued on Jul. 7, 2011, 3 pages.
Yu, Lian, "Amorphous pharmaceutical solids: preparation, characterization and stabilization", Adv. Drug Delivery Reviews, Elsevier, Amsterdam, NL, 48(1):27-42 (2001).
European Search Report for Application No. 04807580.8 dated Apr. 18, 2011 (9 pages).
European Search Report for Application No. 06767145.3 dated May 23, 2011 (7 pages).
Chinese Office Action directed at application No. 200880003336.6, issued on May 24, 2011, 24 pages (with English translation).
Zhou et al., "Correlation Research on VEGF Testing in Primary Gastric Cancer and Clinical Pathology Factor", Journal of Practical Oncology, 20(2):103-105 (2006) with English translation.
Office Action directed at Israel Application No. 205512 issued on Nov. 13, 2011.
Written Opinion of the International Searching Authority for International Application No. PCT/JP2008/070321 issued on Jan. 20, 2009.
International Preliminary Report on Patentability for International Application No. PCT/JP2008/070321 issued on May 11, 2010.
European Search Report for Application No. 10015141.4 dated Sep. 9, 2011.
Ko et al., "Stomach Cancer", Cancer supportive care.com, published online Feb. 2003, pp. 1-4.
Kleespies et al., Tyrosine kinase inhibitors and gemcitabine: New treatment options in pancreatic cancer?, Drug Resistance Updates 9:1-19 (2006).
Okura et al., "Effects of monoclonal anti-c-kit antibody (ACK2) on melanocytes in newborn mice", J. Invest. Dermatol., 105(3): 322-328 (1995).
US Office Action directed at U.S. Appl. No. 12/439,339 issued Nov. 14, 2011.
Final Office Action for U.S. Appl. No. 12/523,495 dated Dec. 27, 2011.
Final Office Action for U.S. Appl. No. 11/997,719 issued on Apr. 6, 2011.
Office Action for U.S. Appl. No. 13/205,325 dated Jan. 12, 2012.
Final Office Action for U.S. Appl. No. 11/997,543 dated Nov. 9, 2011.
Office Action for U.S. Appl. No. 12/524,754 dated Dec. 19, 2011.
US Office Action directed U.S. Appl. No. 12/523,495 issued on Sep. 27, 2011.
Office Action for U.S. Appl. No. 13/205,328 dated Jan. 12, 2012.
Johnson et al., "Paclitaxel Plus Carboplatin in Advanced Non-Small-Cell Lung Cancer: a Phase II Trail", J. Clin. Oncol., 14(7):2054-2060 (1996).
Gatzemeier et al., "Phase III Comparative Study of High-Dose Cisplatin Versus a Combination of Paclitaxel and Cisplatin in Patients With Advanced Non-Small-Cell Lung Cancer", J. Clin. Oncol. 18(19):3390-3399 (2000).
Wozniak et al,., "Randomized Trial Comparing Cisplatin With Cisplatin Plus Vinorelbine in the Treatment of Advanced Non-Small-Cell Lung Cancer: A Southwest Oncology Group Study", J. Clin. Oncol. 16(7):2459-2465 (1998).
Sandler et al., "Phase III Trial of Gemcitabine Plus Cisplatin Versus Cisplatin Alone in Patients With Locally Advanced or Metastatic Non-Small Lung Cancer", J. Clin. Oncol., 18(1):122-130 (2000).
Wang et al., "Phase II study of gemcitabine and carboplatin in patients with advanced non-small-cell lung cancer", Cancer Chemother. Pharmacol., 60(4):601-607 (2007).
Kim et al., "A Phase II Study of Irinotecan Plus Cisplatin for Patients with Advanced Stage IIIb or IV NSCLC Previously Treated with Nonplatinum-Based Chemotherapy", Cancer, 107(4):799-805 (2006).
McCulloch et al., "*Astragalus*-Based Chinese Herbs and Platinum-Based Chemotherapy for Adanced Non-Small-Cell Lung Cancer: Meta-Analysis of Randomized Trials", J. Clin. Oncol. 24(3):419-430 (2006).
Ohe et al., Randominzed phase III study of cisplatin plus irinotecan . . . non-small cell lung cancer: Four-Arm Cooperative Study in Japan, Annals of Oncol. 18(2):317-323 (2006).
Tan et al., "Randomized study of vinorelbine-gemcitabine versus vinorelbine-carboplatin in patients with advanced non-small-cell lung cancer", Lung Cancer, Elsevier, 49(2):233-240 (2005).
Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts", American J. of Pathol. 165(1): 35-52 (2004).
Asuno-Shinyaku, "The New Drugs of Tomorrow", Update Summary Dec. 2006 with English translation (14 pages).
Agarwal et al., "Binding of Discoidin Domain Receptor 2 to Collagen I: An Atomic Force Microscopy Investigation", Biochemistry 41:11091-11098 (2002).
Shimizu et al., "Orally active anti-proliferation agents: novel diphenylamine derivatives as FGF-R2 autophosphorylation inhibitors", Bioorganic & Medicinal Chem. Letters 14:875-879 (2004).
Plowright et al., "Ectopic expression of fibroblast growth factor receptor 3 promotes myeloma cell proliferation and prevents apoptosis" Neoplasia, Blood, 95(3): 992-998 (2000).
Heinrich et al., "Inhibition of c-kit receptor tyrosine kinase activity by STI 571, a selective tyrosine inhibitor", Hematopoeisis, Blood 96(3):925-932 (2000).
Trudel et al., "Inhibition of fibroblast growth factor receptor 3 induces differentiation and apoptosis in t(4;14) myeloma", Neoplasia, Blood, 103(9): 3521-3528 (2004).
Trudel et al., "CHIR-258, a novel, multitargeted tyrosine kinase inhibitor for the potential treatment of t(4;14) multiple myeloma", Neoplasia, Blood 105(7):2941-2948 (2005).
Paterson et al., "Preclinical studies of fibroblast growth factor receptor 3 as a therapeutic target in multiple myeloma", Blackwell Publishing Ltd, British Journal of Haematology, 124: 595-603 (2004).
Salmon et al., "Anti-Angiogenic Treatment of Gastrointestinal Malignancies", New Drugs, Cancer Investigation 23:712-726 (2005).
Baker et al., "Blockade of Vascular Endothelial Growth Factor Receptor and Epidermal Growth Factor Receptor Signaling for Therapy of Metastatic Human Pancreatic Cancer", Cancer Research 62: 1996-2003 (2002).
Itoh et al., "Preferential Alternative Splicing in Cancer Generates a K-sam Messenger RNA with Higher Transforming Activity", Cancer Research 54: 3237-3241(2002).
Ueda et al., "Deletion of the Carboxyl-Terminal Exons of K-sam/FGFR2 by Short omologymediated Recombination, Generating Preferential Expression of Specific Messenger RNAs", Cancer Research, 59:6080-6086 (1999).
Lin et al., "The Vascular Endothelias Growth Factor Receptor Tyrosine Kinase Inhibitor PTK787/ZK222584 Inhibits Growth and Migration of Mutiple Myeloma Cells in the Bone Marrow Microenvironment", Cancer Research, 62:5019-5026 (2002).

(56) References Cited

OTHER PUBLICATIONS

Lesueur et al., "Polymorphisms in RET and Its Coreceptors and Ligands as Genetic Modifiers of Multiple Endocrine Neoplasia Type 2A", Cancer Research 66(2):1177-1180 (2006).
Yanagihara et al., "Development and biological analysis of peritoneal metastasis mouse models for human scirrhous stomach cancer", Cancer Sci, 96(6):323-332 (2005).
Shiang et al., "Mutations in the Transmembrane Domain of FGFR3 Cause the Most Common Genetic Form of Dwarfism, Achondroplasia", Cell 78:335-342 (1994).
Vogel et al., "Sensing extracellular matrix: An update on discoidin domain receptor function", Cellular Signalling 18:1108-1116 (2006).
Hattori et al., "Immunohistochemical Detection of K-sam Protein in Stomach Cancer", Clinical Cancer Research, 2:1373-1381 (1996).
Zieger et al., "Role of Activating Fibroblast Growth Factor Receptor 3 Mutations in the Development of Bladder Tumors", Clin Cancer Res 11(21):7709-7719 (2005).
Van Oers et al., "A Simple and Fast Method for the Simultaneous Detection of Nine Fibroblast Growth Factor Receptor 3Mutations in Bladder Cancer and Voided Urine", Clin Cancer Res 11(21):7743-7748 (2005).
Santoro et al., "Minireview: RET: Normal and Abnormal Functions", Endocrinology 145(12):5448-5451 (2004).
Jung et al., "Effects of combination anti-vascular endothelial growth factor receptor and anti-epidermal growth factor receptor therapies on the growth of gastric cancer in a nude mouse model", European Journal of Cancer, 38:1133-1140 (2002).
Matsui et al., "146 E7080, a novel multi-targeted tyrosine kinase inhibitor, exhibits anti-angiogenic activity via inhibition of KIT signaling in a small cell lung cancer xenograft model", European Journal of Cancer, Supplement Pergamon, Oxford, GB XP004639590 abstract.
Erber et al., "Combined inhibition ofVEGF- and PDGF-signaling enforces tumor vessel regression by interfering with pericytemediated endothelial cell survival mechanisms", The FASEB Journal published online Dec. 4, 2003 (25 pages).
Haymo et al., "Pericytes in experimental MDA-MB231 tumor angiogenesis", Histochemistry and Cell Biology, 117(6):527-534 (2002).
Logie et al., "Activating mutations of the tyrosine kinase receptor FGFR3 are associated with benign skin tumors in mice and humans", Human Molecular Genetics, 14(9):1153-1160 (2005).
Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer 102:101-108 (2002).
Haller, D., "Chemotherapy for Advanced Pancreatic Cancer", Int. J. Radiation Oncology Biol. Phys., 56(4): Supplement, pp. 16-23 (2003).
Wakaui , "Chemotherapy of scirrhous gastric cancer", JP Journal of Cancer and Chemotherapy, 21(14): 2398-2406 (1994).
Takahashi et al., "A case of inoperable scirrhous gastric cancer that responded remarkably to a combination of TS-1 +paclitaxel and showed complete loss of ascites", JP Journal of Cancer and Chemotherapy, 31(7):1093-1095 (2004).
Werner et al., "Gastric adenocarcinoma: pathormorphology and molecular pathology", J. Cancer Res. Clin. Oncol. 127:207-216 (2001).
Alvares et al., "A Novel Germ-Line Point Mutation in RET Exon 8 (Gly$^{533}$Cys) in a Large Kindred with Familial Medullary Thyroid Carcinoma" The Journal of Clinical Endocrinology & Metabolism 88(11):5438-5443.
Jimenez et al., "Pheochromocytoma and Medullary Thyroid Carcinoma:a New Genotype-Phenotype Correlation of the RET Protooncogene 891 Germline Mutation", The Journal of Clinical Endocrinology & Metabolism 89(8):4142-4145 (2004).
Elisei et al., "Identification of a Novel Point Mutation in the RET Gene (Ala883Thr), Which is Associated with Medullary Thyroid Carcinoma Phenotype Only in Homozygous Condition", The Journal of Clinical Endocrinology & Metabolism 89(11):5823-5827 (2004).
Kim et al., "An Orally Administered Multitarget Tyrosine Kinase Inhibitor, SU11248, Is a Novel Potent Inhibitor of Thyroid Oncogenic RET/Papillary Thyroid Cancer Kinases", The Journal of Clinical Endocrinology & Metabolism 91(10):4070-4075 (2006).
Kelly et al., "Randomized Phase III Trial of Paclitaxel Plus Carboplatin Versus Vinorelbine Plus Cisplatin in the Treatment of Patients With Advanced Non-Small-Cell Lung Cancer: A Southwest Oncology Group Trial", Journal of Clinical Oncology 19(13):3210-3218 (2001).
Heinrich et al., "Inhibition of KIT Tyrosine Kinase Activity: A Novel Molecular Approach to the Treatment of Kit-Positive Malignancies", Journal of Oncology 20(6):1692-1703 (2002).
Ozols et al., "Phase III Trial of Carboplatin and Paclitaxel Compared With Cisplatin and Paclitaxel in Patients With Optimally Resected Stage III Ovarian Cancer: A Gynecologic Oncology Group Study", Journal of Oncology 21(17):3194-3200 (2003).
Morgan et al., "Dynamic Contrast-Enhanced Magnetic Resonance Imaging as a Biomarker for the Pharmacological Response of PTK787/Zk 222584, an Inhibitor of the Vascular Endothelial Growth Factor Receptor Tyrosine Kinases, in Patients With Advanced Colorectal Cancer and Liver Metastases: Results From Two Phase I Studies", Journal of Oncology 21(21):3955-3964 (2003).
Mologni et al., "Inhibition of Ret tyrosine kinase by SU5416", Journal of Mol. Endo., 37:199-212 (2006).
Carlomagno et al., "BAY 43/9006 Inhibition of Oncogenic RET Mutants", Journal of the National Cancer Institute 98(5):326-334 (2006).
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer", Molecular Cancer Therapeutics, 3(9):1041-1048 (2004).
Zhu et al., "Fibroblast growth factor receptor 3 inhibition by short hairpin RNAs leads to apoptosis in multiple myeloma", Mol Cancer Ther 4(5):787-798 (2005).
Yamada et al., "New Technique for Staining", Monthly Medical Technology, (13 pages).
Santoro et al., "Drug Insight: small-molecule inhibitors of protein kinases in the treatment of thyroid cancer", Nature Clinical Practice Endocrinology & Metabolism 2(1):42-52 (2006).
Naski et al., "Graded activation of fibroblast growth factor receptor 3 by mutations causing achondroplasia and thanatophoric dysplasia", Nature Genetics 13:233-237 (1996).
Chesi et al., "Frequent translocation t(4;14)(p16.3;q32.3) in multiple myeloma is associated with increased expression and activating mutations of fibroblast growth factor receptor", Nature Genetics, 316:260-264 (1997).
Capellen et al., "Frequent activating mutations of FGFR3 in human bladder and cervix carcinomas", Nature Genetics, 23:18-20 (1999).
Willett et al., "Direct evidence that the VEGF-specific antibody bevacizumab has antivascular effects in human rectal cancer", Nature Medicine 10(2):145-147 (2004).
Hurwitz et al., "Bevacizumab plus Irinotecan, Fluorouracil, and Leucovorin for Metastatic Colorectal Cancer", The New England Journal of Medicine', 350(23):2335-2342 (2004).
Miller et al., "Paclitaxel plus Bevacizumab versus Paclitaxel Alone for Metastatic Breast Cancer", The New England Journal of Medicine, 357:2666-76 (2007).
Jhiang, S., "The RET proto-oncogene in human cancers", Oncogene 19:5590-5597 (2000).
Chen et al., "FGFR3 as a therapeutic target of the small molecule inhibitor PKC412 in hematopoietic malignancies", Oncogene 24:8259-8267 (2005).
Experimental and Molecular Therapeutices 30, Proceedings of the American Association for Cancer Research, vol. 47 (2006).
Kashuk et al., "Phenotype—genotype correlation in Hirschsprung disease is illuminated by comparative analysis of the RET protein sequence", PNAS 102(25):8949-8954 (2005).
Morikawa et al., Angiogenesis and Pericytes, Putative Positive Function of Pericytes in Angiogenesis, Course of Cellular Biology, 13 pages, with English translation, (2005).

(56) References Cited

OTHER PUBLICATIONS

Benjamin et al., "Selective ablation of immature blood vessels in established human tumors follows vascular endothelial growth factor withdrawal", The J. of Clin. Invest. 103(2):159-165 (1999).
Olaso et al., "DDR2 receptor promotes MMP-2—mediated proliferation and invasion by hepatic stellate cells", The Journal of Clinical Investigation, 108(9):1369-1378 (2001).
Bergers et al., "Benefits of targeting both pericytes and endothelial cells in the tumor vasculature with kinase inhibitors", The Journal of Clinical Investigation 111(9):1287-1295 (2003).
Inoue et al., "Molecular Target Therapy Targeting Angiogenesis Pathways", The Nishinihon J. Urol., 66:425-432 (2004).
Giles, F., "The Vascular Endothelial Growth Factor (VEGF) Signaling Pathway: A Therapeutic Target in Patients with Hematologic Malignancies", The Oncologists 6(suppl5):32-39 (2001).
Hannequin et al., "Novel 4-Anilinoquinazolines with C-7 Basic Side Chains: Design and Structure Activity Relationship of a Series of Potent, Orally Active, VEGF Receptor Tyrosine Kinase Inhibitors", Journal of Medicine Chemistry 45:1300-1312 (2002).
Micke et al., "Characterization of c-kit expression in small cell lung cancer: prognostic and therapeutic implications", Clinical Cancer Res. 9:188-194(2003).
Office Action dated Oct. 30, 2009 for EP Appl. No. 04719054.1.
European Search Report for EP Appl. No. 07743994.
European Search Report for EP Appl. No. 06782407, Jul. 23, 2010.
ISR (PCT/JP2006/315563) dated Sep. 5, 2006.
ISR (PCT/JP2006/315698) dated Oct. 17, 2006.
ISR (PCT/JP2006/322514) dated Jan. 23, 2007.
ISR (PCT/JP2006/323881) dated Jan. 23, 2007.
ISR (PCT/JP2007/060560) dated Sep. 11, 2007.
ISR (PCT/JP2007/063525) dated Sep. 4, 2007.
ISR (PCT/JP2007/067088) dated Nov. 20, 2007.
ISR (PCT/JP2008/051024) dated Apr. 1, 2008.
ISR (PCT/JP2008/051697) dated Mar. 4, 2008.
ISR (PCT/JP2008/070321) dated Jan. 20, 2009.
ISR (PCT/JP2009/051244) dated Mar. 24, 2009.
Wang and Schwabacher, "A Convenient Set of Bidentate Pyridine Ligands for Combinatorial Synthesis", Tetrahedron Lett.40, 1999, p. 4779-p. 4782.
Taguchi et al., "A novel orally active inhibitor of VEGF rector tyrosine kinases KRN951: Antiangiogenic and anti-tumor activity against human solid tumors.", Taguchi E et al., Proceedings of the AACR annual meeting., vol. 45, Mar. 2004, p. 595, XP002536608.
Lev et al., "A Specific Combination of Substrates is Involved in Signal Transduction by the Kit-Encoded Rector", The EMBO Journal,10(3), 1991, p. 647-p. 654.
Li et al., "Abrogation of c-kit/Steel factor-dendent tumorigenesis by kinase defective mutants of the c-kit rector: c-kit kinase defective mutants as candidate tools for cancer gene therapy, Cancer Research vol. 56", Oct. 1, 1996, p. 4343-p. 4346, XP002522473.
Gall-lstok, et al., "Abstract of Acta Chimica Hungarica", Inst. Exp. Med., Hung. Avad. Svi., Budapest, 1983, p. 112(2)-p. 241-7.
Tian, et al., "Activating c-kit Gene Mutations in Human Germ Cell Tumors", American Journal of Pathology, 154(6), 1999, p. 1643-p. 1647.
Okayama, et al., "Activation of Eosinophils with Cytokines Produced by Lung Mast Cells", Int Arch Allergy Immunol.114:(suppl 1), 1997, p. 75-p. 77.
Blume-Jensen, et al., "Activation of the Human c-kit Product by Ligand-Induced Dimerization Mediates Circular Actin Reorganization and Chemotaxis", The EMBO Journal, 10(13), 1991, p. 4121-p. 4128.
Miyazaki et al., Synthesis, Structure and Biological Activity Relationship of . . . PDGF Receptor, AIMECS 03, 5th AFMC International Medicinal Chem. Symposium, Oct. 2003, Kyoto Japan, 1 page.
Longley, et al., "Altered Metabolism of Mast-Cell Growth Factor (c-kit Ligand) in Cutaneous Mastocytosis", The New England Journal of Medicine, 328(18), 1993, p. 1302-p. 1307.

Hayek, et al., "An in Vivo Model for Study of the Angiogenic Effects of Basic Fibroblast Growth Factor", Biochemical and Biophysical Research Communications, 147(2), 1987, p876-p880.
Folkman, et al., "Angiogenesis", The Journal of Biological Chemistry, 267(16), 1992, p. 10931-p. 10934.
Gerald B. Dermer, "Another anniversary for the war on cancer", Bio/Technology, vol. 12, 1994, p. 320.
Deplanque, et al., "Anti-Angiogenic Agents: Clinical Trial Design and Therapies in Development", European Journal of Cancer, 36, 2000, p. 1713-p. 1724.
Wedge et al., "AZD2171: A Highly Potent, Orally Bioavailable, Vascular Endothelial Growth Factor Rector-2 Tyrosine Kinase Inhibitor for the Treatment of Cancer", Cancer Res., vol. 65(10), p. 4389-4400, 2005.
Natali, et al., "Breast Cancer is Associated with Loss of the c-kit Oncogene Product", Int. J. Cancer, 52, 1992, p. 713-p. 717.
Trisha Gura, "Cancer Models Systems for Identifying new drugs are often faulty", Science, vol. 278, Nov. 7, 1997, p. 1041-p. 1042.
Wakeling, et al., ZD1839 (Iressa): An Orally Active Inhibitor of Epidermal Growth Factor Signalling with Potential for Cancer Therapy, Cancer Res.,62:5749-5754 (2002).
Ikeda, et al., "Changes in Phenotype and Proliferative Potential of Human Acute Myeloblastic Leukemia Cells in Culture with Stem Cell Factor", Experimental Hematology, 21, 1993, p1686-p1694.
J. Haleblian, Characterization of Habits and Crystalline Modification of Solids and Their Pharmaceutical Applications, Journal of Pharmaceutical Sciences, 64(8):1269-1288 (1975).
Metcalfe, D,, "Classification and Diagnosis of Mastocytosis: Current Status", J. Invest. Dermatol, 96, 1991, p. 2S-p. 4S.
Folkman, et al., "Clinical Applications of Research on Angiogenesis", The New England Journal of Medicine, 333(26), 1995, p. 1757-p. 1763.
Hines, et al., "Coexpression of the c-kit and Stem Cell Factor Genes in Breast Carcinomas", Cell Growth & Differentiation, 6, 1995, p. 769-p. 779.
Hibi, et al., "Coexpression of the Stem Cell Factor and the c-kit Genes in Small-Cell Lung Cancer", Oncogene, 6, 1991, p. 2291-p. 2296.
R. Ian Freshney, Alan R. Liss, "Culture of Animal Cells, A Manual of Basic Technique", New York, 1983, p. 4.
Jakeman, et al., "Developmental Expression of Binding Sites and Messenger Ribonucleic Acid for Vascular Endothelial Growth Factor Suggests a Role for This Protein in Vasculogenesis and Angiogenesis", Endocrinology, 133(2), 1993, p. 848-p. 859.
Matsui et al., "E7080 (ER-203492-00), a Novel VEGF Rector Tyrosine Kinase Inhibitor-I. Characterization as an Angiogenesis Inhibitor.", Abstract # 51, Aacr, Toronto, Canada, Apr. 5-9, 2003.
Nakamura et al., "E7080 (ER-203492-00), a Novel VEGF Rector Tyrosine Kinase Inhibitor-II. Effects on Growth of Human Tumor Xenografts and Life Span of Mice in Colon 38 Orthotopic Transplantation Model." Abstract # 52, AACR, Toronto, Canada, Apr. 5-9, 2003.
Yamamoto et al., "A Novel Vegf Receptor Tyrosine Kinase Inhibitor-Iii. Significant prolongation of life span in mice transplanted with human ovarian carcinoma based on inhibition of Vegf signaling", Abstract # 50, Aacr, Toronto, Canada, Apr. 5-9, 2003.
Yamamoto et al., "E7080 a novel multitargeted tyrosine kinase inhibitor, has direct anti-tumor activity via inhibition of KIT signaling in small cell lung cancer", Yamamoto et al., Abstract #4636, AACR, Orlando, FL, Mar. 27-31, 2004.
Matsui et al., "E7080, a novel inhibitor that targets multiple kinases, has potent antitumor activities against stem cell factor producing human small cell lung cancer H146, based on angionenesis inhibition", Int. J. Cancer 122:664-671 (2008).
Matsui et al., "E7080, a novel multi-rector Tyrosine Kinase Inhibitor, inhibited in vitro / in vivo VEGF- and SCF-driven angiogenesis Sclc cell line", Matsui et al., Abstract #146, EORTC-NCI-AACR, Geneva, Switzerland, Sep. 28-Oct. 1, 2004.
Yamamoto et al., "E7080, an oral multi-targeted tyrosine kinase inhibitor, has direct anti-tumor efficacy via inhibition of KIT signaling in gastrointestinal stromal tumor (GIST)" Abstract #40358, 97th annual meeting AACR, Washington, DC., Apr. 1-5, 2006.

(56) References Cited

OTHER PUBLICATIONS

Taniguchi, et al., "Effect of c-kit Mutation on Prognosis of Gastrointestinal Stromal Tumors", Cancer Research, 59, 1999, p. 4297-p. 4300.

Nagata, et al., "Elevated Expression of the Proto-Oncogene c-kit in Patients with Mastocytosis", Leukemia, 12, 1998, p. 175-p. 181.

Kay, et al., "Eosinophils and Eosinophil-Associated Cytokines in Allergic Inflammation", Int. Arch. Allergy Immunol. 113, 1997, p. 196-p. 199.

Ikeda, et al., "Expression and Functional Role of the Proto-Oncogene c-kit in Acute Myeloblastic Leukemia Cells", Blood, 78(11), 1991, p. 2962-p. 2968.

Karl Nocka, et al., "Expression of c-kit gene products in known cellular targets of W mutations in normal and W mutant mice-evidence for an impaired c-kit kinase mutant mice", Genes & Development, Cold Spring Harbor Laboratory Press, 3:816-826, (1989).

Cohen, et al., "Expression of Stem Cell Factor and c-kit in Human Neuroblastoma", Blood, 84(10):3465-3472 (1994).

Strohmeyer, et al., "Expression of the hst-1 and c-kit Protoonocogenes in Human Testicular Germ Cell Tumors", Cancer Research, 51, 1991, p. 1811-p. 1816.

Kanakura, et al., "Expression, Function and Activation of the Proto-Oncogene c-kit Product in Human Leukemia Cells", Leukemia and Lymphorma, 10, 1993, p. 35-p. 41.

Bellone, et al., "Growh Stimulation of Colorectal Carcinoma Cells via the c-kit Rector is Inhibited by TGF-β-1", Journal of Cellular Physiology,172, 1997, p. 1-p. 11.

Okayama, et al., "Human Lung Mast Cells are Enriched in the Capacity to Produce Granulocyte-Macrophage Colony-Stimulating Factor in Response to IgE-Dendent Stimulation", Eur, J. Immunol. 28, 1998, p. 708-p. 715.

Furitsu, et al., "Identification of Mutations in the Coding Sequence of the Proto-Oncogene c-kit in a Human Mast Cell Leukemia Cell Line Causing Ligand-Indendent Activation of c-kit Product", J. Clin. Invest. 92, 1993, p. 1736-p. 1744.

Croom, et al., "Imatinib mesylate in the Treatment of Gastrointestinal Stromal Tumours", Drugs, 63(5), 2003, p. 513-p. 522.

Mendel et al., "In Vivo Antitumor Activity of SU11248, a Novel Tyrosine Kinase Inhibitor Targeting Vascular Endothelial Growth Factor and Platelet-derived Growth Factor Rectors: Determination of a Pharmacokinetic/Pharmacodynamic Relationship" Clin. Cancer Res., 9: 327-337, (2003).

Spacey, et al., "Indolocarbazoles, Potent and Selective Inhibitors of Platelet-Derived Growth Factor Rector Autophosphorylation", Biochemical Pharmacology, 55:261-271, (1998).

Ciardiello, et al., "ZD1839 (IRESSA), An EGFR-Selective Tyrosine Kinase Inhibitor, Enhances Taxane Activity in BCL-2 Overexpressing, Multidrug Resistant MCF-7 ADR Human Breast Cancer Cells", Int. J. Cancer, 98:463-469, (2002).

Naruse, et al., "Antitumor Activity of the Selective Epidermal Growth Factor Receptor-Tyrosine Kinase Inhibitor (EGFR-TKI) IRESSA . . . In Vivo", Int. J. Cancer, 98:310-315, (2002).

International Search Report issued for related PCT application PCT/JP01/09221, Jan. 15, 2002.

International Search Report issued for related PCT application PCT/JP2004/003087, Jul. 13, 2004.

Boissan, et al., "c-Kit and c-kit mutations in mastocytosis and other hematological diseasea", J. Leukocyte Biol., 67:135-148, (2000).

Nugiel et al., "Synthesis and Evaluation of Indenopyrazoles as Cyclin-Dependent Kinase Inhibitors. 2. Probing the Indeno Ring Substituent Pattern", Journal of Medical Chemistry, 45(24):5224-5232, (2002).

Tonary, et al., "Lack of Expression of c-Kit in Ovarian Cancers is Associated with Poor Prognosis", Int. J. Cancer (Pred. Oncol) 89, 2000, p. 242-2250.

Longley, et al., "Classes of c-Kit activating mutations: proposed mechanisms of action and implications for disease classification and therapy", Leukemia Res., 25:571-576, (2001).

Metcalf, et al., "Lineage Commitment in the Progeny of Murine Hematopoietic Prrogenitor Cells: Influence of Thrombopoietin and Interleukin 5", Proc. Nat'l Acad. Sci. USA, 95, 1998, p. 6408-p. 6412.

Metcalfe, et al., "Mast Cells", Physiological Reviews, 77(4), 1997, p. 1033-p. 1079.

Golkar, et al., "Mastocytosis", Lancet, 349, 1997, p. 1379-p. 1385.

Lasota, et al., "Mutations in Exons 9 and 13 of KIT Gene Are Rare Events in Gastrointestinal Stromal Tumors", American Journal of Pathology, 157(4), 2000, p. 1091-p. 1095.

"NCBI GenBank Accession No. NM_000222", Feb. 11, 2008.

Cairns et al., "New antiallergic pyrano[3,2g]quinoline-2,8-dicarboxylic acids with potential for the topical treatment of asthma", Cairns et al, Journal of Medicinal Chemistry 8(12), 1985, p. 1832-p. 1842.

Folkman, J., "New Perspective in Clinical Oncology From Angiogenesis Research", Eur J. Cancer. 32A(14), 1996, p. 2534-p. 2539.

Hogaboam, et al."Novel Role of Transmembrane SCF for Mast Cell Activation and Eotaxin Production in Mast Cell-Fibroblast Interactions", The Journal of Immunology, 160, 1998, p. 6166-p. 6171.

Gardner et al., "In Vitro Activity of Sorghum-Selective Fluorophenyl Urea Herbicides", Pesticide Biochemistry and Physiology, 24(3):285-297, (1985).

Sekido, et al., "Preferential Expression of c-kit Protooncogene Transcripts in Small Cell Lung Cancer", Cancer Research, 51, 1991, p. 2416-p. 2418.

"Proceedings of the American Association for Cancer Research", vol. 45, Mar. 2004, p. 1070-p. 1071.

Kolibaba, et al., "Protein Tyrosine Kinases and Cancer", Biochimica et Biophysica Acta, 1333, 1997, p. F217-p. F248.

Matsui et al., "Quantitative analysis of the profile of tumor vessels may be useful as predictive biomarkers for E7080", Abstract #4631, 98th AACR annual meeting, Los Angeles, CA,, Apr. 14-18, 2007.

Berdel, et al, "Recombinant Human Stem Cell Factor Stimulates Growth of a Human Glioblastoma Cell Line Expressing c-kit Protooncogene", Cancer Research, 52, 1992, p. 3498-p. 3502.

"Redefining the Frontiers of Science 94th Annual Meeting", American Association for Cancer Research, 2003, vol. 44, Washington D.C., USA, Jul. 11-14, 2003.

Kitamura, et al., "Regulation of Development, Survival and Neoplastic Growth of Mast Cells through the c-kit Rector", Int Arch Allergy Immunol., 107, 1995, p. 54-p. 56.

Naclerio, et al., "Rhinitis and Inhalant Allergens", JAMA, 278(22), 1997, p. 1842-p. 1848.

Bussolino, et al, "Role of Soluble Mediators in Angiogenesis", Eur. J. Cancer, 32A(14): , 1996, p. 2401-p. 2412.

Clark et al., "Safety and Pharmacokinetics of the Dual Action Raf Kinase and Vascular Endothelial Growth Factor Rector Inhibitor, BAY43-9006, in Patients with Advanced Refractory Solid Tumors ", Clin. Cancer Res. (2005)11:, 2005, p. 5472-p. 5480.

Langley, et al., "Somatic c-KIT Activating Mutation in Urticaria Pigmentosa and Aggressive Mastocytosis: Establishment of Clonality in a Human Mast Cell Neoplasm", Nature Genetics, 12, 1996, p. 312-p. 314.

Furitsu et al., "Stable medicinal compositions of quinolinecarboxamide derivative", Database CAPLUS Chemical Abstracts Service, Columbus, Ohio, US, 2006, XP002520305.

Lukacs, et al., "Stern Cell Factor (c-kit Ligand) Influences Eosinophil Recruitment and Histamine Levels in Allergic Airway Inflammation", The Journal of Immunology, 156, 1996, p. 3945-p. 3951.

Kotva, et al., "Substances with Antineoplastic Activity, LIII. N-(δ-(4-Pyrrolo[2,3-d]Pyrimidinylthio)Valeryl]} Amino Acids and Analogous Derivatives of Di-and Triglycine", Collection Czechoslov. Chem. Commun.38, 1973, p. 1438-p. 1444.

Furuta, et al., "Synthesis and Biological Evaluation of Selective Inhibitors of PDGF Rector Auto Phosphorylation", Pharmaceutical Research Laboratories, Kirin Brewery Co., Ltd. Takasaki, Gunma, Japan.

Abuzar, S. et al., "Synthesis of some new 7-chloro-4-substituted quinolines as potential antiparasitic agents", Eur. J. Med. Chem.,vol. 21,No. 1, 1986, p. 5-p. 8.

(56) References Cited

OTHER PUBLICATIONS

Miyazaki et al., "Synthesis, Structure and Biological Activity Relationship of E7080 and its Derivatives as Novel and Potent Antiangiogenic Protein Tyrosine Kinase Inhibitors Including the VEGF Rectors, FGFR1 Rector and PDGF Rector." Abstract B-15, AIMECS03, Kyoto, Japan, Oct. 14-17, 2003.
Thomas et al., "The Eosinophil and its Role in Asthma", Gen. Pharmac. 27(4), 1996, p. 593-p. 597.
Wang, et al., "The Expression of the Proto-Oncogene C-Kit in the Blast Cells of Acute Myeloblastic Leukemia", Leukemia, 3(10), 1989, p. 699-p. 702.
Meltzer, E.O., "The Pharmacological Basis for the Treatment of Perennial Allergic Rhinitis and Non-Allergic Rhinitis with Topical Corticosteroids", Allergy, 52, 1997, p. 33-p. 40.
Myers, et al., "The Praration and SAR of 4-(Anilino), 4-(Phenoxy), and 4-(Thiophenoxy)-Quinazolines: Inhibitors of p56lck and EGF-R Tyrosine Kinase Activity", Bioorgan. & Med. Chem. Letters, 7, 1997, p. 417-p. 420.
Hamel, et al., "The Road Less Travelled: c-kit and Stem Cell Factor", Journal of Neuro-Oncology, 35, 1997, p. 327-p. 333.
Takano et al., "Thermal recording materials with improved background stability", Database CA(Online) Chemical Abstracts Service, Columbus, Ohio, US, Feb. 20, 1996, XP002443195.
Scheijen et al."Tryosine Kinase Oncogenes in Normal Hematopoiesis and Hematological Disease", Oncogene, 21, 2002, p. 3314-p. 3333.
"Types of Lung Cancer", Cancer care, Inc., Cancer care, Inc., Aug. 13, 2009.
Matsui et al., "VEGFRs inhibitor E7080 inhibits lymph node metastasis of human breast carcinoma, by preventing murine lymphatic endothelial cells from lymphangiogenesis.", Abstract # PD12-8, 18th EORTC-NCI-AACR symposium on "Molecular Targets and Cancer Therapeutics", Prague, Czech rublic, Nov. 7-10, 2006.
Folkman, J., "What is the Evidence That Tumors are Angiogenesis Dendent?", Journal of the National Cancer Institute, 82(1), 1990, p. 4-p. 6.
Takeda et al., "AZD2171 shows potent anti-tumor activity against gastric cancer expressing variant K-SAM/FGFR2", Proceeding of the American Association for Cancer Research, 47:890 (2006) #3785.
CN Office Action directed at application No. 200580026468.7 issued on Jun. 26, 2009, 6 pages.
CN Office Action directed at application No. 200710007097.9 issued on Mar. 6, 2009, 5 pages.
EESR directed at application No. 06832529.9 issued on Jul. 29, 2009, 6 pages.
Office Action directed at application No. 4025700.8 issued on Apr. 10, 2006, 3 pages.
Search Rort directed at application No. 4719054.1 issued on Apr. 17, 2009, 4 pages.
Search Rort directed at application No. 4818213.3 issued on Jul. 30, 2007, 3 pages.
JP Allowance directed at application No. P2005-515330 issued on Apr. 21, 2009, 2 pages.
KR Office Action directed at application No. 10-2006-7013993 issued on Jul. 31, 2007 (with English translation), 9 pages.
US Office Action directed at U.S. Appl. No. 10/577,531 issued on Sep. 23, 2008, 17 pages.
US Office Action directed at U.S. Appl. No. 10/797,903 issued on Aug. 20, 2009, 12 pages.
US Office Action directed at U.S. Appl. No. 10/797,903 issued on Dec. 11, 2007, 12 pages.
US Office Action directed at U.S. Appl. No. 11/347,749 issued on Feb. 9, 2009, 6 pages.
US Office Action directed at U.S. Appl. No. 11/997,719 issued on Sep. 3, 2010, 10 pages.
WO IPRP directed at application No. PCT/JP2004/003087 issued on Feb. 23, 2006, 5 pages.
WO IPRP directed at application No. PCT/JP2006/312487 issued on Jan. 10, 2008, 7 pages.
Bradley et al., "Preparation of Water-soluble Compounds through Salt Formation", The Practice of Medicinal Chemistry, Technomics, pp. 347-349, 355-356 (1999).
Japanese Office Action for Application No. 2005-516605, Jun. 1, 2010 (with partial translation).
Traxler et al., "AEE788: A Dual Family Epidermal Growth Factor Receptor/ErbB2 and Vascular Endothelial Growth Factor Receptor Tyrosine Kinase Inhibitor with Antitumor and Antiangiogenic Activity", Cancer Research 64:4931-4941 (2004).
European Search Report for Application No. 06768437.3 dated Oct. 11, 2010 (10 pages).
Vippagunta et al., "Crystalline solids", Advanced Drug Delivery Reviews 48:3-26 (2001).
Juurikivi et al., "Inhibition of c-kit tyrosine kinase by imatinib mesylate induces apoptosis in mast cells in rheumatoid synovia: a potential approach to the treatment of arthritis", Ann, Rheum. Dis., 64:1126-1131 (2005).
US Office Action directed at U.S. Appl. No. 12/092,539 issued on Jan. 7, 2011, 74 pages.
European Search Report for Application No. 06833681.7 dated Nov. 24, 2010, 15 pages.
Submission of Documents re Claim 3 and Figure 3 for KR App. Ser. No. 10-2009-7005657, filed on Jul. 13, 2012.
Official Letter for AU2008211952 dated Jul. 10, 2012.
Response to the OA issued for U.S. Appl. No. 11/997,543, filed Mar. 22, 2011.
Response to the OA issued for U.S. Appl. No. 11/997,543, filed Aug. 19, 2011.
Response to the OA issued for U.S. Appl. No. 11/997,543, filed Jan. 9, 2012.
Response to the OA issued for U.S. Appl. No. 11/997,719, filed Dec. 23, 2010.
Response to the Final OA issued for U.S. Appl. No. 11/997,719, filed Jul. 6, 2011.
Response to Office Action issued for U.S. Appl. No. 12/092,539, filed Nov. 22, 2010.
Response to Office Action issued for U.S. Appl. No. 12/092,539, filed Mar. 11, 2011.
Response to Final Office Action issued for U.S. Appl. No. 12/092,539, filed Jun. 15, 2011.
Response to Oa issued for U.S. Appl. No. 13/205,328, filed Apr. 11, 2012.
Response to Office Action directed at U.S. Appl. No. 12/301,353, filed Nov. 23, 2010.
Response to the OA for U.S. Appl. No. 12/439,339, filed Aug. 10, 2011.
Response to the OA for U.S. Appl. No. 12/439,339, filed Feb. 7, 2012.
Response to the OA for U.S. Appl. No. 12/523,495, filed Dec. 7, 2011.
Response to the OA for U.S. Appl. No. 12/524,754, filed Dec. 1, 2011.
Response to the OA for U.S. Appl. No. 12/524,754, filed Feb. 17, 2012.
Response to the OA for U.S. Appl. No. 12/864,817, filed Aug. 9, 2011.
Response to the OA of U.S. Appl. No. 12/864,817, filed Dec. 5, 2011.
Response to the OA for U.S. Appl. No. 12/864,817, filed Dec. 22, 2011.
Response to Office Action for AU 2006309551 filed on Mar. 28, 2012.
CN Office Action issued for CN 200880002425.9 on Mar. 7, 2012.
AU Office Action issued for AU 2008211952 on Apr. 3, 2012.
CN Office Action directed at Appl. No. 200780017371.9 mailed on Mar. 7, 2012.
IL Office Action issued for IL 195282 on Feb. 5, 2012.
CN Office Action issued for CN 200880115011.7 on Feb. 20, 2012.
Response to IL OA directed at Appl. No. 205512 filed on Mar. 11, 2012.
Response to IL OA directed at Appl. No. 207089 filed on Mar. 11, 2012.
AU Office Action issued for AU 2008205847 on Apr. 11, 2012.
Office Action issued for U.S. Appl. No. 10/797,903 on Apr. 1, 2010.
Office Action issued for U.S. Appl. No. 10/797,903 on Sep. 1, 2010.

(56) References Cited

OTHER PUBLICATIONS

Office Action (Decision to refuse) issued for EP 04807580.8 on Oct. 25, 2011.
Forbes et al., "Dissolution kinetics and solubilities of p-aminosalicyclic acid and its salts", International Journal of Pharmaceutics, Elsevier Science BV, 126:199-208 (1995).
Ernst Mutschler et al., Arzneimittel-Wlrkungen Lehrbuch Der Pharmakologie und Toxikologie, Wissenschaftliche Verlagsgesellschaft, Stuttgart, Jan. 1, 1999, p. 1-5.
Rudolf Voight et al., Pharmazeutische Technologie Fuer Studium und Beruf,DT. Apotheker-Verl, Stuttgart; DE, Jan. 1, 2000, p. 40-52. XP008143620.
Lennartsson et al., "The Stem Cell Factor Receptor/c-Kit as a Drug Target in Cancer", Current Cancer Drug Targets, 6:561-571 (2006).
N. Turner and R. Grose, "Fibroblast growth factor signalling: form development to cancer", Nature Reviews, Cancer,10:116-129 (2010).
S. Wells and M. Santoro, "Targeting the RET Pathway in Thyroid Cancer", Clinical Cancer Research, 15:7119-7123 (2009).
Giuseppe Di Lorenzo et al., "Targeted Therapy in the Treatment of Metastatic Renal Cell Cancer", Oncology, 77 (Suppl.1):122-131 (2010).
Abby B.-Siegel et al., "Sorafenib: Where Do We Go from Here?" Hepatology, 52:360-369 (2010).
Kanai et al., "Development Status and Future Prospects of Novel Molecular Target Drugs for Hepatocellular Carcinoma", Journal of the Japanese Society of Gastroenterology, 106:1727-1735 (2009).
National Institutes of Health, Food and Drug Administration, National Library of Medicine, http://clinicaltrials.gov/ct2/show/study /NCT01136733, Sep. 27, 2010.
Office Action issued for EP application No. 04818213.3 on Feb. 2, 2012.
Kitteringham et al., "A Simple Method for the Synthesis of Unsymmetrical Ureas", Synthetic Communications, 30 (11):1937-1943 (2000).
Notice of Allowance issued for U.S. Appl. No. 12/986,638 on Mar. 22, 2012.
International Preliminary Examination Report and Patentability and Written Opinion for International Application No. PCT/2010/063804 dated Mar. 22, 2012.
Restriction Requirement issued for U.S. Appl. No. 11/997,543 dated Feb. 23, 2011.
Restriction Requirement issued for U.S. Appl. No. 12/092,539 dated Oct. 29, 2010.
Restriction Requirement issued for U.S. Appl. No. 12/301,353 dated Oct. 29, 2010.
Restriction Requirement issued for U.S. Appl. No. 12/439,339 dated Jul. 29, 2011.
Restriction Requirement issued for U.S. Appl. No. 12/524,754 Nov. 3, 2011.
Restriction Requirement issued for U.S. Appl. No. 13/083,338 Apr. 12, 2012.
Australian Office Action for Application No. AU2006309551 issued on Apr. 28, 2011.
Australian Response to Office Action for Application No. 2006309551 filed on Jan. 27, 2012.
Australian Office Action for Application No. 2006309551 issued on Feb. 2, 2012.
Chinese Office Action for Application No. 200680041355.9 issued on Mar. 5, 2010 with English translation.
Chinese Response to Office Action for Application No. 200680041355.9 filed on Jul. 19, 2010 with English translation.
Chinese Office Action for Application No. 200680041355.9 issued on Aug. 24, 2010 with English translation.
Chinese Response to Office Action for Application No. 200680041355.9 filed on Nov. 8, 2010 with English translation.
Abrams et al., "SU11248 Inhibits KIT and Platelet-derived Growth Factor Receptor Beta in Preclinical Models of Human Small Cell Lung Cancer", Molecular Cancer Therapeutics., 2: 471-478, 2003.
Carter et al., "Inhibition of drug-resistant mutants of ABL, KIT and EGF receptor kinases", Proceedings of the National Academy of Sciences of the United States of America., 102, 11011-11016, 2005.
CN200780032071.8 Office Action issued on Oct. 13, 2010 with English translation.
CN200780032071.8 Response to Office Action filed on Feb. 16, 2011 with English translation.
Corbin et al., "Sensitivity of oncogenic KIT mutants to the kinase inhibitors MLN518 and PD180970", Blood., 104, 3754-3757, 2004.
EP07806561.2 Office Actions issued on Jan. 19 and Feb. 7, 2011.
EP07806561.2 Response to Office Action filed on Aug. 9, 2011.
EP07806561.2 Office Action issued on Dec. 9, 2011.
European Office Action for Application No. 06832529.9 issued on Oct. 15, 2009.
European Response to Office Action for Application No. 06832529.9 filed on Apr. 22, 2010.
European Office Action for Application No. 06832529.9 issued on Sep. 12, 2011.
European Response to Office Action for Application No. 06832529.9 filed on Oct. 4, 2011.
EP Communication under Rule 71(3) EPC for Application No. 06832529.9 issued on Nov. 25, 2011.
Genitourinary Cancers, Prostate Cancer Genitourinary, http://www.merkmanuals.com/professional/print/sec17/ch241/ch241e.html Mar. 16, 2011.
Guo et al., "Expression of gastric cancer-associated MG7 antigen in gastric cancer, precancerous lesions and *H. pylori*-associated gastric diseases", Word J. Gastroenterol, 8(6):1009-1013 (2002).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
IPRP (PCT/JP2007/067088) dated Mar. 3, 2009 with English translation.
Japanese Patent Application No. 2006-230816 (English translation).
Krystal et al., "Indolinone Tyrosine Kinase Inhibitors Block Kit Activation and Growth of Small Cell Lung Cancer Cells", Cancer Research., 61, 3660-3668, 2001.
Leukemias, Hematology and Oncology, http://www.merkmanuals.com/professional/print/sec11/ch142/ch142a.html Mar. 16, 2011.
Nakamura et al., "KRN633: A Selective inhibitor of vascular endothelial growth factor receptor-2 tyrosine kinase that suppresses tumor angiogenesis and growth", Molecular Cancer Therapeutics., 3: 1639-49, 2004.
Pandey et al., "Identification of Orally Active, Potent, and Selective 4-Piperazinylquinazolines as Antagonists of the Platelet-Derived Growth Factor Receptor Tyrosine Kinase Family", Journal of Medicinal Chemistry., 45, 3772-3793, 2002.
PCT/JP2006/322514 International Preliminary Report on Patentability issued on May 7, 2008.
PCT/JP2006/322516 International Search Report issued on Jan. 23, 2007.
PCT/JP2006/322516 International Preliminary Report on Patentability issued on May 7, 2008.
Santoro et al., "Molecular Mechanism of RET Activation in Human Cancer", Ann. N.Y. Acad Sci. 963:116-121 (2002).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Thyroid Cancers, Endocrine and Metabolic Disorders, http://www.merkmanuals.com/professional/print/sec12/ch152/ch152j.html Mar. 16, 2011.
Office Action for U.S. Appl. No. 12/092,539 issued on Oct. 29, 2010.
Final Office Action for U.S. Appl. No. 12/092,539 issued on May 9, 2011.
Advisory Action for U.S. Appl. No. 12/092,539 issued on Jun. 28, 2011.

(56) References Cited

OTHER PUBLICATIONS

Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
Wisniewski et al.,"Characterization of Potent Inhibitors of the Bcr-Abl and the c-Kit Receptor Tyrosine Kinases", Cancer Research., 62, 4244-4255, 2002.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Yigitbasi et al., "Tumor Cell and Endothelial Cell Therapy of Oral Cancer by Dual Tyrosine Kinase Receptor Blockade", Cancer Research, 64, 7977-7984, 2004.
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Sun et al., "Design, synthesis, and evaluations of substituted 3-[(3-or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5-[5-Fluoro-2-oxo-1,2-dihydroindol-(3Z)-ylidenemethyl]-2,4-dimethyl-1$H$-pyrrole-3carboxylic acid . . . Tyrosine Kinase", Journal of Medicinal Chemistry., 46:1116-1119.
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Bankston et al., "A Scaleable synthesis of BAY 43-9006: A Potent Raf Kinase Inhibitor for the Treatment of Cancer", Organic Process Res Dev., 6:777-81 (2002).
Response to the European Search Report for Euroepan Application No. 06782407 filed on Nov. 8, 2010.
Office Action issued for European Search Report for European Application No. 06782407 on Sep. 29, 2011.
Response to the Office Action for European Application No. 06782407 filed on Jan. 23, 2012.
Office Action issued for Japanese Application No. 2007-529565 issued on Dec. 13, 2011 with English translation.
Response to the Office Action issued for Japanese Application No. 2007-529565 filed on Feb. 3, 2012 with English full translation.
Office Action directed at Israel Application No. 207089 issued on Nov. 13, 2011 (with English translation).
Written Opinion of the International Searching Authority directed at PCT/JP2009/051244 issued on Mar. 24, 2009 (with English translation).
International Preliminary Report directed at PCT/JP2009/051244 issued on Aug. 31, 2010 (with English translation).
Sanger et al., "DNA sequencing with chain-terminating inhibitors", Proc. Natl. Acad. Sci. USA 74: 5463 (1977).
Wakui, "Chemotherapy for Scirrhous Gastric Cancer", Japanese Journal of Cancer and Chemotherapy, 21:(14): 2398-2406 (1994) (English translation only).
Takahashi et al., "A Case of Inoperable Scirrhous Gastric Cancer that Responded Remarkably to a Combination . . . Loss of Ascites", Japanese Journal of Cancer and Chemotherapy, 31(7):1093-1095 (2004) (English translation only).
PCT/JP2008/051697 Written Opinion of the International Searching Authority issued on Mar. 4, 2008.
PCT/JP2008/051697 International Preliminary Report on Patentability issued on Aug. 4, 2009.
CN200880003336.6 Response to Office Action filed on Oct. 8, 2011.
Israel 200090 Office Actions issued on Jun. 22, 2010.
Israel 200090 Response to Office Action filed on Oct. 12, 2010.
Office Action issued for EP application No. 07806561.2 on Dec. 9, 2011.
Nishikawa et al., "Cys611Ser mutation in RET proto-oncogene in a kindred with medullary thryroid carcinoma and Hirschsprung's disease", European Journal of Human Genetics, 11,364-368 (2003).
Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Camiti et al., "The RetC62OR Mutation Affects Renal and Enteric Development in a mouse Model of Hirschprung's Disease", American Journal of Pathology, 168, 1262-1275, (2006).
Asai et al., "Mechanism of Ret Activation by a Mutation of Aspartic Acid 631 Identified in Sporadic Pheochromocytoma", Biochemical and Biophysical Research Communications, 255, 587-590 (1999).
Carlomagno et al., "Point Mutation of the RET Proto-Oncogene in the TT Human Medullary Thyroid Carcinoma cell Line", Biochemical and Biophysical Research Communications, 207,1022-1028 (1995).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Miyauchi et al., "Two Germline Missense Mutations of Codons 804 and 806 of the RET proto-oncogene in the Same 15 Allele in a Patient with Multiple Endocrine Neoplasia Type 2B without Codon 915 Mutation", Japanese Journal of D Cancer Research, 90, 1-5, (1999).
Joao et al., "Somatic trinucleotide change encompassing codons 882 and 883 of the RET proto-oncogene in a patient with sporadic medullary thyroid carcinoma", European Journal of Endocrinology, 142, 573-575, (2000).
Kim et al., "RET Oligonucleotide Microarray for the Detection of RET Mutations in Multiple Endocrine Neoplasia Type 2 Syndromes", Clinical Cancer Research, 8,457-463, (2002).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Grieco et al., "PTC is a Novel Rearranged Form of the ret Proto-Oncogene and Is Frequentrly Detected in Vivo in Human Thyroid Papillary Carcinomas", Cell, 60: 557-563 (1990).
Lam et al., "High prevalence of RET proto-oncogene activation (RET/PTC) in papillary thyroid carcinomas", Eur J Endocrinology, 147: 741-745 (2002).
Klugbauer et al., "Detection of a Novel Type of Ret Rearrangement (PTC5) in Thyroid Carcinomas after Chernobyl and Analysis of the Involved RET-fused Gene RFG5", Cancer Research, 58: 198-203 (1998).
Klugbauer and Rabes, "The transcription coactivator HT1 F1 and a related protein are fused to the RET receptor tyrosine kinase in childhood papillary thyroid carcinomas", Oncogene, 18: 4388-4393 (1999).
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Corvi et al., "RET/PCM-1: a novel fusion gene in papillary thyroid carcinoma", Oncogene, 19: 4236-4242 (2000).
Written Opinion of the International Searching Authority for PCT/JP2007/060560 mailed on Sep. 11, 2007 with English translation.
International Preliminary Report of Patentability issued for PCT/JP2007/060560 on Nov. 18, 2008 with English translation.
Australian Office Action directed at Appl. No. 2007252506 issued on Nov. 7, 2011.
Australian Response to Office Action directed at Appl. No. 2007252506 filed on Jan. 4, 2012.

(56) References Cited

OTHER PUBLICATIONS

Australian Office Action directed at Appl. No. 2007252506 issued on Jan. 13, 2012.
Chinese Office Action directed at Appl. No. 200780017371.9 mailed on Oct. 20, 2010 with English translation.
Chinese Response to Office Action directed at Appl. No. 200780017371.9 filed on Feb. 24, 2011 with English translation.
European Response to EESR directed at Appl. No. 07743994.1-2123 filed on Nov. 23, 2010.
Israel Office Action directed at Appl. No. 195282 issued on Jan. 26, 2010 with English translation.
Israel Response (IDS List) to Office Action directed at Appl. No. 195282 filed on May 3, 2010 with English translation.
Israel Appl. No. 195282 IDS List filed on Jul. 1, 2010.
Russian Office Action directed at Appl. No. 2008149948/15(065561) issued on May 24, 2011 with English translation.
Russian Response to Office Action directed at Appl. No. 2008149948/15(065561) filed on Jul. 27, 2011 with English translation.
Russian Decision of Grant directed at Appl. No. 2008149948/15(065561) received on Nov. 9, 2011 with English translation.
US Office Action directed at U.S. Appl. No. 12/301,353 issued on Oct. 29, 2010.
US Response to Office Action directed at U.S. Appl. No. 12/301,353, filed Nov. 23, 2010.
Australian Response to Office Action directed at Appl. No. 2007252506 filed on Mar. 2, 2012.
Response to Office Action directed at Australain Appl. No. 2006309551 filed on Mar. 30, 2012.
US Office Action directed at U.S. Appl. No. 13/083,338 dated Jun. 8, 2012.
US Final Office Action for U.S. Appl. No. 12/439,339 dated Mar. 30, 2012.
Zimmermann et al., "Potent and Selective Inhibitors of the ABL-Kinase:Phenylamino-Pyrimidine (PAP) Derivatives", Bioorganic and Medicinal Chemistry Letters., 7(2):187-192, 1997.
Zimmermann, "Electrical Breakdown, Electropermeabilization and Electrofusion", Rev. Physiol. Biochem. Pharmacol. 105:176-260 (1986).
"Current Protocols in Molecular Biology", John Wiley & Sons Section 11.4-11.13 (1987).
Antibodies: A Laboratory Manual, E. Harlow and D. Lane, ed. Cold Spring Harbor Laboratory (Cold Spring Harbour, NY, 1988).
First Office Action issued on Mar. 6, 2012 for the corresponding JP application, JP2007-542863, and English translation.
Amendment and Argument filed on Apr. 27, 2012 in response to the JP Office Action for JP2007-542863 and English translation.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Decision of Rejection issued on May 29, 2012 for JP No. 2007-542863 with English translation.
Paulus, "Preparation and Biomedical Applications of Bispecific Antibodies", Behring Inst. Mitt. 78: 118-132 (1985).
Waterman, M., "Computer Analysis of Nucleic Acid Sequences", Methods in Enzymology, 164:765-793 (1988).
Wilbur, W.J. and Lipman, D.J., "Rapid similarity searches of nucleic acid and protein data banks", Natl. Acad. Sci, U.S.A. 80:726-730 (1983).
Altschul et al., "Basic Local Alignment Search Tool", J. Mol. Biol. 215:403-410 (1990).
Pearson, "Rapid and Sensitive Sequence Comparison with FASTP and FASTA", Methods in Enzymology 183:63-98 (1990).
Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Classification of Gastric Carcinoma "Igan-Toriatsukai Kiyaku" (Jun. 1999, 13th ed.) and an English translation.

Voluntary Amendment filed on Feb. 17, 2012 for TH patent appl. No. 1201000221 with English translation.
Office Action dated Apr. 11, 2012 for RU patent appl. No. 2012103471 with English translation.
Office Action dated Apr. 27, 2012 for KR patent appl. No. 10-2007-7001347 with English translation.
Office Action dated May 3, 2012 for IN patent appl. No. 383/CHENP/2008.
Examination Report dated May 9, 2012 for PK patent appl. No. 94/2011.
Office Action dated Jun. 5, 2012 for JP patent appl. No. 2009-123432 with English translation.
Response to the OA filed on May 29, 2012 for RU patent appl. No. 2012103471 with English translation.
Examiner's Report dated Sep. 20, 2005 for AU Patent Application No. 2001295986.
Response filed on Apr. 27, 2006 for AU Patent Application No. 2001295986.
Examiner's Report dated May 4, 2006 for AU Patent Application No. 2001295986.
Response filed on Jul. 26, 2006 for AU Patent Application No. 2001295986.
Notice of Acceptance dated Aug. 3, 2006 for AU Patent Application No. 2001295986.
Voluntary Amendment filed on Aug. 30, 2006 for AU Patent Application No. 2006203099.
Examiner's Report dated Feb. 21, 2008 for AU Patent Application No. 2006203099.
Voluntary Amendment filed on Feb. 21, 2007 for AU Patent Application No. 2006203099.
Voluntary Amendment filed on Feb. 27, 2007 for AU Patent Application No. 2006236039.
Examiner's Report dated Mar. 26, 2008 for AU Patent Application No. 2006236039.
Response filed on May 8, 2008 for AU Patent Application No. 2006236039.
Notice of Acceptance dated May 13, 2008 for AU Patent Application No. 2006236039.
Office Action dated Dec. 6, 2007 for CA Patent Application No. 2426461.
Response filed on May 16, 2008 for CA Patent Application No. 2426461.
Office Action dated Nov. 20, 2008 for CA Patent Application No. 2426461.
Response filed on Feb. 23, 2009 for CA Patent Application No. 2426461.
Office Action dated May 8, 2009 for CA Patent Application No. 2426461.
Response filed on Aug. 13, 2009 for CA Patent Application No. 2426461.
Office Action dated Feb. 10, 2010 for CA Patent Application No. 2426461.
Response filed on May 20, 2010 for CA Patent Application No. 2426461.
Voluntary Amendment filed on Aug. 19, 2010 for CA Patent Application No. 2426461.
Notice of Allowance dated Oct. 14, 2010 for CA Patent Application No. 2426461.
Amendment after Allowance filed on Jan. 4, 2011 for CA Patent Application No. 2426461.
Office Letter Confirmation of Amendment After Allowance dated Jan. 11, 2011 for CA Patent Application No. 2426461.
Amendment filed on May 28, 2003 for CN Patent Application No. 01819710.8 with English translation.
Office Action dated May 13, 2005 for CN Patent Application No. 01819710.8 with English translation.
Response filed on Sep. 13, 2005 for CN Patent Application No. 01819710.8 with English translation.
Amendment filed on Sep. 13, 2005 for CN Patent Application No. 01819710.8 with English translation.
Office Action dated Feb. 10, 2006 for CN Patent Application No. 01819710.8 with English translation.

(56) References Cited

OTHER PUBLICATIONS

Response filed on Apr. 11, 2006 for CN Patent Application No. 01819710.8 with English translation.
Amendment filed on Apr. 11, 2006 for CN Patent Application No. 01819710.8 with English translation.
Office Action dated Aug. 11, 2006 for CN Patent Application No. 01819710.8 with English translation.
Response filed on Oct. 9, 2006 for CN Patent Application No. 01819710.8.
Amendment filed on Oct. 9, 2006 for CN Patent Application No. 01819710.8.
Notice of Allowance dated Dec. 15, 2006 for CN Patent Application No. 01819710.8 with.
Office Action dated Jul. 24, 2009 for CN Patent Application No. 200710007096.4.
Office Action dated Mar. 6, 2009 for CN Patent Application No. 200710007097.9.
Response filed on Jul. 2, 2009 for CN Patent Application No. 200710007097.9.
Amendment filed on Jul. 2, 2009 for CN Patent Application No. 200710007097.9.
Office Action dated Sep. 11, 2009 for CN Patent Application No. 200710007097.9 with.
Response filed on Nov. 19, 2009 for CN Patent Application No. 200710007097.9 with English translation.
Amendment filed on Nov. 19, 2009 for CN Patent Application No. 200710007097.9 with English translation.
Office Action dated Dec. 25, 2009 for CN Patent Application No. 200710007097.9 with English translation.
Response filed on Jan. 26, 2010 for CN Patent Application No. 200710007097.9 with English translation.
Amendment filed on Jan. 26, 2010 for CN Patent Application No. 200710007097.9 with English translation.
Office Action dated Apr. 27, 2010 for CN Patent Application No. 200710007097.9 with English translation.
Response filed on Jun. 22, 2010 for CN Patent Application No. 200710007097.9 with English translation.
Amendment filed on Jun. 22, 2010 for CN Patent Application No. 200710007097.9 with English translation.
Voluntary Amendment filed on Aug. 11, 2010 for CN Patent Application No. 200710007097.9 with English translation.
Notice of Allowance dated Oct. 9, 2010 for CN Patent Application No. 200710007097.9 with English translation.
Partial European Search Report for EP Patent Application No. 01976786.2; Apr. 6, 2004.
Supplementary European Search Report for EP Patent Application No. 01976786.2; Jul. 6, 2004.
Invitation to declare maintenance of the application for EP Patent Application No. 01976786.2; Jul. 12, 2004.
Maintenance of the application for EP Patent Application No. 01976786.2; Sep. 6, 2004.
Amendments received before examination for EP Patent Application No. 01976786.2; Sep. 10, 2004.
Communication from the Examining Division for EP Patent Application No. 01976786.2; Aug. 17, 2005.
Brief communication to applicant for EP Patent Application No. 01976786.2; Sep. 9, 2005.
Communication from the Examining Division for EP Patent Application No. 01976786.2; Sep. 19, 2005.
Reply to communication from the Examining Division for EP Patent Application No. 01976786.2; Jan. 25, 2006.
Communication from the Examining Division for EP Patent Application No. 01976786.2; Mar. 21, 2006.
Reply to communication from the Examining Division for EP Patent Application No. 01976786.2; Jul. 19, 2006.
Communication about intention to grant a European patent for EP Patent Application No. 01976786.2; Sep. 4, 2006.
Decision to grant a European patent for EP Patent Application No. 01976786.2; Feb. 1, 2007.
Communication regarding the expiry of opposition period for EP Patent Application No. 01976786.2; Jan. 4, 2008.
European search report for EP Patent Application No. 04025700.8; Jan. 13, 2005.
Communication from the Examining Division for EP Patent Application No. 04025700.8; Apr. 10, 2006.
Reply to communication from the Examining Division for EP Patent Application No. 04025700.8; Sep. 12, 2006.
Communication from the Examining Division for EP Patent Application No. 04025700.8; Oct. 23, 2006.
Reply to communication from the Examining Division for EP Patent Application No. 04025700.8; Jan. 26, 2007.
Reply to communication from the Examining Division for EP Patent Application No. 04025700.8; Feb. 15, 2007.
Communication about intention to grant a European patent for EP Patent Application No. 04025700.8; Oct. 15, 2007.
Request for amendment of the text intended for grant and translation of claims for EP Patent Application No. 04025700.8; Feb. 1, 2008.
Approval of request for amendments for EP Patent Application No. 04025700.8; Mar. 13, 2008.
Decision to grant a European patent for EP Patent Application No. 04025700.8; Jun. 5, 2008.
Communication regarding the expiry of opposition period for EP Patent Application No. 04025700.8; May 7, 2009.
Deficiencies in sequence listing for EP Patent Application No. 06023078.6; Dec. 5, 2006.
Reply to the invitation to remedy deficiencies for EP Patent Application No. 06023078.6; Jan. 11, 2007.
Request for correction of errors in filed documents for EP Patent Application No. 06023078.6; Feb. 13, 2007.
European Search Report for EP Patent Application No. 06023078.6; Mar. 16, 2007.
Information about decision on request for EP Patent Application No. 06023078.6; Mar. 21, 2007.
Invitation to declare maintenance of the application for EP Patent Application No. 06023078.6; May 2, 2007.
Maintenance of the application for EP Patent Application No. 06023078.6; Jun. 19, 2007.
Communication from Examining Division for EP Patent Application No. 06023078.6; Aug. 2, 2007.
Reply to communication from the Examining Division for EP Patent Application No. 06023078.6; Sep. 11, 2007.
Communication from the Examining Division for EP Patent Application No. 06023078.6; Sep. 26, 2007.
Reply to communication from the Examining Division for EP Patent Application No. 06023078.6; Feb. 4, 2008.
Communication about intention to grant a European patent for EP Patent Application No. 06023078.6; Jul. 18, 2008.
Request for amendment of the text intended for grant and translation of claims for EP Patent Application No. 06023078.6; Nov. 5, 2008.
Decision to grant a European patent for EP Patent Application No. 06023078.6; Dec. 4, 2008.
Communication regarding the expiry of opposition period for EP Patent Application No. 06023078.6; Nov. 4, 2009.
"Voluntary Amendment filed on Sep. 10, 2010 for HU Patent Application No. P0302603" with English translation.
"Office Action dated Oct. 16, 2007 for IL Patent Application No. 155447" with English translation.
"Response filed on Dec. 4, 2007 for IL Patent Application No. 155447" with English translation.
"Notice of Allowance dated Dec. 26, 2007 for IL Patent Application No. 155447" with English translation.
"Notice Prior to Examination dated Jun. 29, 2008 for IL Patent Application No. 189677" with English translation.
"Response to Notice Prior to Examination filed on Jan. 11, 2009 for IL Patent Application No. 189677" with English translation.
"Office Action dated Feb. 18, 2009 for IL Patent Application No. 189677" with English translation.
Response filed on May 13, 2009 for IL Patent Application No. 189677 with English translation.
"Notice of Allowance dated Mar. 14, 2010 for IL Patent Application No. 189677" with English translation.

(56) References Cited

OTHER PUBLICATIONS

"Amendment filed on Mar. 7, 2005 for JP Patent Application No. 2002-536056" with English translation.
"Office Action dated Apr. 11, 2005 for JP Patent Application No. 2002-536056" with English translation.
Argument filed on Apr. 19, 2005 for JP Patent Application No. 2002-536056 with English translation.
"Amendment filed on Apr. 19, 2005 for JP Patent Application No. 2002-536056" with English translation.
"Notice of Allowance dated Aug. 2, 2005 for JP Patent Application No. 2002-536056" with English translation.
"Office Action dated Jan. 27, 2009 for JP Patent Application No. 2005-124034" with English translation.
Japanese Patent Application Laid-Open No. H11-158149 with English translation.
"Argument filed on Mar. 23, 2009 for JP Patent Application No. 2005-124034" with English translation.
"Amendment filed on Mar. 23, 2009 for JP Patent Application No. 2005-124034" with English translation.
"Office Action dated Apr. 28, 2009 for JP Patent Application No. 2005-124034" with English translation.
"Argument filed on May 21, 2009 for JP Patent Application No. 2005-124034" with English translation.
"Amendment filed on May 21, 2009 for JP Patent Application No. 2005-124034" with English translation.
"Notice of Allowance dated Jul. 21, 2009 for JP Patent Application No. 2005-124034" with English translation.
"Written Amendment filed on Jun. 16, 2009 for JP Patent Application No. 2009-123432" with English translation.
"Written Statement filed on Jun. 16, 2009 for JP Patent Application No. 2009-123432" with English translation.
"Preliminary Amendment filed on May 23, 2003 for KR Patent Application No. 10-2003-7005506" with English translation.
"Office Action dated Jul. 27, 2005 for KR Patent Application No. 10-2003-7005506 " with English translation.
"Argument Brief filed on Oct. 25, 2005 for KR Patent Application No. 10-2003-7005506" with English translation.
"Amendment filed on Oct. 25, 2005 for KR Patent Application No. 10-2003-7005506" with English translation.
"Office Action dated Jan. 5, 2006 for KR Patent Application No. 10-2003-7005506" with English translation.
"Argument Brief filed on Mar. 6, 2006 for KR Patent Application No. 10-2003-7005506" with English translation.
"Amendment filed on Mar. 6, 2006 for KR Patent Application No. 10-2003-7005506" with English translation.
"Notice of decision for patent dated Jun. 12, 2006 for KR Patent Application No. 10-2003-7005506" with English translation.
"Office Action dated Dec. 8, 2005 for KR Patent Application No. 10-2005-7020292" with English translation.
"Argument Brief filed on Mar. 8, 2006 for KR Patent Application No. 10-2005-7020292" with English translation.
"Amendment filed on Mar. 8, 2006 for KR Patent Application No. 10-2005-7020292" with English translation.
"Notice of decision for patent dated Apr. 17, 2006 for KR Patent Application No. 10-2005-7020292" with English translation.
"Office Action dated Oct. 4, 2005 for MX Patent Application No. PA/a/2003/003362" with English translation.
"Response filed on Dec. 15, 2005 for MX Patent Application No. PA/a/2003/003362" with English translation.
"Office Action dated Jun. 7, 2006 for MX Patent Application No. PA/a/2003/003362" with English translation.
"Response filed on Aug. 21, 2006 for MX Patent Application No. PA/a/2003/003362" with English translation.
"Notice of Allowance dated Oct. 18, 2006 for MX Patent Application No. PA/a/2003/003362" with English translation.
"Office Action dated Nov. 26, 2007 for MX Patent Application No. PA/a/2005/013764" with English translation.
"Office Action dated Mar. 7, 2007 for NO Patent Application No. 20031731" with English translation.
"Response filed on Sep. 10, 2007 for NO Patent Application No. 20031731" with English translation.
"Office Action dated Oct. 4, 2007 for NO Patent Application No. 20031731" with English translation.
"Response filed on May 7, 2008 for NO Patent Application No. 20031731" with English translation.
"Office Action dated May 16, 2008 for NO Patent Application No. 20031731" with English translation.
"Response filed on Aug. 18, 2008 for NO Patent Application No. 20031731" with English translation.
"Office Action dated Sep. 5, 2008 for NO Patent Application No. 20031731" with English translation.
"Response filed on Oct. 13, 2008 for NO Patent Application No. 20031731" with English translation.
"Notice of Allowance dated Oct. 31, 2008 for NO Patent Application No. 20031731" with English translation.
"Examination Report dated Oct. 13, 2003 for NZ Patent Application No. 525324".
"Response filed on Aug. 26, 2004 for NZ Patent Application No. 525324".
"Examination Report dated Sep. 2, 2004 for NZ Patent Application No. 525324".
"Response filed on Jan. 21, 2005 for NZ Patent Application No. 525324".
"Examination Report dated Feb. 18, 2005 for NZ Patent Application No. 525324".
"Notice of Acceptance of Complete Specification dated Mar. 4, 2005 for NZ Patent Application No. 525324".
"Formality Requirement dated Jun. 18, 2003 for PH Patent Application No. 1-2003-500266".
"Response filed on Aug. 5, 2003 for PH Patent Application No. 1-2003-500266".
"Office Action dated Aug. 8, 2003 for PH Patent Application No. 1-2003-500266".
"Response filed on Sep. 8, 2003 for PH Patent Application No. 1-2003-500266".
"Response filed on Sep. 15, 2003 for PH Patent Application No. 1-2003-500266".
"Office Action dated Jul. 21, 2006 for PH Patent Application No. 1-2003-500266".
"Response filed on Aug. 14, 2006 for PH Patent Application No. 1-2003-500266".
"Office Action dated Mar. 21, 2007 for PH Patent Application No. 1-2003-500266".
"Response filed on Apr. 17, 2007 for PH Patent Application No. 1-2003-500266".
"Office Action dated Jun. 27, 2007 for PH Patent Application No. 1-2003-500266".
"Response filed on Jul. 31, 2007 for PH Patent Application No. 1-2003-500266".
"Office Action dated Sep. 7, 2007 for PH Patent Application No. 1-2003-500266".
"Response filed on Oct. 15, 2007 for PH Patent Application No. 1-2003-500266".
"Notice of Allowability dated Nov. 28, 2007 for PH Patent Application No. 1-2003-500266".
"Response to the Notice of Allowability filed on Dec. 13, 2007 for PH Patent Application No. 1-2003-500266".
"Notification dated Apr. 25, 2008 for PH Patent Application No. 1-2003-500266".
"Response filed on Apr. 30, 2008 for PH Patent Application No. 1-2003-500266".
"Registered dated Feb. 24, 2009 for PH Patent Application No. 1-2003-500266".
"Office Action dated Jun. 29, 2004 for RU Patent Application No. 2003114740" with English translation.
"Response filed on Nov. 30, 2004 for RU Patent Application No. 2003114740" with English translation.
"Office Action dated Jan. 19, 2005 for RU Patent Application No. 2003114740" with English translation.
"Response filed on Mar. 17, 2005 for RU Patent Application No. 2003114740" with English translation.

(56) References Cited

OTHER PUBLICATIONS

"Notice of Allowance dated Apr. 19, 2005 for RU Patent Application No. 2003114740" with English translation.
"Amendment filed on Apr. 17, 2002 for TW Patent Application No. 90125928" with English translation.
"Rejection dated Apr. 26, 2004 for TW Patent Application No. 90125928" with English translation.
"Reexamination filed on Nov. 25, 2004 for TW Patent Application No. 90125928" with English translation.
"Office Action dated Oct. 11, 2007 for TW Patent Application No. 90125928" with English translation.
"Response filed on Dec. 11, 2007 for TW Patent Application No. 90125928" with English translation.
"Notice of Allowance dated Oct. 20, 2008 for TW Patent Application No. 90125928" with English translation.
"Notice of Allowance dated Jun. 3, 2008 for U.S. Appl. No. 11/293,785".
"Notice of Allowance dated Nov. 19, 2008 for U.S. Appl. No. 11/293,785".
"Notice of Allowance dated Feb. 27, 2009 for U.S. Appl. No. 11/293,785".
"Notice of Allowance dated May 18, 2009 for U.S. Appl. No. 11/293,785".
"Preliminary Amendment filed on Apr. 18, 2003 for U.S. Appl. No. 10/420,466".
"Office Action dated Apr. 13, 2005 for U.S. Appl. No. 10/420,466".
"Response filed on Jul. 1, 2005 for U.S. Appl. No. 10/420,466".
"Notice of Allowance dated Sep. 12, 2005 for U.S. Appl. No. 10/420,466".
"Notice of Allowance dated Jun. 13, 2006 for U.S. Appl. No. 10/420,466".
"Notice of Allowance dated Mar. 16, 2007 for U.S. Appl. No. 10/420,466".
Preliminary Amendment filed on Dec. 2, 2005 for U.S. Appl. No. 11/293,785.
"Preliminary Amendment filed on Feb. 3, 2006 for U.S. Appl. No. 11/293,785".
"Office Action dated Sep. 4, 2007 for U.S. Appl. No. 11/293,785".
"Response filed on Feb. 26, 2008 for U.S. Appl. No. 11/293,785".
"Notification of Non-Compliant Amendment filed on Jan. 13, 2005 for U.S. Appl. No. 10/420,466".
"Office Communication concerning dated Sep. 13, 2004 for U.S. Appl. No. 10/420,466".
"Response filed on Oct. 8, 2004 for U.S. Appl. No. 10/420,466".
"Preliminary Amendment filed on Oct. 27, 2003 for U.S. Appl. No. 10/420,517".
ISR dated Jan. 15, 2002 for International Patent Application No. PCT/JP01/09221.
IPRP dated Jan. 8, 2003 for International Patent Application No. PCT/JP01/09221.
Amendment filed on Aug. 4, 2004 for ZA Patent Application No. 2003/3567.
Notice of Acceptance dated Aug. 10, 2004 for ZA Patent Application No. 2003/3567.
Amendment filed on Aug. 17, 2004 for ZA Patent Application No. 2003/3567.
Amended description filed after receipt of search report for EP Patent Application No. 10809938.3; Dec. 8, 2011.
"Amendment filed on Dec. 12, 2011 for JO Patent Application No. 55/2011" with English translation.
"Written Amendment filed on Sep. 21, 2011 for JP Patent Application No. 2011-527665" with English translation.
"Written Statement filed on Sep. 21, 2011 for JP Patent Application No. 2011-527665" with English translation.
Amendment filed on Oct. 28, 2011 for LB Patent Application No. 9292.
Amendment filed on Feb. 9, 2011 for TW Patent Application No. 100104281.
"Amendment filed on Dec. 15, 2011 for VN Patent Application No. 1-2011-03484" with English translation.
"ISR dated Sep. 14, 2010 for International Patent Application No. PCT/JP2010/063804".
"IPRP dated Mar. 13, 2012 for International Patent Application No. PCT/JP2010/063804".
Amendment filed on Dec. 22, 2011 for ZA Patent Application No. 2011/08697.
"Voluntary Amendment filed on Feb. 9, 2010 for AU Patent Application No. 2005283422".
"Notice of Allowance dated Apr. 29, 2010 for AU Patent Application No. 2005283422".
"Voluntary Amendment filed on Jul. 6, 2010 for AU Patent Application No. 2005283422".
"Office Action dated Jul. 15, 2011 for CA Patent Application No. 2579810".
Response filed on Sep. 21, 2011 for CA Patent Application No. 2579810.
Notice of Allowance dated Oct. 17, 2011 for CA Patent Application No. 2579810.
Office Action dated Jun. 26, 2009 for CN Patent Application No. 200580026468.7 with English translation.
Response filed on Sep. 23, 2009 for CN Patent Application No. 200580026468.7 with English translation.
Amendment filed on Sep. 23, 2009 for CN Patent Application No. 200580026468.7 with English translation.
Office Action dated Nov. 20, 2009 for CN Patent Application No. 200580026468.7 with English translation.
Response filed on Jan. 11, 2010 for CN Patent Application No. 200580026468.7 with English translation.
Amendment filed on Jan. 11, 2010 for CN Patent Application No. 200580026468.7 with English translation.
Notice of Allowance dated Feb. 5, 2010 for CN Patent Application No. 200580026468.7 with English translation.
Communication regarding the expiry of opposition period for EP Patent Application No. 05783232.1; Feb. 19, 2010.
Decision to grant a European patent for EP Patent Application No. 05783232.1; Mar. 19, 2009.
Communication about intention to grant a European patent for EP Patent Application No. 05783232.1; Nov. 20, 2008.
Reply to official communication for EP Patent Application No. 05783232.1; Apr. 30, 2008.
Communication from the Examining Division for EP Patent Application No. 05783232.1; Feb. 7, 2008.
Maintainance of the application for EP Patent Application No. 05783232.1; Nov. 9, 2007.
Invitation to declare maintenance of the application for EP Patent Application No. 05783232.1; Sep. 25, 2007.
European Search Report for EP Patent Application No. 05783232.1; Sep. 7, 2007.
Notice Prior to Examination dated Mar. 9, 2009 for IL Patent Application No. 181697 with English translation.
Response to Notice Prior to Examination filed on Apr. 22, 2009 for IL Patent Application No. 181697 with English translation.
Office Action dated Dec. 20, 2010 for IL Patent Application No. 181697 with English translation.
Response filed on Jan. 26, 2011 for IL Patent Application No. 181697 with English translation.
Notice of Allowance dated Nov. 14, 2011 for IL Patent Application No. 181697 with English translation.
Notice of Allowance dated Sep. 20, 2011 for JP Patent Application No. 2006-535174 with English translation.
Japanese Patent Application Laid-Open No. S63-028427 with English translation.
Japanese Patent Application Laid-Open No. 2003-026576 with English translation.
WO00/071097 with English translation.
Office Action dated Sep. 28, 2011 for KR Patent Application No. 10-2007-7001347 with English translation.
Amendment filed on Nov. 24, 2011 for KR Patent Application No. 10-2007-7001347 with English translation.
Argument Brief filed on Nov. 24, 2011 for KR Patent Application No. 10-2007-7001347 with English translation.
ISR dated Nov. 15, 2005 for International Patent Application No. PCT/JP2005/016941.

(56) References Cited

OTHER PUBLICATIONS

IPRP dated Mar. 20, 2007 for International Patent Application No. PCT/JP2005/016941.
Office Action for JP2007-542863 dated May 29, 2012 with English translation.
Asano et al., "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
Hori et al., "Suppression of Solid Tumor Growth by Immunoneutralizing Monoclonal Antibody against Human Basic Fibroblast Growth Factor", Cancer Research., 51, 6180-4, 1991.
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Dias et al., "IL-12 Regulates VEGF and MMPs in a Murine Breast Cancer Model", International J. Cancer., 78, 361-5, 1998.
Liu et al., "Structure of Human Methionine Aminopeptidase-2 Complexed with Fumagillin", Science., 282, 1324-1327, 1998.
Wedge et al., "ZD4190: An Orally Active Inhibitor of Vascular Endothelial Growth Factor Signaling with Broad-Spectrum Antitumor Efficacy", Cancer Research., 60, 970-975, 2000.
Hannequin et al., "Design and Structure-Activity Relationship of a New Class of Potent VEGF Receptor Tyrosine Kinase Inhibitors", Journal of Medicinal Chemistry., 42: 5369-5389, 1999.
Fong et al., "SU5416 is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Laird et al., "SU6668 Is a Potent Antiangiogenic and Antitumor Agent That Induces Regression of Established Tumorsl", Cancer Research., 60, 4152-4160, 2000.
Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Beebe et al., "Pharmacological Characterization of CP-547,632, a Novel Vascular Endothelial Growth Factor Receptor-2 Tyrosine Kinase Inhibitor for Cancer Therapy1", Cancer Research. 63:7301-9, 2003.
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Modelsl", Cancer Research., 63, 5978-5991, 2003.
Kubo et al., "Novel Potent Orally Active Selective VEGFR-2 Tyrosine Kinase Inhibitors: . . . ureas", Journal of Medicinal Chemistry., 48, 1359-1366, 2005.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.
Podar et al., "GW654652, the pan-inhibitor of VEGF receptors, blocks the growth and migration of multiple myeloma cells in the bone marrow microenvironment", Blood.,103, 3474-3479, 2004.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Ueda et al., "VGA1155, a Novel Binding Antagonist of VEGF, Inhibits Angiogenesis In Vitro and In Vivo", Anticancer Research., 24, 3009-3017, 2004.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Mohammadi et al., "Crystal structure of an angiogenesis inhibitor bound to the FGF receptor tyrosine kinase domain", EMBO J., 17, 5896-5904, 1998.
Roberts et al., "Antiangiogenic and Antitumor Activity of a Selective PDGFR Tyrosine Kinase Inhibitor, CP-673,451", Cancer Research., 65, 957-966, 2005.
Kubo et al., "A Novel Series of 4-Phenoxyquinolines: Potent and Highly Selective Inhibitors of PDGF Receptor Autophosphorylation", Bioorganic and Medicinal Chemistry Letters., 7, 2935-2940, 1997.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research., 64, 6652-6659. 2004.
Nyati et al., "Radiosensitization by Pan ErbB Inhibitor CI-1033 in Vitro and in Vivo", Clinical Cancer Research., 10:691-700, 2004.
El-Abseri et al., "Chemoprevention of UV Light-Induced Skin Tumorigenesis by Inhibition of the Epidermal Growth Factor Receptor", Cancer Research., 64, 3958-3965, 2004.
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Experimental Medicine, Supplementary Volume, "A New Handbook of Genetic Engineering", Section 4, Yodosha, 2003(Japanese).
Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Masferrer et al., "COX-2 Inhibitors A New Class of Antiangiogenic Agents", Annals of N.Y. Acad. Science., 889:84-6, 1999.
Bramhall, S., "The Matrix Metalloproteinases and Their Inhibitors in Pancreatic Cancer", International J. Pancreatol., 21, 1-12, 1997.
AACR American Association Cancer Research, 92nd Annual Meeting, 42:583, Mar. 24-28, 2001, New Orleans, LA, USA, 3126.
AACR American Association Cancer Research., 93nd Annual Meeting, 43:1080, Apr. 6-10, 2002, San Francisco, CA, USA, 5347.
AACR American Association Cancer Research., 96th Annual Meeting, 46, (Abstract 2031), Anaheim, Orange County, CA, USA Apr. 2005.
EORTC-NCI-AACR Symp Mol Targets Cancer Ther., 2, (Abstract 172), 2004.
AACR American Association Cancer Research, 96th Annual Meeting, 46:1407, (Abstract 5981), Anaheim, Orange County CA USA Apr. 16-20, 2005.
AACR American Association Cancer Research, 96th Annual Meeting, 46 (Abstract 3033), Anaheim, Orange County CA USA Apr. 16-20, 2005.
"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.
ZK304709 (Proceedings of the American Association for Cancer Research, 46, (Abstract 5842), 2005.
EORTC-NCI-AACR Symp Mol Targets Cancer Ther., (Abstract 134), 2004.
EORTC-NCI-AACR Symp Mol Targets Cancer Ther., 2, (Abstract 151), 2004.
Proceedings of the American Association for Cancer Research, 44, 9, (Abstract 39), 2003.
Proceedings of the American Association for Cancer Research, 44, 9, (Abstract 40), 2003.

(56) References Cited

OTHER PUBLICATIONS

Proceedings of the American Association for Cancer Research, 45, 694, (Abstract 3005), 2004.
Proceedings of the American Association for Cancer Research, 44, 1479, (Abstract 6454), 2003.
Proc. Am. Soc. Clin. Oncology, (Abstract 776), 2003.
Am. Assoc. Cancer Research, A3394, 2005.
Am. Assoc. Cancer Research, A3405, 2005.
Recent Results and Ongoing Trials with Panitumumab (ABX-EGF), a Fully Human Anti-Epidermal Growth Factor Receptor Antibody, in Metastatic Colorectal Cancer, Clinical Colorectal Cancer. 2005; 5(1):21-3.
Kim, T., "Technology evaluation: Matuzumab, Merck KGaA", Curr Opin Mol Ther. 2004; 6(1):96-103.
Am. Assoc. Cancer Research, Abstract 5353, 2005.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
The Pharmacology of Monoclonal Antibody, vol. 113, Chapter 11, Rosenburg and Moore ed., Springer Verlag (1994) pp. 269-315.
LeDoussal et al. "Bispecific-Antibody-Mediated Targeting of Radiolabeled Bivalent Haptens: Theoretical, Experimental and Clinical Results", Int. J. Cancer Suppl. 7: 58-62, 1992.
Millstein and Cuello, "Hybrid hybridomas and their use in immunohistochemistry", Nature 305: 537-9, 1983.
Am. Assoc. Cancer Res. Abstract 3399, 2005.
Proceedings of the American Association for Cancer Research, 45, 594, (Abstract 2571), 2004.
Proceedings of the American Association for Cancer Research, 44, 865, (Abstract 3780), 2003.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Kruckeberg et al., "Pyrosequencing Technology as a Method for the Diagnosis of Multiple Endocrine Neoplasia Type 2", Clinical Chemistry, 50, 522-529, 2004.
Bartsch et al., "A RET double mutation in the germline of a kindred with FMTC", Exp. Clin Endocrinol Diabetes, 108, 128-132, 2000.
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Hara et al., "Amplification of c-myc, K-sam, and c-met in Gastric Cancers: Detection by Fluorescence In Situ Hybridization", Laboratory Investigation, 78, 1143-1153, 1998.
Office Action issued for JP Appl. No. 2007-529565 issued on May 8, 2012 with English translation.
Response to EP OA for EP 07806561.2 filed on Apr. 18, 2012.
Response to CN OA for CN200880003336.6 filed on May 3, 2012.
Response to IL OA for IL 195282 filed on May 28, 2012.
Response to AU OA for AU 2008211952 filed on Jun. 28, 2012.
Heinemann, V., et al., "Comparison of the Cellular Pharmacokinetics and Toxicity of . . . 1-beta-d-Arabinofuranosylcytosine", Cancer Research, 48, 4024-4031, 1988.
Hertel LW., et al., "Evaluation of the Antitumor Activity of Gemcitabine (2',2'-Difluoro-2'- deoxycytidine)", Cancer Research, 50, 4417-4422, 1990.
IPRP (PCT/JP2008/051024)dated Jul. 21, 2009, with English translation.
Office Action issued for CN 200880002425.9 on Mar. 2, 2011 with English translation.
Argument and Amendment for CN 200880002425.9 filed on Jul. 18, 2011 with English translation.
Office Action for CN 200880002425.9 issued on Mar. 7, 2012 with English translation.
Office Action for IL 199907 issued on Jun. 17, 2010 with English translation.
Response to Office Action for IL 199907 filed on Oct. 11, 2010 with English translation.
Office Action issued for EP06768437.3 (EPO Form1224) issued on Oct. 28, 2010.
Response to OA for EP10015141 filed on Mar. 5, 2012.
PCT/JP2006/0315563 Written Opinion of the International Searching Authority dated Feb. 5, 2008, with English translation.
PCT/JP2006/0315563 International Preliminary Report on Patentability dated Feb. 5, 2008, with English translation.
PCT/JP2006/0315698 Written Opinion of the International Searching Authority, dated Feb. 5, 2008, with English translation.
PCT/JP2006/0315698 International Preliminary Report on Patentability with dated Feb. 5, 2008, English translation.
Communication (Notice of Allowance) for JP2011-527665 dated Jul. 17, 2012 (with English translation).
Communication (Notice of Allowance) for EP07806561.2 dated Jun. 25, 2012.
Communication (Notice of Allowance) for EP06782407.8 dated Jun. 20, 2012.
Submission of Documents re UAa201203132, dated May 22, 2012 with English translation.
Office Letter for ZA 2011/08697, dated May 25, 2012.
Response to OA for U.S. Appl. No. 12/439,339, filed Jul. 30, 2012.
Submission of Documents for CO 12-022608 dated Jun. 12, 2012.
Chinese Office Action for CN 200680020317.5 dated Aug. 3, 2012 with English translation.
Official Letter for SG 201108602-2 dated Aug. 8, 2012.
Office Action for U.S. Appl. No. 13/083,338 dated Jun. 8, 2012.
European Search Report for EP 08846814.5 dated Jun. 18, 2012.
Office Action for JP2007-529565 dated Aug. 7, 2012 with English translation.
Noriyuki et al., "Anti-tumor effect of E7080, a novel angiogenesis inhibitor", Database Biosis (online) Biosciences Information Service, Philadelphia, PA, US., Database Accession No. PREV200800475929 (abstract), Aug. 2008, XP002677323.
Response to Chinese Office Action filed for CN 200880115011.7 dated Jul. 5, 2012, with English translation.
Japanese Office Action for JP2009-123432 dated Sep. 4, 2012, with English translation.
Response to Chinese Office Action for CN 200680020317.5 dated Sep. 11, 2012, with English translation.
Official Letter for CA Patent Application No. 2627598 dated Sep. 19, 2012.
Schlumberger et al., "A Phase 2 Trial of the Multi-Targeted Kinase Inhibitor LENVATINIB(E7080) in Advanced Medullary Thyroid Cancer (MTC)", 2012 ASCO Annual Meeting, Poster Presentation, Jun. 1-5, 2012.
Funahashi et al., "P-2123, Lenvatinib treatment of differentiated thyroid cancer (DTC): Analysis to identify biomarkers associated with response", The $71^{st}$ Annual Meeting of the Japanese Cancer Association, p. 339, Sep. 19-21, 2012.
Tohyama et al., "P-3111, Preclinical effect of lenvatinib on human thyroid cancer targeting angiogenesis and receptor tyrosine kinase signaling", The $71^{st}$ Annual Meeting of the Japanese Cancer Association, p. 502, Sep. 19-21, 2012.
Chinese Office Action for CN 200880003336.6 dated Sep. 5, 2012, with English translation.
Chinese Office Action for CN 200880115011.7 dated Sep. 5, 2012, with English translation.
Notice of Allowance for U.S. Appl. No. 12/986,638, Sep. 25, 2012.
Response to Chinese Office Action filed for CN 200880003336.6 dated Jul. 11, 2012, with English translation.
Office Action for U.S. Appl. No. 13/322,961 dated Sep. 25, 2012.
Notice of Allowance for U.S. Appl. No. 12/524,754 dated Oct. 9, 2012.
Office Action for CN 200780017371.9 dated Sep. 28, 2012 with English translation.

(56) References Cited

OTHER PUBLICATIONS

Office Action for JP 2008-516724 dated Oct. 9, 2012 with English translation.
Bemex et al., "Spatial and temporal patterns of c-kit-expressing cells in WlacZ/+ and WlacZ/WlacZ mouse embryos", Development 122:3023-3033 (1996).
Office Action for IL 200090 dated Oct. 15, 2012 with English translation.
Office Action (Notice of Allowance) for EP 06782407.8 dated Nov. 2, 2012.
Office Action (Notice of Allowance) for EP 07806561.2 dated Nov. 2, 2012.
Office Action for JP 2008-532141 dated Nov. 13, 2012 with English translation.
Response to Office Action for CN200880115011.7 dated Nov. 20, 2012 with English translation.
Office Action for U.S. Appl. No. 13/083,338 dated Nov. 23, 2012.
Response to Office Action for JP2011-527665 dated May 10, 2012 with English translation.
Explanation of Circumstances re Accelerated Examination filed for JP2011-527665 dated May 10, 2012 with English translation.
Office Action for in 1571/CHENP/2007 dated Oct. 30, 2012.
Office Action for AU 2008325608 dated Nov. 24, 2012.
Office Action for EP 07743994.1 dated Oct. 10, 2012.
Response to Office Action for IL 200090 dated Dec. 23, 2012 with English translation.
European Search Report for EP 10809938.3 dated Jan. 2, 2013.
Office Action for CN 201080030508.6 dated Nov. 30, 2012 with English translation.
Response to Office Action for EP 08704376.6 dated Jan. 2, 2013.
Response to Office Action for EP 08846814.5 dated Jan. 3, 2013.
Office Action for U.S. Appl. No. 13/083,338 dated Jan. 3, 2013.
Clinical Trial: AMG 706 20040273 Thyroid Cancer Study, Stage 4 Cancer Treatments, Chat w/a Cancer Info Expert About Stage 4 Cancer Treatment Options. Www.CancerCenter.com, Jul. 2005.
Polverino et al., "AMG 706, an Oral, Multikinase Inhibitor that Selectively Targets Vascular Endothelial Growth Factor, Platelet-Derived Growth Factor, and Kit Receptors, Potently Inhibits Angiogenesis and Induces Regression in Tumor Xenografts", Cancer Research, 66(1):8715-8721, Sep. 1, 2006.
Office Action for IL 205512 dated Dec. 20, 2012 with English translation.
Submission to European Patent Office for EP03791389.4 dated Dec. 20, 2012.
Communication from Israel Patent Office for IL 175363 dated Jan. 2, 2013 with English translation.
Notice of Allowance for U.S. Appl. No. 12/524,754 dated Jan. 18, 2013.
Amendment submitted for Korean Application No. 10-2009-7017694 dated Jan. 18, 2013 with English translation.
Response to Office Action for U.S. Appl. No. 13/322,961 dated Jan. 25, 2013.
Decision of Patent Grant for JP2008-516724 dated Jan. 22, 2013 with English translation.
Office Action for JP2008-556208 dated Jan. 22, 2013 with English translation.
Office Action for CN 200980103218.7 dated Sep. 29, 2012 with English translation.
Examination Report for NZ Patent Application No. 598291 dated Oct. 15, 2012.
International Preliminary Report on Patentability for PCT/JP2011/064430 dated Jan. 24, 2013 (English translation).
Response to Office Action for Canadian Patent Application No. 2627598 dated Jan. 25, 2013.
Office Action for Australian Patent Application No. 2009210098 dated Jan. 30, 2013.
Response to Office Action for European Application No. 07743994.1 dated Feb. 8, 2013.
Request to amend specification for Australian Patent Application No. 2008325608 dated Feb. 15, 2013.
Response to Office Action for Chinese Patent Application No. 200780017371.9 dated Nov. 30, 2012 with English translation.
European Search Report for EP 12195436.6 dated Feb. 21, 2013.
Office Action for Israel Patent Application No. 175363 dated Jan. 2, 2013 in English.
Amendment for New Zealand Patent Application No. 598291 dated Jan. 30, 2013.
Amendment for Chinese Patent Application No. 201080030508.6 dated Feb. 7, 2013 with English translation.
Response to Office Action for IL Patent Application No. 175363 dated Feb. 27, 2013 in English.
Notice of Allowance for AU Application No. 2008325608 dated Feb. 27, 2013.
Response to Office Action for IL Application No. 205512 dated Mar. 14, 2013 with English translation.
Communication (Notification on Defects in application) for IL Application No. 207089 dated Jan. 6, 2013 with English translation.
Office Action from CN Patent Application No. 200880115011.7 dated Feb. 25, 2013 with English translation.
Communication (Notice of Allowance) for CA Patent Application No. 2627598 dated Mar. 8, 2013.
Notice of Acceptance for NZ Application No. 598291 dated Feb. 15, 2013.
Kawano et al., "Presentation Abstract, Abstract Number; 1619,- Combination of VEGFR inhibitor lenvatinib (E7080) and Met/EphB4 inhibitor golvatinib (E7050) overcomes VEGFR inhibitor-resistant I tumor vascular", Annual Meeting 2013, Walter E. Washington Convention Center, Washington, DC, Apr. 6-10, 2013.
Response to Office Action for CN Application No. 200980103218.7 dated Feb. 16, 2013 with English translation.
Office Action for U.S. Appl. No. 13/624,278 dated Mar. 29, 2013.
Preliminary Amendment for U.S. Appl. No. 13/624,278, filed Sep. 21, 2012.
Response to Office Action for U.S. Appl. No. 13/083,338, filed Apr. 2, 2013.
Office Action from CN Patent Application No. 200780017371.9 dated Mar. 14, 2013 with English translation.
Response to Office Action for IN Patent Application No. 1571/CHENP/2007 dated Apr. 10, 2013.
Office Action for U.S. Appl. No. 11/997,719 dated Apr. 8, 2013.
Office Action for CN Patent Application No. 201080030508.6 dated Apr. 9, 2013 with English translation.
Office Action for CA Application No. 2652442 dated Apr. 16, 2013.
Office Action for IL Patent Application No. 217197 dated Apr. 11, 2013 with English translation.
Response to Office Action for IL Application No. 207089 dated Apr. 22, 2013 with English translation.
Preliminary Amendment for U.S. Appl. No. 13/870,507, filed Apr. 26, 2013.
Communication (Notice of Allowance) for EP Application No. 04818213.3 dated May 6, 2013.
Request to amend specification for Australian Patent Application No. 2009210098 dated May 9, 2013.
Amendment and RCE for U.S. Appl. No. 12/741,682 dated May 17, 2013.
Supplementary Observation for CN Application No. 200980103218.7 dated Mar. 13, 2013 (with English translation).
Response to Office Action for CN Application No. 200880115011.7 dated Apr. 11, 2013 (with English translation).
Office Action for EP08846814.5 dated Apr. 16, 2013.
Request for Continued Examination and Information Disclosure Statement for U.S. Appl. No. 12/524,754, filed Apr. 15, 2013.
Office Action for KR 10-2008-7013685 dated May 20, 2013 (with English translation).
Office Action for JP2008-532141 dated May 21, 2013 (with English translation).
Office Action for U.S. Appl. No. 12/439,339 dated May 23, 2013.
Applicant Interview Summary for U.S. Appl. No. 12/439,339 dated May 23, 2013.
Response to Office Action for CN201080030508.6 dated May 27, 2013 (with English translation).
Request for Substantive Examination for UA a201203132 dated Apr. 15, 2013(with English translation).

(56) References Cited

OTHER PUBLICATIONS

Request for Substantive Examination for ID W-00201201031 dated Jun. 3, 2013 (with English translation).
Notice of Acceptance (Notice of Allowance) for AU2009210098 dated Jun. 4, 2013.
Notice of Allowance for U.S. Appl. No. 13/083,338 dated Jun. 4, 2013.
"Amendment and Response to Office Action Under 37 C.F.R. § 1.111" submitted for U.S. Appl. No. 13/624,278, dated Jun. 28, 2013.
Notice of Allowance for CN Patent Application No. 200980103218.7 dated May 27, 2013 (with English translation).
Office Action for IL Application No. 195282 dated Apr. 10, 2013 (with English translation).
Notice of Allowance for U.S. Appl. No. 13/205,328 dated Jun. 10, 2013.
U.S. Appl. No. 13/923,858, filed Jun. 21, 2013.
Koyama et al., "Anti-tumor effect of E7080, a novel angiogenesis inhibitor", Folia Pharmacol. Jpn. 132, Therapeutic Agents Series (28), Molecular Target Drugs-1-1, pp. 100-104, Apr. 18, 2008.
Haiyi Jiang, "ZD6474: an Agent That Selectively Targets Both VEGFR Tyrosine Kinase and EGFR Tyrosine Kinase", Japanese Journal of Lung Cancer, vol.46, No. 3, Jun. 20, 2006, pp. 283-288.
Stefan Frings, "New Molecular Targeted Therapeutic Drugs Clinical Results of Bevacizumab in Non-Small Cell Lung Cancer (NSCLC)", Japanese Journal of Lung Cancer, vol.46, No. 3, Jun. 20, 2006, pp. 277-281.
Lumi Chikahisa et al., "TSU-68 JDR/flk-inhibitor, can modulate the anti-tumor activity of paclitaxel by the induction of endothelial cell and tumor cell apoptosis", 61st Annual Meeting of Japanese Cancer Association, 2002, vol. 61, No. 1374, 2002, p. 443.
Office Action for JP2009-551518 dated Jun. 18, 2013(with English translation).
The Argument and the Amendment for JP Patent Application No. 2008-532141 filed on Nov. 29, 2012 (with English translation).
The Argument and the Amendment for JP Patent Application No. 2008-556208 filed on Mar. 21, 2013 (with English translation).
The Argument and the Amendment for JP Patent Application No. 2008-516724 filed on Nov. 28, 2012 (with English translation).
The Explanation of Circumstances Concerning Accelerated Examination and the Amendment filed on May 10, 2012 for JP Patent Application No. 2011-527665 (with English translation).
The Argument and the Amendment for JP Patent Application No. 2009-123432 filed on Jun. 12, 2012 (with English translation).
The Argument and the Amendment for JP Patent Application No. 2009-529019 filed on Jul. 3, 2012 (with English translation).
Response to Office Action for CN Application No. 200780017371.9 dated May 29, 2013 (with English translation).
Response to Office Action for U.S. Appl. No. 11/997,719, filed Jul. 3, 2013.
Office Action for JP Application No. 2009-540099 dated Jul. 2, 2013 (with English translation).
Notice of Allowance for CN Patent Application No. 201080030508.6 dated Jul. 4, 2013 (with English translation).
Notice of Allowance for JP Patent Application No. P2008-0556208 dated Jul. 9, 2013 (with English translation).
Matsui et al., "Extracellular matrix of linitis plastica as possible new therapeutic target", Surgical treatment 89(3):301-306 (Sep. 1, 2013) (with English translation), (year = 2013).
Amendment for Application No. IL Patent Application No. 195282 dated Jul. 11, 2013 (with English translation).
Amended Claims for KR Patent Application 10-2010-7011023 dated Jul. 17, 2013 (with English translation).
Communication for EP Patent Application No. 10809938.3 dated Jul. 19, 2013.
Notice of Allowance for U.S. Appl. No. 12/524,754 dated Jul. 19, 2013.
Notice of Allowance for EP Patent Application No. 10015141.4 dated Jul. 1, 2013.
Response to Office Action for IL Patent Application No. 217197 dated Jul. 31, 2013 (with English translation).
Response to Communication for EP Patent Application No. 08846814.5 dated Aug. 1, 2013.
Office Action for CN Patent Application No. 200780017371.9 dated Jul. 3, 2013 (with English translation).
Office Action for MX Patent Application No. MX/a/2012/002011 dated Jul. 17, 2013 (with English translation).
Amendment (amending specification) for AU Patent Application No. 2012246490 dated Aug. 2, 2013.
Response to Office Action for EP Application No. 11798224.9 dated Aug. 2, 2013.
Nishio et al., "Phase 1 study of lenvatinib combined with carboplatin and paclitaxel in patients with non-small-cell lung cancer", British Journal of Cancer (2013), 109:538-544.
Amendment submitted for Korean Application No. 10-2008-7013685 dated Jul. 5, 2013 (with English translation).
Voluntary amendment for CA Patent Application No. 2704000 dated Aug. 6, 2013.
Amendment filed for JP Patent Application 2008-532141 dated Jul. 5, 2013 (with English translation).
Demand for Appeal Trial for JP Patent Application 2008-532141 dated Jul. 5, 2013 (with English translation).
Notice of Allowance for IL Patent Application No. 175363 dated Aug. 13, 2013 (with English translation).
Amendment filed for EP Application No. 12774278.1 dated Aug. 13, 2013.
Office Action for IL Patent Application No. 200090 dated Jul. 24, 2013 (with English translation).
Response to Office Action for U.S. Appl. No. 12/439,339 dated Aug. 22, 2013.
Communication to the Patent Office for CL Application No. 2012-00412 dated Aug. 31, 2012 (with English translation).
Communication to the Patent Office for AR Application No. P110100513 dated Aug. 27, 2013 (with English translation).
RCE and IDS filed for U.S. Appl. No. 13/083,338, filed Aug. 28, 2013.
Office Action for U.S. Appl. No. 13/238,085 dated Sep. 6, 2013.
Corrected English Translation for Office Action for JP Patent Application No. 2007-529565 dated Aug. 7, 2012.
Response to Office Action for MX Patent Application No. MX/a/2012/002011 dated Aug. 29, 2013 (with English Translation).
Final Office Action for U.S. Appl. No. 12/039,381 dated Sep. 12, 2013.
Preliminary Amendment for U.S. Appl. No. 14/002,018, filed Aug. 28, 2013.
Amended Claims for RU Patent Application No. 2013140169 dated Aug. 29, 2013 (with English translation).
Notice of Allowance for CN Application No. 200880115011.7 dated Aug. 5, 2013 (with English translation).
Amendment filed for JP Patent Application No. 2009-551518 dated Aug. 6, 2013 (with English translation).
Argument filed for JP Patent Application No. 2009-551518 dated Aug. 6, 2013 (partial English translation).
Response to Office Action for CA Patent Application No. 2652442 dated Sep. 5, 2013.
Amendment to claims for IN Patent Application No. 7026/CHENP/2013 dated Sep. 5, 2013.
Amendment filed for JP Patent Application No. 2009-540099 dated Aug. 13, 2013 (with English translation).
Argument filed for JP Patent Application No. 2009-540099 dated Aug. 13, 2013 (with partial English translation).
Preliminary Amendment filed for U.S. Appl. No. 13/805,826 dated Sep. 9, 2013.
Request for Continued Examination and Information Disclosure Statement for U.S. Appl. No. 13/205,328 dated Sep. 10, 2013.
Notice of Allowance for JP Patent Application No. P2008-532141 dated Sep. 10, 2013 (with English translation).
Amendments for CN Patent Application No. 201280010898.X dated Aug. 29, 2013 (with English translation).
Notice of Allowance for U.S. Appl. No. 13/624,278 dated Sep. 16, 2013.
Notice of Allowance for EP Patent Application No. 04818213.3 dated Sep. 19, 2013.

(56) References Cited

OTHER PUBLICATIONS

Response to Office Action for IN Application No. 1571/CHENP/2007 dated Oct. 30, 2013.
RCE and Response to Final Office Action for U.S. Appl. No. 12/039,381 dated Oct. 23, 2013.
Response to Office Action for MX Patent Application No. MX/a/2010/008187 dated Nov. 4, 2013 (with English Translation).
Response to Office Action for PH Application No. 1-2011-502441 dated Nov. 4, 2013.
IPRP for PCT/JP2012/060279 dated Oct. 31, 2013.
Notice of Allowance for U.S. Appl. No. 12/439,339 dated Nov. 7, 2013.
Notice of Allowance for JP Patent Application No. P2009-551518 dated Oct. 22, 2013 (with English translation).
Office Action for U.S. Appl. No. 13/238,085 dated Nov. 12, 2013.
Office Action for CA Patent Application No. 2652442 dated Oct. 4, 2013.
Response to Office Action for CO Patent Application No. 12-022608 dated Nov. 13, 2013 (with English translation).
Amendment for BR Patent Application No. 112012032462-4 dated Nov. 4, 2013 (with English translation).
Wang, Y., "Drugs of Today, Everolimus in renal cell carcinoma", Journals of the Web, 46(8):Abstract, Aug. 2010.
Office Action for CN Patent Application No. 201180030568.2 dated Oct. 12, 2013 (with English translation).
Office Action for IN Patent Application No. 1571/CHENP/2007 dated Oct. 23, 2013.
Office Action for IL Patent Application No. 205512 dated Oct. 28, 2013 (with English translation).
Notice of Allowance for U.S. Appl. No. 12/524,754 dated Nov. 22, 2013.
Preliminary Amendment filed for U.S. Appl. No. 14/117,276, filed Nov. 12, 2013.
Preliminary Amendment filed for EP Patent Application No. 12786619.2 dated Nov. 13, 2013.
Voluntary amendment filed for CA Patent Application No. 2802644 dated Nov. 22, 2013.
Amendment filed for KR Patent Application No. 10-2008-7029472 dated Nov. 20, 2013 (with English translation).
Amendment filed for EP Application No. 12793322.4 dated Nov. 28, 2013.
Request for Continued Examination and Information Disclosure Statement filed for U.S. Appl. No. 13/083,338 dated Dec. 2, 2013.
Amendment for KR Patent Application No. 10-2013-7020616 dated Nov. 22, 2013 (with English translation).
IPRP of International Patent Application No. PCT-JP2012-062509 dated Nov. 28, 2013.
Decision of Patent Grant for KR Patent Application No. 10-2008-7013685 dated Nov. 29, 2013 (with English translation).
Office Action for IN Patent Application No. 1571/CHENP/2007 dated Dec. 9, 2013.
Preliminary Amendment filed for U.S. Appl. No. 14/122,339 dated Nov. 26, 2013.
Response filed for KR Application No. 10-2009-7005657 dated Nov. 21, 2013 (with English translation).
Notice of Allowance for IL Patent Application No. 200090 dated Nov. 18, 2013 (with English translation).
Office Action for MX Patent Application No. MX/a/2012/002011 dated Nov. 21, 2013 (with English translation).
Office Action for CN Patent Application No. 200680020317.5 dated Nov. 28, 2013 dated Nov. 28, 2013 (with English translation).
Request for Continued Examination filed for U.S. Appl. No. 11/997,719 dated Dec. 11, 2013.
Request for Continued Examination filed for U.S. Appl. No. 13/624,278 dated Dec. 13, 2013.
Response to Office Action and Information Disclosure Statement filed for U.S. Appl. No. 11/997,543 dated Dec. 19, 2013.
Office Action of MX Patent Application No. MX-a-2010-008187 dated Dec. 5, 2013 (with English translation).
Office Action of CO Patent Application No. 12-022608 Dec. 17, 2013 (with English translation).
Office Action of IL Patent Application No. 207089 dated Nov. 25, 2013 (with English translation).
RCE filed for U.S. Appl. No. 13/205,328 dated Dec. 30, 2013.
Almarsson et al., "High-Throughput Surveys of Cyrstal Form Diversity of Highly Polymorphic Pharmaceutical Compounds", Crystal Growth & Design, pp. 927-933 (2003).
Amendment for CO Application No. 12-022608 dated Jan. 28, 2014 (with English translation).
Amendment for IN Patent Application No. 1571/CHENP/2007 dated Jan. 23, 2014.
Amendment to Specification for KR Patent Application No. 10-2009-7017694 dated Feb. 28, 2014 (with English translation).
Argument for KR Patent Application No. 10-2009-7017694 dated Feb. 28, 2014 (with English translation).
European Search Report for EP 11798224.9 dated Mar. 4, 2014.
International Preliminary Report (IPRP) for PCT/US2012/040183 dated Apr. 3, 2014.
Notice of Allowance for U.S. Appl. No. 12/439,339 dated Apr. 1, 2014.
Notice of Allowance for U.S. Appl. No. 13/205,328 dated Jan. 30, 2014.
Notice of Allowance for US Appl. No. 13/083,338 dated Feb. 6, 2014.
Notice of Allowance for U.S. Appl. No. 12/524,754 dated Feb. 13, 2014.
Office Action for CA Application No. 2676796 dated Dec. 30, 2013.
Office Action for CN Application No. 200680020317.5 dated Mar. 4, 2014 (with English translation).
Office Action for CN Application No. 201180030568.2 dated Mar. 24, 2014 (with English translation).
Office Action for EP Application No. 04807580.8 dated Mar. 18, 2014.
Office Action for European Patent Application No. 08704376.6 dated Feb. 24, 2014.
Office Action for JP Application No. P2009-540099 dated Mar. 25, 2014 (with English translation).
Office Action for KR Application No. 10-2008-7029472 dated Mar. 28, 2014 (with English translation).
Office Action for KR Application No. 10-2009-7005657 dated Mar. 28, 2014 (with English translation).
Office Action for KR Application No. 10-2009-7017694 dated Jan. 29, 2014 (with English translation).
Office Action for PH Application No. 1-2011-502441 dated Feb. 19, 2014.
Office Action for U.S. Appl. No. 12/039,381 dated Jan. 9, 2014.
Office Action for U.S. Appl. No. 13/805,826 dated Apr. 2, 2014.
Office Action for U.S. Appl. No. 13/923,858 dated Apr. 18, 2014.
Office Action for U.S. Appl. No. 14/002,018 dated Apr. 14, 2014.
Final Office Action for U.S. Appl. No. 11/997,543 dated Mar. 11, 2014.
Office Action for U.S. Appl. No. 11/662,425 dated Feb. 27, 2014.
Office Action for VN Application No. 10-2011-03484 dated Dec. 31, 2013 (with English translation).
O'Reilly et al., "Hydrolysis of tert-Butyl Methyl Ether(MTBE) in Dilute -Aqueous Acid", Environ.Sci.Technol; 35, 2001, pp. 3954-3961.
Patel et al., "The effect of excipients on the stability of levothyroxine sodium pentahydrate tables", International Journal of Pharmaceutics; 264, pp. 35-43 (2003).
Request for Continued Examination for U.S. Appl. No. 12/439,339 dated Jan. 27, 2014.
Request for Continued Examination for U.S. Appl. No. 12/741,682 dated Jan. 17, 2014.
Request for Continued Examination for U.S. Appl. No. 12/524,754 dated Feb. 3, 2013.
Response filed for IN Patent Application No. 6415/CHENP/2008 dated Jan. 17, 2014.
Response to CN Application No. 201180030568.2 dated Jan. 13, 2014 (with English translation).
Response to Office Action for CA Patent Application No. 2652442 dated Jan. 8, 2014.

(56) References Cited

OTHER PUBLICATIONS

Response to Office Action for CN 2006800203175 filed on Jan. 9, 2014 (with English translation).
Response to Office Action for MX Patent Application No. MX/a/2010008187 dated Feb. 17, 2014 (with English translation).
Response to Office Action for MX-a-2012-002011 dated Jan. 16, 2014 (with English translation).
Response to Office Action for Philippines Patent Application No. 1-2011-502441 dated Feb. 28, 2014.
Response to Office Action for U.S. Appl. No. 12/039,381 dated Apr. 3, 2014.
Search Report for EP Patent Application No. 11798224.9 dated Mar. 21, 2014.
Stahl and Wermuth, Handbook of Pharmaceutical Salts: Properties, Selection and Use, pp. 117-122 (2002).
Submission for VN Application No. 1-2011-03484 dated Feb. 28, 2014 (with English translation).
Winkler et al., "Kinetics of vascular normalization by VEGFR2 blockade governs brain tumor response to radiation: Role of oxygenation, angiopoietin-1, and matrix metalloproteinases", Cancer Cell vol. 6:553-563 (2004).
Xiaotian Zhang et al. "Synergic antiproliferative effect of DNA methyltransferase inhibitor in combination with anticancer drugs in gastric carcinoma", Cancer Science, vol. 97, No. 9, Sep. 2006, pp. 938-944.
Associate's comments about the Board of Appeal for EP Patent Application No. 04807580.8 dated Jul. 7, 2014.
Besson et al., "PTEN/MMAC1/TEP1 in signal transduction and tumorigenesis", European Journal of Biochemistry, 263:605-611 (1999).
Dankort et al., "Braf$^{V600E}$ cooperates with Pten loss to induce metastatic melanoma", Nature Genetics, 41(5):544-552 (2009).
Davies et al., "Mutations of the BRAF gene in human cancer", Nature 417:949-954 (2002).
Final Office Action for U.S. Appl. No. 14/002,018 dated Jul. 25, 2014.
Final Office Action for U.S. Appl. No. 12/039,381 dated May 29, 2014.
Finn et al., "A multicenter, open-label, phase 3 trial to compare the efficacy and safety of lenvatinib (E7080) versus sorafenib in first-line treatment of subjects with unresectable hepatocellular carcinoma.", American Society of Clinical Oncology, Annual Meeting Abstract, May 31, 2014 31,2014.
Fuji et al., Angiogenesis Inhibitor/Kekkan Shinsei Sogaiyaku, Clinical Gastroenterology, 19:220-227 (2004) (with English translation).
Havel et al., "E7080 (lenvatinib) in addition to best supportive care (BSC) versus BSC alone in third-line or greater nonsquamous, non-small cell lung cancer (NSCLC).", American Society of Clinical Oncology, Annual Meeting Abstract, May 31, 2014.
Matsui et al., "Multi-Kinase" Inhibitor E7080 Suppresses Lymph Node and Lung Metastases of Human Mammary Breast Tumor MDA-MB-231 via Inhibition of Vascular Endothelial Growth Factor•Receptor (VEGF-R) 2 and VEGF-R3 Kinase, Clinical Cancer Research, 14:459-465 (2008).
Nakagawa et al., E7050: A dual c-Met and VEGFR-2 tyrosine kinase inhibitor promotes tumor regression and prolongs survival in mouse xenograft models, Cancer Science 101(1):210-215 (2009).
Nakazawa et al., "Miximizing the efficacy of anti-angiogenesis cancer therapy: A multi-targeting strategy by tyrosine kinase inhibitors", Abstract No. 2980 Hall E-E, Poster Section 2 printed May 13, 2014.
Nakazawa et al., "Miximizing the efficacy of anti-angiogenesis cancer therapy: A multi-targeting strategy by tyrosine kinase inhibitors", AACR Annual Meeting, Abstract, Apr. 5-9, 2014.
Nakazawa, "Combination strategy of lenvatinib: Maximizing its anti-angiogenesis efficacy", Tsukuba Research Laboratory, Eisai Co., Ltd., Ibaraki, Japan, Jun. 27, 2014.
Notice of Allowance for U.S. Appl. No. 13/624,278 dated Jun. 25, 2014.
Notice of Allowance for CA Application No. 2652442 dated Apr. 16, 2014.
Notice of Allowance for U.S. Appl. No. 11/997,719 dated Jun. 5, 2014.
Notice of Allowance for U.S. Appl. No. 13/083,338 dated Jul. 10, 2014.
Notice of Allowance for U.S. Appl. No. 13/205,328 dated May 8, 2014.
Notice of Allowance for UA Patent Application No. a201203132 dated Mar. 21, 2014 (with English translation).
Notice of Allowance for VN Application No. 1-2011-03484 dated Apr. 28, 2014 (with English translation).
Office Action for MX/a/2012/014776 dated Apr. 4, 2014 (with English translation).
Office Action for CA Patent Application No. 2771403 dated Jul. 16, 2014.
Office Action for EP Application No. 03791389.4 dated Jun. 10, 2014.
Office Action for EP Application No. 08846814.5 dated Jun. 4, 2014.
Office Action for MX Application No. MX/a/2010/008187 dated Apr. 28, 2014 (with English translation).
Office Action for MX Application No. MX/a/2012/002011 dated Apr. 28, 2014 (with English translation).
Office Action for RU Application No. 2012103471 dated May 20, 2014 (with English translation).
Office Action for U.S. Appl. No. 11/662,425 dated Jun. 5, 2014.
Office Action for U.S. Appl. No. 13/805,826 dated Jul. 1, 2014.
Office Action for U.S. Appl. No. 14/002,018 dated Jun. 9, 2014.
Official Notification for EP 04807580.8 dated Jun. 16, 2014.
Official Notification for EP 04807580.8 dated Jun. 27, 2014.
Request for Continued Examination filed for U.S. Appl. No. 13/083,338 dated May 6, 2014.
Request for Continued Examination for U.S. Appl. No. 13/205,328 dated Apr. 28, 2014.
Request for Continued Examination for U.S. Appl. No. 12/524,754 dated May 13, 2014.
Response filed for EP Patent Application No. 04807580.8 dated May 16, 2014.
Response filed for KR Patent Application No. 10-2008-7029472 dated May 1, 2014 (with English translation).
Response filed for KR Patent Application No. 10-2009-7005657 dated May 7, 2014 (with English translation).
Response filed for SG Patent Application No. 201108602-2 dated May 22, 2014.
Response to Office Action for CN Application No. 201180030568.2 dated May 14, 2014 (with English translation).
Response to Office Action for EP Application No. 08704376.6 dated Apr. 30, 2014.
Response to Office Action for JP2009-540099 dated Apr. 28, 2014, (with English translation).
Response to Office Action for U.S. Appl. No. 11/662,425 dated May 20, 2014.
Response to Office Action for U.S. Appl. No. 14/002,018 dated May 28, 2014.
Schlumberger et al, "A phase 3, multicenter, double-blind, placebo controlled trial of lenvatinib (E7080) in patients with 131I refractory differentiated thyroid cancer (SELECT).", American Society of Clinical Oncology, Annual Meeting Abstract, Jun. 2, 2014.
Shumaker et al., "Effect of lenvatinib (E7080) on the QTc interval: results from a thorough QT study in healthy volunteers", Cancer Chemother Pharmacol, Springer-Verlag Berlin Heidelberg (2014) (online).
Submission for EP 04807580.8 dated Jun. 13, 2014.
Submission for EP 04807580.8 dated Jun. 16, 2014.
Submission of Document for CA Application No. 2676796 dated Jun. 27, 2014.
Submission of Document for U.S. Appl. No. 13/205,328 dated Jul. 8, 2014.
Submission of Documents for EP Patent Application No. 08846814.5 dated Jul. 24, 2014.
Submission of Documents for Korean Patent Application No. 10-2012-7003846 dated Jun. 18, 2014 (with English translation).
Submission of Documents for MX Application No. MX/a/2010/008187 dated Jun. 25, 2014 (with English translation).

(56) References Cited

OTHER PUBLICATIONS

Submission of Documents for MX Application No. MX/a/2012/014776 dated Jun. 20, 2014 (with English translation).
Submission of Documents for MY Patent Application No. PI2011700172 dated Jul. 3, 2014 (in English).
Submission of Documents for RU Patent Application No. 2012103471 dated Jul. 21, 2014.
Submission of Documents for U.S. Appl. No. 13/805,826 dated Jun. 2, 2014.
Vergote et al., "Prognostic and predictive role of circulating angiopoietin-2 in multiple solid tumors; An analysis of approximately 500 patients treated with lenvatinib across tumor types.", American Society of Clinical Oncology, Annual Meeting Abstract, May 31, 2014.
Wang et al., "KRAS, BRAF, PIK3CA Mutations and PTEN Expression in Human Colorectal Cancer-Relationship With Metastatic Colorectal Cancer", Ann. Oncol. 21 (Supp 6) P-0124.
Yamori et al., Current Treatment of Solid Tumors New Approaches of Treatment, Drug Treatment Kinase Inhibitors/Kokeigan no Saishin Chiryo Chiryo no Aratana Torikumi Yakubutsu Ryoho Kinase Inhibitors, Japanese Journal of Clinical Medicine 68(6):1059-1066 (2010) (with English translation).
Yokota, "ASCO report: Gastrointestinal Cancer field/ASCO Hokoku Shokakigan Ryoiki", Gan Bunshi Hyoteki Chiryo, 8(4):271-283 (2010) (with English translation).

COMBINATION OF ANTI-ANGIOGENIC SUBSTANCE AND ANTI-TUMOR PLATINUM COMPLEX

FIELD OF THE INVENTION

The present invention relates to a pharmaceutical composition and a kit comprising a compound represented by General Formula (I), a pharmacologically acceptable salt thereof or a solvate thereof (hereinafter, also referred to as the "compound of the invention") used in combination with an anti-tumor platinum complex, to a method for treating cancer characterized by administering an effective amount of the pharmaceutical composition to a patient, to use of a compound of the invention for producing the pharmaceutical composition, and to a compound of the invention for the pharmaceutical composition, etc.

BACKGROUND OF THE INVENTION

Examples of substances conventionally used as chemotherapeutic agents for cancer include alkylating agents such as cyclophosphamide, antimetabolites such as methotrexate and fluorouracil, antibiotics such as adriamycin, mitomycin and bleomycin, plant-derived agents such as paclitaxel, vincristine and etoposide and metal complexes such as a platinum formulation. None of them, however, have satisfactory anti-tumor effect and thus there has been a strong need for development of a novel anti-tumor agent.

Formulations comprising an anti-tumor platinum complex as an active element are known as platinum formulations. Examples of such anti-tumor platinum complexes include cisplatin, carboplatin, nedaplatin, zeniplatin, enloplatin, lobaplatin, ormaplatin, loboplatin, sebriplatin, oxaliplatin, miboplatin and spiroplatin. Such platinum formulations have been approved and developed for application to testicular tumor, bladder cancer, renal pelvic/ureteral tumor, prostate cancer, ovarian cancer, head and neck cancer, non-small-cell lung cancer, esophageal cancer, cervical cancer, neuroblastoma, gastric cancer, osteosarcoma, small cell lung cancer, malignant lymphoma, hepatocellular carcinoma or the like. In addition, combination therapy for various cancers has also been approved or developed by combining a platinum formulation including an anti-tumor platinum complex with various drugs, for example, with paclitaxel for non-small-cell lung cancer and with gemcitabine for non-small-cell lung cancer.

In a test by Abratt et al., a median survival period obtained with combined use of vinorelbine and carboplatin was 8.6 months while a median survival period obtained with combined use of vinorelbine and gemcitabine was 11.5 months. These results showed that combination therapy without a platinum formulation was better than combination therapy with a platinum formulation. That is to say that even if a platinum formulation has anti-tumor effect, the effect is not necessarily enhanced by simply combining with other drugs, and that selection of drugs for anti-tumor effect enhancement is yet unobvious (Non-patent references 1-9)

Furthermore, 4-(3-chloro-4-(cyclopropylaminocarbonyl)aminophenoxy)-7-methoxy-6-quinolinecarboxamide is known as a VEGF receptor kinase inhibitory substance (Patent References 1-2).

However, there is no report as to whether or not pharmaceutical compositions comprising these substances in combination have any anti-tumor effect.

[Patent Reference 1] International Publication No. WO2002/32872

[Patent Reference 2] International Publication No. WO2005/063713

[Non-Patent Reference 1] Paclitaxel+carboplatin: Paclitaxel plus carboplatin in advanced non-small-cell lung cancer: a phase II trial (J. Clin Oncol., 14(7), 2054-2060, 1996)

[Non-Patent Reference 2] Paclitaxel+cisplatin: Phase III comparative study of high-dose cisplatin versus a combination of paclitaxel and cisplatin in patients with advanced non-small-cell lung cancer. (J. Clin Oncol., 18(19), 3390-3399, 2000)

[Non-Patent Reference 3] Vinorelbine+cisplatin: Randomized trial comparing cisplatin with cisplatin plus vinorelbine in the treatment of advanced non-small-cell lung cancer: a Southwest Oncology Group study. (J. Clin Oncol., 16(7), 2459-65, 1998)

[Non-Patent Reference 4] Gemcitabine+cisplatin: Phase III trial of gemcitabine plus cisplatin versus cisplatin alone in patients with locally advanced or metastatic non-small-cell lung cancer. (J. Clin Oncol., 18(1)), 122-130, 2000)

[Non-Patent Reference 5] Gemcitabine+carboplatin: Phase II study of gemcitabine and carboplatin in patients with advanced non-small-cell lung cancer. (Cancer Chemother Pharmacol., 60 (4), 601-607, 2007)

[Non-Patent Reference 6] CPT-11 (Irinotecan)+cisplatin: A phase II study of irinotecan plus cisplatin for patients with advanced stage IIIB or IV NSCLC previously treated with nonplatinum-based chemotherapy. (Cancer, 107(4), 799-805, 2006) [Non-Patent Reference 7] J. Clin Oncol. 24(3):419-430, 2006

[Non-Patent Reference 8] Other: Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan. (Ann Oncol., 18(2), 317-323, 2006) [Non-Patent Reference 9] Lung Cancer 2005, Vol. 49, No2, pp. 233-240

DISCLOSURE OF THE INVENTION

Problems to be Solved by the Invention

The present invention was achieved regarding the circumstances described above and the problems to be solved by the invention are to find a pharmaceutical composition and a kit that show excellent anti-tumor effect and a method for treating cancer.

Means for Solving the Problems

In order to solve the above-mentioned problems, the present inventors have gone through keen research and found that an angiogenesis inhibitory substance such as 4-(3-chloro-4-(cyclopropylaminocarbonyl)aminophenoxy)-7-methoxy-6-quinolinecarboxamide shows excellent anti-tumor effect when combined with an anti-tumor platinum complex.

Thus, the present invention relates to the followings.

(1) A pharmaceutical composition comprising a compound represented by General Formula (1), a pharmacologically acceptable salt thereof or a solvate thereof in combination with an anti-tumor platinum complex.

(2) A kit comprising:

(a) at least one selected from the group consisting of a packaging container, an instruction and a package insert describing use of a compound represented by General Formula (I), a pharmacologically acceptable salt thereof or a solvate thereof in combination with an anti-tumor platinum complex; and (b) a pharmaceutical composition comprising a compound represented by General Formula (I), a pharmacologically acceptable salt thereof or a solvate thereof (3) A kit characterized by comprising a set of a formulation containing a compound represented by General Formula (I), a pharmacologically acceptable salt thereof or a solvate thereof and a formulation containing an anti-tumor platinum complex.

(4) A pharmaceutical composition comprising a compound represented by General Formula (I), a pharmacologically acceptable salt thereof or a solvate thereof that is simultaneously or separately administered to a patient with an anti-tumor platinum complex.

(5) A method for treating cancer characterized by simultaneously or separately administering effective amounts of a compound represented by General Formula (I), a pharmacologically acceptable salt thereof or a solvate thereof and an anti-tumor platinum complex to a patient.

(6) Use of a compound represented by General Formula (I), a pharmacologically acceptable salt thereof or a solvate thereof for producing a pharmaceutical composition in combination with an anti-tumor platinum complex.

(7) A compound represented by General Formula (I), a pharmacologically acceptable salt thereof or a solvate thereof for a pharmaceutical composition in combination with an anti-tumor platinum complex.

The compound represented by General Formula (I), a pharmacologically acceptable salt thereof or a solvate thereof is as follows:

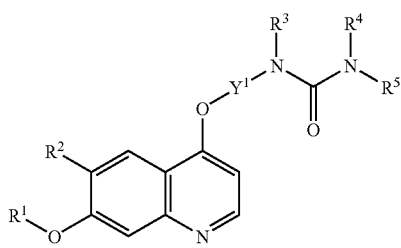

[wherein, $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —$CONR^6$—, a group represented by Formula —$SO_2NR^6$—, a group represented by Formula —$NR^6SO_2$—, a group represented by Formula —$NR^6CO$— or a group represented by Formula —$NR^6$— (wherein, $R^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group);
$R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{12}$ (wherein, $V^{an}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group);
$Y^1$ represents a group represented by either one of the following formulae

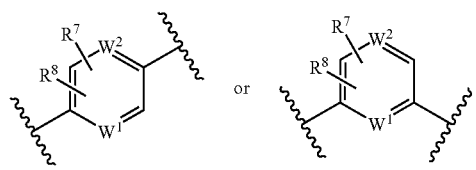

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);
$W^1$ and $W^2$ each independently represent an optionally substituted carbon atom or nitrogen atom);
$R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group; and
$R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-5}$ cycloalkyl group, an optionally substituted $C_{6-10}$ aryl group, an optionally substituted 5-10-membered heteroaryl group or an optionally substituted 3-10-membered nonaromatic heterocyclic group],
a pharmacologically acceptable salt thereof or a solvate thereof.

The anti-tumor platinum complex is, for example, cisplatin, carboplatin, nedaplatin, zeniplatin, enloplatin, lobaplatin, ormaplatin, loboplatin, sebriplatin, oxaliplatin, miboplatin or spiroplatin Furthermore, the present invention preferably relates to the followings.

(8) A pharmaceutical composition comprising 4-(3-chloro-4-(cyclopropylaminocarbonyl)aminophenoxy)-7-methoxy-6-quinolinecarboxamide, a pharmacologically acceptable salt thereof or a solvate thereof in combination with cisplatin or carboplatin.

(9) A kit comprising:
(a) at least one selected from the group consisting of a packaging container, an instruction and a package insert describing use of 4-(3-chloro-4-(cyclopropylaminocarbonyliaminophenoxy)-7-methoxy-6-quinolinecarboxamide, a pharmacologically acceptable salt thereof or a solvate thereof in combination with cisplatin or carboplatin; and
(b) a pharmaceutical composition comprising 4-(3-chloro-4-(cyclopropylaminocarbonyl)aminophenoxy)-7-methoxy-6-quinolinecarboxamide, a pharmacologically acceptable salt thereof or a solvate thereof

(10) A kit characterized by comprising a set of a formulation containing 4-(3-chloro-4-(cyclopropylaminocarbonyl)aminophenoxy)-7-methoxy-6-quinolinecarboxamide, a pharmacologically acceptable salt thereof or a solvate thereof and a formulation containing cisplatin or carboplatin.

(11) A pharmaceutical composition comprising 4-(3-chloro-4-(cyclopropylaminocarbonyl)aminophenoxy)-7-methoxy-6-quinolinecarboxamide, a pharmacologically acceptable salt thereof or a solvate thereof that is simultaneously or separately administered to a patient with cisplatin or carboplatin.

(12) A method for treating cancer characterized by simultaneously or separately administering effective amounts of 4-(3-chloro-4-(cyclopropylaminocarbonyliaminophenoxy)-7-methoxy-6-quinolinecarboxamide, a pharmacologically acceptable salt thereof or a solvate thereof, and cisplatin or carboplatin to a patient.

(13) Use of 4-(3-chloro-4-(cyclopropylaminocarbonyl)aminophenoxy)-7-methoxy-6-quinolinecarboxamide, a pharmacologically acceptable salt thereof or a solvate thereof for producing a pharmaceutical composition in combination with cisplatin or carboplatin.

(14) 4-(3-Chloro-4-(cyclopropylaminocarbonyl)aminophenoxy)-7-methoxy-6-quinolinecarboxamide, a pharmacologically acceptable salt thereof or a solvate thereof for a pharmaceutical composition in combination with cisplatin or carboplatin.

Effect of the Invention

The present invention provides a pharmaceutical composition and a kit that exhibit excellent anti-tumor effect. Specifically, the present invention provides a pharmaceutical composition and a kit comprising a compound represented by General Formula (I), a pharmacologically acceptable salt thereof or a solvate thereof in combination with an anti-tumor platinum complex. The pharmaceutical composition and the kit of the invention can be used for the treatment of cancer.

BRIEF DESCRIPTION OF THE DRAWING

In FIG. 1, E7080 represents 4-(3-chloro-4-(cyclopropylaminocarbonyl)aminophenoxy)-7-methoxy-6-quinolinecarboxamide.

In FIG. 2, E7080 represents 4-(3-chloro-4-(cyclopropylaminocarbonyl)aminophenoxy)-7-methoxy-6-quinolinecarboxamide.

In FIG. 3, E7080 represents 4-(3-chloro-4-(cyclopropylaminocarbonyl)aminophenoxy)-7-methoxy-6-quinolinecarboxamide.

In FIG. 4, E7080 represents 4-(3-chloro-4-(cyclopropylaminocarbonyl)aminophenoxy)-7-methoxy-6-quinolinecarboxamide.

In FIG. 5, E7080 represents 4-(3-chloro-4-(cyclopropylaminocarbonyl)aminophenoxy)-7-methoxy-6-quinolinecarboxamide.

BEST MODE FOR CARRYING OUT THE INVENTION

Figure 1:
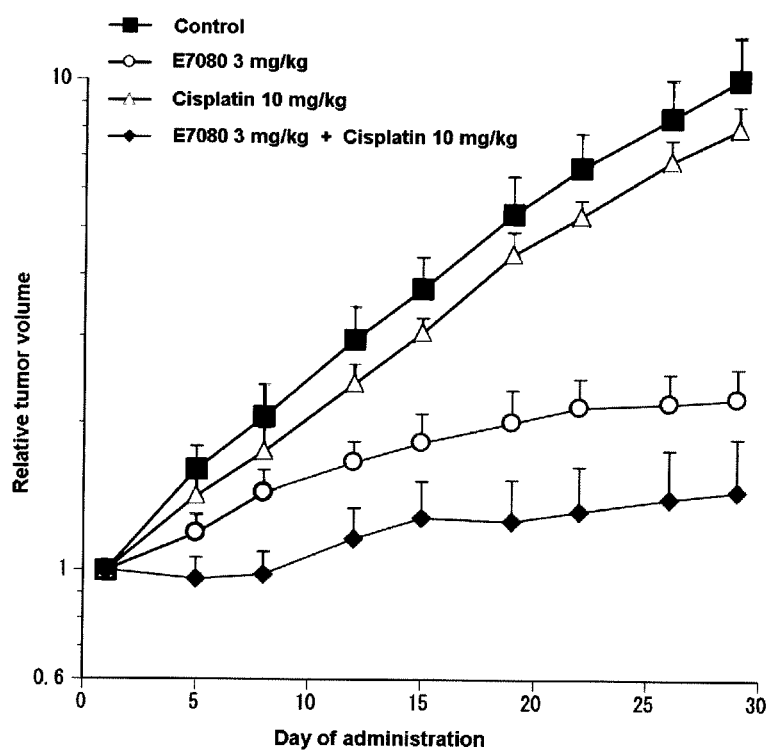
FIG. 1 shows the effect of combination use of E7080 and cisplatin on subcutaneous transplanted (in vivo) models of non-small-cell lung cancer cell lines (A549).

Hereinafter, embodiments of the present invention will be described. The following embodiments are examples provided for illustrating the present invention, and the present invention is not intended to be limited thereto. The present invention may be carried out in various embodiments without departing from the spirit of the invention.

The publications, laid-open patent publications, patent publications and other patent documents cited herein are entirely incorporated herein by reference. The present specification incorporates the content of the specification of U.S. provisional application No. 60/986,641 (filed on 9 Nov., 2007) based on which the present application claims priority.

1. Compound

As used herein, a "halogen atom" refers to a fluorine atom, a chlorine atom, a bromine atom or an iodine atom.

Preferable examples of a "halogen atom" include a fluorine atom and a chlorine atom.

As used herein, a "$C_{1-6}$ alkyl group" refers to a linear or branched alkyl group with a carbon number of 1-6, specific examples including a methyl group, an ethyl group, a 1-propyl group (n-propyl group), a 2-propyl group (i-propyl group), a 2-methyl-1-propyl group (1-butyl group), a 2-methyl-2-propyl group (t-butyl group), a 1-butyl group (n-butyl group), a 2-butyl group (s-butyl group), a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group and a 2,3-dimethyl-2-butyl group.

Preferable examples of a "$C_{1-6}$ alkyl group" include a methyl group, an ethyl group, a 1-propyl group, a 2-propyl group, a 2-methyl-1-propyl group, a 2-methyl-2-propyl group, a 1-butyl group and a 2-butyl group.

As used herein, a "$C_{1-6}$ alkylene group" refers to a divalent group derived from a "$C_{1-6}$ alkyl group" defined above by removing any one hydrogen atom therefrom, specific examples including a methylene group, a 1,2-ethylene group, a 1,1-ethylene group, a 1,3-propylene group, a tetramethylene group, a pentamethylene group and a hexamethylene group.

As used herein, a "$C_{2-6}$ alkenyl group" refers to a linear or branched alkenyl group having one double bond and a carbon number of 2-6, specific examples including an ethenyl group (vinyl group), a 1-propenyl group, a 2-propenyl group (allyl group), a 1-butenyl group, a 2-butenyl group, a 3-butenyl group, a pentenyl group and a hexenyl group.

As used herein, a "$C_{2-6}$ alkynyl group" refers to a linear or branched alkynyl group having one triple bond and a carbon number of 2-6, specific examples including an ethynyl group, a 1-propynyl group, a 2-propynyl group, a 1-butynyl group, a 2-butynyl group, a 3-butynyl group, a pentynyl group and a hexynyl group.

As used herein, a "$C_{3-8}$ cycloalkyl group" refers to a monocyclic or bicyclic saturated aliphatic hydrocarbon group with a carbon number of 3-8, specific examples including a cyclopropyl group, a cyclobutyl group, a cyclopentyl group, a cyclohexyl group, a cycloheptyl group, a cyclooctyl group, a bicyclo[2.1.0]pentyl group, a bicyclo[3.1.0]hexyl group, a bicyclo[2.1.1]hexyl group, a bicyclo[4.1.0]heptyl group, a bicyclo[2.2.1]heptyl group (norbornyl group), a bicyclo[3.3.0]octyl group, a bicyclo[3.2.1]octyl group and a bicyclo[2.2.2]octyl group.

Preferable examples of a "$C_{3-8}$ cycloalkyl group" include a cyclopropyl group, a cyclobutyl group and a cyclopentyl group.

As used herein, a "$C_{6-10}$ aryl group" refers to an aromatic hydrocarbon cyclic group with a carbon number of 6-10, specific examples including a phenyl group, a 1-naphthyl group, a 2-naphthyl group, an indenyl group and an azulenyl group.

A preferable example of a "$C_{6-10}$ aryl group" includes a phenyl group.

As used herein, a "heteroatom" refers to a nitrogen atom, an oxygen atom or a sulfur atom.

As used herein, a "5-10-membered heteroaryl group" refers to an aromatic cyclic group having 5-10 atoms forming the ring and 1-5 heteroatoms included in the atoms forming the ring, specific examples including a furyl group, a thienyl group, a pyrrolyl group, an imidazolyl group, a triazolyl group, a tetrazolyl group, a thiazolyl group, a pyrazolyl group, an oxazolyl group, an isoxazolyl group, an isothiazolyl group, a furazanyl group, a thiadiazolyl group, an oxadiazolyl group, a pyridyl group, a pyrazinyl group, a pyridazinyl group, a pyrimidinyl group, a triazinyl group, a purinyl group, a pteridinyl group, a quinolyl group, an isoquinolyl group, a naphthiridinyl group, a quinoxalinyl group, a cinnolinyl group, a quinazolinyl group, a phthalazinyl group, an imidazopyridyl group, an imidazothiazolyl group, an imidazoxazolyl group, a benzothiazolyl group, a benzoxazolyl group, a benzimidazolyl group, an indolyl group, an isoindolyl group, an indazolyl group, a pyrrolopyridyl group, a thienopyridyl group, a furopyridyl group, a benzothiadiazolyl group, a benzoxadiazolyl group, a pyridopyrimidinyl group, a benzofuryl group, a benzothienyl group and a thienofuryl group.

Preferable examples of a "5-10-membered heteroaryl group" include a furyl group, a thienyl group, a pyrrolyl group, an imidazolyl group, a thiazolyl group, a pyrazolyl group, an oxazolyl group, an isoxazolyl group, an isothiazolyl group, a pyridyl group and a pyrimidinyl group.

As used herein, a "3-10-membered nonaromatic heterocyclic group":
(a) has 3-10 atoms forming the ring;
(b) has 1-2 heteroatoms included in the atoms forming the ring;
(c) may include 1-2 double bonds in the ring;
(d) may include 1-3 carbonyl groups, sulfinyl groups or sulfonyl groups in the ring; and
(e) refers to a nonaromatic monocyclic or bicyclic group, where when a nitrogen atom is included in the atoms forming the ring, the nitrogen atom may have a bond.

Specific examples include an aziridinyl group, an azetidinyl group, a pyrrolidinyl group, a piperidinyl group, an azepanyl group, an azocanyl group, a piperazinyl group, a diazepanyl group, a diazocanyl group, a diazabicyclo[2.2.1]heptyl group, a morpholinyl group, a thiomorpholinyl group, a 1,1-dioxothiomorpholinyl group, an oxiranyl group, an oxetanyl group, a tetrahydrofuryl group, a dioxoranyl group, a tetrahydropyranyl group, a dioxanyl group, a tetrahydrothienyl group, a tetrahydrothiopyranyl group, an oxazolidinyl group and a thiazolidinyl group.

Preferable examples of a "3-10-membered nonaromatic heterocyclic group" include an aziridinyl group, an azetidinyl group, a pyrrolidinyl group, a piperidinyl group, an azepanyl group, a piperazinyl group, a diazepanyl group, a morpholinyl group, a thiomorpholinyl group, a 1,1-dioxothiomorpholinyl group, a tetrahydrofuryl group and a tetrahydropyranyl group.

As used herein, a "$C_{1-6}$ alkoxy group" refers to a group in which an oxygen atom is bound to the terminal of a "$C_{1-6}$ alkyl group" defined above, specific examples including a methoxy group, an ethoxy group, a 1-propoxy group (n-propoxy group), a 2-propoxy group (1-propoxy group), a 2-methyl-1-propoxy group (1-butoxy group), a 2-methyl-2-propoxy group (t-butoxy group), a 1-butoxy group (n-butoxy group), a 2-butoxy group (s-butoxy group), a 1-pentyloxy group, a 2-pentyloxy group, a 3-pentyloxy group, a 2-methyl-1-butoxy group, a 3-methyl-1-butoxy group, a 2-methyl-2-butoxy group, a 3-methyl-2-butoxy group, a 2,2-dimethyl-1-propoxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butoxy group, a 3,3-dimethyl-1-butoxy group, a 2,2-dimethyl-1-butoxy group, a 2-ethyl-1-butoxy group, a 3,3-dimethyl-2-butoxy group and a 2,3-dimethyl-2-butoxy group.

Preferable examples of a "$C_{1-6}$ alkoxy group" include a methoxy group, an ethoxy group, a 1-propoxy group, a 2-propoxy group, a 2-methyl-1-propoxy group, a 2-methyl-2-propoxy group, a 1-butoxy group and a 2-butoxy group.

As used herein, a "$C_{1-6}$ alkylthio group" refers to a group in which a sulfur atom is bound to the terminal of a "$C_{1-6}$ alkyl group" defined above, specific examples including a methylthio group, an ethylthio group, a 1-propylthio group (n-propylthio group), a 2-propylthio group (i-propylthio group), a 2-methyl-1-propylthio group (1-butylthio group), a 2-methyl-2-propylthio group (t-butylthio group), a 1-butylthio group (n-butylthio group), a 2-butylthio group (s-butylthio group), a 1-pentylthio group, a 2-pentylthio group, a 3-pentylthio group, a 2-methyl-1-butylthio group, a 3-methyl-1-butylthio group, a 2-methyl-2-butylthio group, a 3-methyl-2-butylthio group, a 2,2-dimethyl-1-propylthio group, a 1-hexylthio group, a 2-hexylthio group, a 3-hexylthio group, a 2-methyl-1-pentylthio group, a 3-methyl-1-pentylthio group, a 4-methyl-1-pentylthio group, a 2-methyl-2-pentylthio group, a 3-methyl-2-pentylthio group, a 4-methyl-2-pentylthio group, a 2-methyl-3-pentylthio group, a 3-methyl-3-pentylthio group, a 2,3-dimethyl-1-butylthio group, a 3,3-dimethyl-1-butylthio group, a 2,2-dimethyl-1-butylthio group, a 2-ethyl-1-butylthio group, a 3,3-dimethyl-2-butylthio group and a 2,3-dimethyl-2-butylthio group.

Preferable examples of a "$C_{1-6}$ alkylthio group" include a methylthio group, an ethylthio group, a 1-propylthio group (n-propylthio group), a 2-propylthio group (1-propylthio group), a 2-methyl-1-propylthio group (1-butylthio group), a 2-methyl-2-propylthio group (t-butylthio group), a 1-butylthio group (n-butylthio group) and a 2-butylthio group (s-butylthio group).

As used herein, a "$C_{3-8}$ cycloalkoxy group" refers to a group in which an oxygen atom is bound to the terminal of a "$C_{3-8}$ cycloalkyl group" defined above, specific examples including a cyclopropoxy group, a cyclobutoxy group, a cyclopentyloxy group, a cyclohexyloxy group, a cycloheptyloxy group, a cyclooctyloxy group, a bicyclo[2.1.0]pentyloxy group, a bicyclo[3.1.0]hexyloxy group, a bicyclo[2.1.1]hexyloxy group, a bicyclo[4.1.0]heptyloxy group, a bicyclo[2.2.1]heptyloxy group (norbornyloxy group), a bicyclo[3.3.0]octyloxy group, a bicyclo[3.2.1]octyloxy group and a bicyclo[2.2.2]octyloxy group.

Preferable examples of a "$C_{3-8}$ cycloalkoxy group" include a cyclopropoxy group, a cyclobutoxy group and a cyclopentyloxy group.

As used herein, a "mono-$C_{1-6}$ alkylamino group" refers to a group in which one hydrogen atom in an amino group is substituted with a "$C_{1-6}$ alkyl group" defined above, specific examples including a methylamino group, an ethylamino group, a 1-propylamino group (n-propylamino group), a 2-propylamino group (i-propylamino group), a 2-methyl-1-propylamino group (1-butylamino group), a 2-methyl-2-propylamino group (t-butylamino group), a 1-butylamino group (n-butylamino group), a 2-butylamino group (s-butylamino group), a 1-pentylamino group, a 2-pentylamino group, a 3-pentylamino group, a 2-methyl-1-butylamino group, a 3-methyl-1-butylamino group, a 2-methyl-2-butylamino group, a 3-methyl-2-butylamino group, a 2,2-dimethyl-1-propylamino group, a 1-hexylamino group, a 2-hexylamino group, a 3-hexylamino group, a 2-methyl-1-pentylamino group, a 3-methyl-1-pentylamino group, a 4-methyl-1-pentylamino group, a 2-methyl-2-pentylamino group, a 3-methyl-2-pentylamino group, a 4-methyl-2-pentylamino group, a 2-methyl-3-pentylamino group, a 3-methyl-3-pentylamino group, a 2,3-dimethyl-1-butylamino group, a 3,3-dimethyl-1-butylamino group, a 2,2-dimethyl-1-butylamino group, a 2-ethyl-1-butylamino group, a 3,3-dimethyl-2-butylamino group and a 2,3-dimethyl-2-butylamino group.

As used herein, a "di-$C_{1-6}$ alkylamino group" refers to a group in which two hydrogen atoms in an amino group are substituted with identical or different "$C_{1-6}$ alkyl groups" defined above, specific examples including a N,N-dimethylamino group, a N,N-diethylamino group, a N,N-di-n-propylamino group, a N,N-di-1-propylamino group, a N,N-di-n-butylamino group, a N,N-di-1-butylamino group, a N,N-di-s-butylamino group, a N,N-di-t-butylamino group, a N-ethyl-N-methylamino group, a N-n-propyl-N-methylamino group, a N-1-propyl-N-methylamino group, a N-n-butyl-N-methylamino group, a N-1-butyl-N-methylamino group, a N-s-butyl-N-methylamino group and a N-t-butyl-N-methylamino group.

As used herein, a "$C_{2-7}$ acyl group" refers to a carbonyl group bound with a "$C_{1-6}$ alkyl group" defined above, specific examples including an acetyl group, a propionyl group, an isopropionyl group, a butyryl group, an isobutyryl group, a valeryl group, an isovaleryl group and a pivaloyl group.

As used herein, a "$C_{2-7}$ alkoxycarbonyl group" refers to a carbonyl group bound with a "$C_{1-6}$ alkoxy group" defined above, specific examples including a methoxycarbonyl group, an ethoxycarbonyl group, a 1-propyloxycarbonyl group, a 2-propyloxycarbonyl group, a 2-methyl-2-propoxy group and a 2-methyl-2-propoxycarbonyl group.

As used herein, "that may have a substituent (optionally substituted)" means "that may have one or more substituents in any combination at substitutable positions", and specific examples of the substituent include a halogen atom, a hydroxyl group, a thiol group, a nitro group, a cyano group, a formyl group, a carboxyl group, an amino group, a silyl group, a methanesulfonyl group, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a 5-10-membered heteroaryl group, a 3-10-membered nonaromatic heterocyclic group, a $C_{1-6}$ alkoxy group, a $C_{1-6}$ alkylthio group, a $C_{3-8}$ cycloalkoxy group, a mono-$C_{1-6}$ alkylamino group, a di-$C_{1-6}$ alkylamino group, a $C_{2-7}$ acyl group and a $C_{2-7}$ alkoxycarbonyl group. In this case, the $C_{1-6}$ alkyl group, the $C_{2-6}$ alkenyl group, the $C_{2-6}$ alkynyl group, the $C_{3-8}$ cycloalkyl group, the $C_{6-10}$ aryl group, the 5-10-membered heteroaryl group, the 3-10-membered nonaromatic heterocyclic group, the $C_{1-6}$ alkoxy group, the $C_{1-6}$ alkylthio group, the $C_{3-8}$ cycloalkoxy group, the mono-$C_{1-6}$ alkylamino group, the di-$C_{1-6}$ alkylamino group, the $C_{2-7}$ acyl group and the $C_{2-7}$ alkoxycarbonyl group may each independently have 1-3 groups selected from the group consisting of the following substituent groups.

<Substituent Groups>

A halogen atom, a hydroxyl group, a thiol group, a nitro group, a cyano group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5-10-membered heteroaryl group, a 3-10-membered nonaromatic heterocyclic group, a $C_{1-6}$ alkoxy group and a $C_{1-6}$ alkylthio group.

(A) Compound of the Invention

According to the present invention, a compound represented by General Formula (I) is as follows.

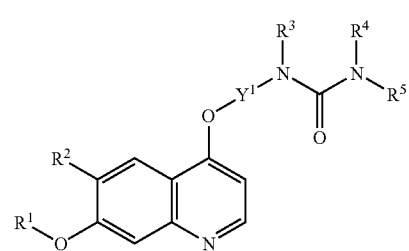

(i) $R^1$ $R^1$ represents a group represented by Formula —$V^1$—$V^2$—$V^3$ (wherein, $V^1$ represents an optionally substituted $C_{1-6}$ alkylene group; $V^2$ represents a single bond, an oxygen atom, a sulfur atom, a carbonyl group, a sulfinyl group, a sulfonyl group, a group represented by Formula —CONR$^6$—, a group represented by Formula —SO$_2$NR$^6$—, a group represented by Formula —NR$^6$SO$_2$—, a group represented by Formula —NR$^6$CO— or a group represented by Formula —NR$^6$— (wherein, R$^6$ represents a hydrogen atom, an optionally substituted $C_{1-6}$ alkyl group or an optionally substituted $C_{3-8}$ cycloalkyl group); $V^3$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group).

A preferable example of $R^1$ includes a $C_{1-6}$ alkyl group provided that $R^1$ may have a substituent selected from a 3-10-membered nonaromatic heterocyclic group, a hydroxyl group, a $C_{1-6}$ alkoxy group, an amino group, a mono-$C_{1-6}$ alkylamino group and a di-$C_{1-6}$ alkylamino group which may have a $C_{1-6}$ alkyl group.

More preferable examples of $R^1$ include a methyl group and a group represented by any one of the following formulae

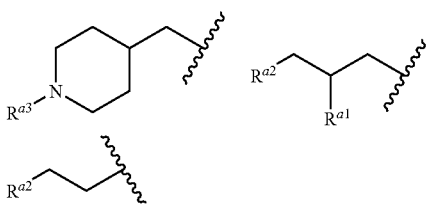

(wherein, $R^{a3}$ represents a methyl group; $R^{a1}$ represents a hydrogen atom or a hydroxyl group; $R^{a2}$ represents a methoxy group, an ethoxy group, a 1-pyrrolidinyl group, a 1-piperidinyl group, a 4-morpholinyl group, a dimethylamino group or a diethylamino group).

Still more preferable examples of $R^1$ include a methyl group and a 2-methoxyethyl group.

(ii) $R^2$ $R^2$ represents a cyano group, an optionally substituted $C_{1-6}$ alkoxy group, a carboxyl group, an optionally substituted $C_{2-7}$ alkoxycarbonyl group or a group represented by Formula —$CONV^{a11}V^{a12}$ (wherein, $V^{a11}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group; $V^{a12}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group, an optionally substituted 3-10-membered nonaromatic heterocyclic group, a hydroxyl group, an optionally substituted $C_{1-6}$ alkoxy group or an optionally substituted $C_{3-8}$ cycloalkoxy group).

Preferable examples of $R^2$ include a cyano group or a group represented by Formula —$CONV^{a11}V^{a12}$ (wherein, $V^{a11}$ and $V^{a12}$ have the same meaning as defined above).

More preferable examples of $R^2$ include a cyano group or a group represented by Formula —$CONHV^{a16}$ (wherein, $V^{a16}$ represents a hydrogen atom, a $C_{1-6}$ alkyl group, a $C_{3-8}$ cycloalkyl group, a $C_{1-6}$ alkoxy group or a $C_{3-8}$ cycloalkoxy group, provided that $V^{a16}$ may have a substituent selected from a halogen atom, a cyano group, a hydroxyl group and a $C_{1-6}$ alkoxy group).

A still more preferable example of $R^2$ includes a group represented by Formula —$CONHV^{a17}$ (wherein, $V^{a17}$ represents a hydrogen atom, a $C_{1-6}$ alkyl group or a $C_{1-6}$ alkoxy group).

The most preferable example of $R^2$ includes a group represented by Formula —$CONHV^{a18}$ (wherein, $V^{a18}$ represents a hydrogen atom, a methyl group or a methoxy group).

(iii) $Y^1$ $Y^1$ represents a group represented by the following formula

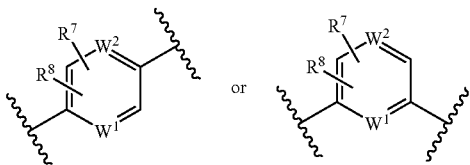

(wherein, $R^7$ and $R^8$ each independently represent a hydrogen atom, a halogen atom, a cyano group, a nitro group, an amino group, an optionally substituted $C_{1-6}$ alkyl group, an optionally substituted $C_{3-8}$ cycloalkyl group, an optionally substituted $C_{1-6}$ alkoxy group, an optionally substituted $C_{1-6}$ alkylthio group, a formyl group, an optionally substituted $C_{2-7}$ acyl group, an optionally substituted $C_{2-7}$ alkoxycarbonyl group or a group represented by Formula —$CONV^{d1}V^{d2}$ (wherein, $V^{d1}$ and $V^{d2}$ each independently represent a hydrogen atom or an optionally substituted $C_{1-6}$ alkyl group);

$W^1$ and $W^2$ each independently represent an optionally substituted carbon atom or nitrogen atom).

A preferable example of $Y^1$ includes a group represented by the following formula

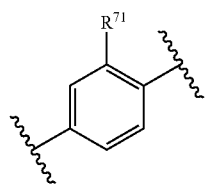

(wherein, $R^{71}$ represents a hydrogen atom or a halogen atom).

(iv) $R^3$ and $R^4$ $R^3$ and $R^4$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{2-7}$ acyl group or an optionally substituted $C_{2-7}$ alkoxycarbonyl group.

A preferable example of $R^3$ and $R^4$ includes a hydrogen atom.

(v) $R^5$ $R^5$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-10}$ aryl group, an optionally substituted 5-10-membered heteroaryl group or an optionally substituted 3-10-membered nonaromatic heterocyclic group.

Preferable examples of $R^5$ include a hydrogen atom, a $C_{1-6}$ alkyl group, a $C_{3-8}$ cycloalkyl group and a $C_{6-10}$ aryl group (provided that $R^5$ may have a substituent selected from a halogen atom and a methanesulfonyl group).

More preferable examples of $R^5$ include a methyl group, an ethyl group and a cyclopropyl group.

Moreover, preferable examples of the compound represented by General Formula (I) include:

N-(4-(6-cyano-7-(2-methoxyethoxy)-4-quinolyl)oxy-2-fluorophenyl)-N'-(4-fluorophenyl)urea;

N-(2-chloro-4-((6-cyano-7-((1-methyl-4-piperidyl)methoxy)-4-quinolyl)oxy)phenyl)-N'-cyclopropylurea;

N-(4-((6-cyano-7-(((2R)-3-(diethylamino)-2-hydroxypropyl)oxy)-4-quinolyl)oxy)phenyl)-N'-(4-fluorophenyl)urea;

N-(4-((6-cyano-7-(((2R)-2-hydroxy-3-(1-pyrrolidino)propyl)oxy)-4-quinolyl)oxy)phenyl)-N'-(4-fluorophenyl)urea;

4-(3-chloro-4-(cyclopropylaminocarbonyl)aminophenoxy)-7-methoxy-6-quinolinecarboxamide;

4-(3-chloro-4-(cyclopropylaminocarbonyl)aminophenoxy)-7-(2-methoxyethoxy)-6-quinolinecarboxamide;

N6-cyclopropyl-4-(3-chloro-4-(((cyclopropylamino)carbonyl)amino)phenoxy)-7-methoxy-6-quinolinecarboxamide;

N6-(2-methoxyethyl)-4-(3-chloro-4-(((cyclopropylamino)carbonyl)amino)phenoxy)-7-methoxy-6-quinolinecarboxamide;
N6-(2-fluoroethyl)-4-(3-chloro-4-(((cyclopropylamino)carbonyl)amino)phenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
N6-methyl-4-(3-chloro-4-(((cyclopropylamino)carbonyl)amino)phenoxy)-7-methoxy-6-quinolinecarboxamide;
N6-ethyl-4-(3-chloro-4-(((cyclopropylamino)carbonyl)amino)phenoxy)-7-methoxy-6-quinolinecarboxamide;
4-(3-fluoro-4-(cyclopropylaminocarbonyl)aminophenoxy)-7-(2-methoxyethoxy)-6-quinolinecarboxamide;
4-(3-chloro-4-(cyclopropylaminocarbonyl)aminophenoxy)-7-(2-hydroxyethoxy)-6-quinolinecarboxamide;
4-(3-chloro-4-(cyclopropylaminocarbonyl)aminophenoxy)-7-((2S)-2,3-dihydroxypropyl)oxy-6-quinolinecarboxamide;
4-(3-chloro-4-(methylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-ethoxyethoxy)-6-quinolinecarboxamide;
4-(4-((cyclopropylamino)carbonyl)aminophenoxy)-7-(2-methoxyethoxy)-6-quinolinecarboxamide;
N-(2-fluoro-4-((6-carbamoyl-7-methoxy-4-quinolyl)oxy)phenyl)-N'-cyclopropylurea;
N6-(2-hydroxyethyl)-4-(3-chloro-4-(((cyclopropylamino)carbonyl)amino)phenoxy)-7-methoxy-6-quinolinecarboxamide;
4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl)aminophenoxy)-7-methoxy-6-quinolinecarboxamide;
N6-methyl-4-(3-chloro-4-(((cyclopropylamino)carbonyl)amino)phenoxy)-7-(2-methoxyethoxy)-6-quinolinecarboxamide;
N6-methyl-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino)phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((2R)-3-diethylamino-2-hydroxypropoxy)-6-quinolinecarboxamide;
N6-methyl-4-(3-chloro-4-(((ethylamino)carbonyl)amino)phenoxy)-7-((2R)-3-diethylamino-2-hydroxypropoxy)-6-quinolinecarboxamide;
N6-methyl-4-(3-chloro-4-(((methylamino)carbonyl)amino)phenoxy)-7-((2R)-2-hydroxy-3-(1-pyrrolidino)propoxy)-6-quinolinecarboxamide;
N6-methyl-4-(3-chloro-4-(((ethylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((1-methyl-4-piperidyl)methoxy)-6-quinolinecarboxamide;
N6-methyl-4-(3-chloro-4-(((ethylamino) carbonyl)amino)phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropylurea;
N-(4-(6-cyano-7-(3-(4-morpholino)propoxy)-4-quinolyl)oxyphenyl)-N'-(3-(methylsulfonyl)phenyl)urea;
4-(4-((cyclopropylamino)carbonyl)aminophenoxy)-7-methoxy-6-quinolinecarboxamide;
4-(3-fluoro-4-((2-fluoroethylamino)carbonyl)aminophenoxy)-7-methoxy-6-quinolinecarboxamide;
N6-(2-ethoxyethyl)-4-(3-chloro-4-(((methylamino)carbonyl)amino)phenoxy)-7-methoxy-6-quinolinecarboxamide;
4-(4-(3-ethylureido)-3-fluoro-phenoxy)-7-methoxyquinoline-6-carboxylic acid (2-cyanoethyl)amide; and
N-(4-(6-(2-cyanoethyl)carbamoyl-7-methoxy-4-quinolyl)oxy-2-fluorophenyl)-N'-cyclopropylurea.

More preferable examples of the compound represented by General Formula (I) include:
4-(3-chloro-4-(cyclopropylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
4-(3-chloro-4-(methylaminocarbonyl)aminophenoxy)-7-methoxy-6-quinolinecarboxamide; and
N6-methoxy-4-(3-chloro-4-(((ethylamino)carbonyl)amino)phenoxy)-7-methoxy-6-quinolinecarboxamide.

A still more preferable example of the compound represented by General Formula (I) includes 4-(3-chloro-4-(cyclopropylaminocarbonyl)aminophenoxy)-7-methoxy-6-quinolinecarboxamide (see Formula (II)).

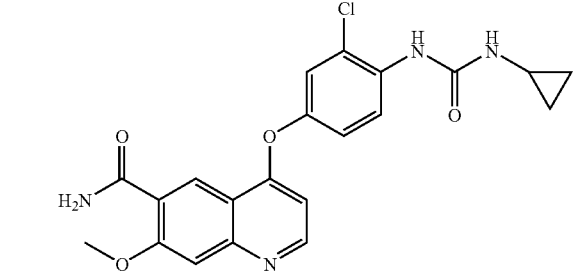

(II)

The most preferable example of the compound represented by General Formula (I), a pharmacologically acceptable salt thereof or a solvate thereof includes methanesulfonate of 4-(3-chloro-4-(cyclopropylaminocarbonyl)aminophenoxy)-7-methoxy-6-quinolinecarboxamide.

A compound represented by General formula (I) may be produced by a known method such as methods described in International Publication Nos. 02/32872 (WO02/32872) and 2005/063713 (WO2005/063713).

(B) Anti-Tumor Platinum Complex

According to the present invention, an anti-tumor platinum complex (a platinum complex having anti-tumor effect) is, for example, cisplatin, carboplatin, nedaplatin, zeniplatin, enloplatin, lobaplatin, ormaplatin, loboplatin, sebriplatin, oxaliplatin, miboplatin or spiroplatin, preferably cisplatin or carboplatin, and particularly preferably carboplatin.

These anti-tumor platinum complexes may be produced according to a known method.

These anti-tumor platinum complexes are also available by purchasing commercially-available products. For example, cisplatin is commercially available under the trade names of Randa (Registered Trademark) from Nippon Kayaku Co., Ltd., Platosin (Registered Trademark) from Pfizer Japan Inc., Cisplamerck (Registered Trademark) from Merck Japan and Briplatin (Registered Trademark) from Bristol-Myers Squibb. Carboplatin is commercially available under the trade names of Paraplatin (Registered Trademark) from Bristol-Myers Squibb and Carbomerck (Registered Trademark) from Merck Japan. Nedaplatin is commercially available under a trade name of Aqupla (Registered Trademark) from Shionogi & Co., Ltd. Oxaliplatin is commercially available under the trade names of Elplat (Registered Trademark) or Eloxatin (Registered Trademark) from Yakult Honsha, Co., Ltd. Miboplatin is commercially available as miboplatin hydrochloride or under a trade name of Lobaplatin (Registered Trademark) from Chugai Pharmaceutical Co., Ltd.

According to the present invention, the compound represented by General Formula (I), and/or the anti-tumor platinum complex may form a pharmacologically acceptable salt with acid or base. The compound of the invention comprises these pharmacologically acceptable salts. Examples of salts formed with acids include inorganic acid salts such as hydrochloride salts, hydrobromate salts, sulfate salts and phosphate salts, and organic acid salts such as formic acid, acetic acid, lactic acid, succinic acid, fumaric acid, maleic acid, citric acid, tartaric acid, stearic acid, benzoic acid, methanesulfonic acid, benzenesulfonic acid, p-toluenesulfonic acid and trifluoroacetic acid. Examples of salts formed with bases include alkali metal salts such as sodium salt and potassium salt, alkaline earth metal salts such as calcium salt and magnesium salt, organic base salts such as trimethylamine, triethylamine, pyridine, picoline, dicyclohexylamine, N,N'-dibenzyl ethylenediamine, arginine and lysine and ammonium salts.

Furthermore, according to the present invention, the compound represented by General Formula (I) and/or an anti-tumor platinum complex also comprise, if any, a solvate or an optical isomer thereof. Examples of solvates include hydrates and nonhydrates, preferably hydrates. Examples of solvents include water, alcohols (for example, methanol, ethanol and n-propanol) and dimethylformamide.

Moreover, according to the present invention, the compound of the invention and/or an anti-tumor platinum complex may be crystalline or amorphous. If a crystalline polymorph is present, it may exist as one type of any crystalline or mixture thereof.

According to the present invention, the compound of the invention and/or an anti-tumor platinum complex also comprises compounds that generate the compound of the invention and/or an anti-tumor platinum complex by undergoing metabolism such as oxidation, reduction and hydrolysis in vivo.

2. Pharmaceutical Composition, Kit and Method for Treating Cancer

The present invention relates to a pharmaceutical composition, a kit, a method for treating cancer and the like, characterized in that a compound represented by General Formula (I), a pharmacologically acceptable salt thereof or a solvate thereof (compound of the invention) is combined with an anti-tumor platinum complex.

According to the present invention, the term "combination" refers to a combination of compounds for combination use, and includes both modes where separate substances are used in combination upon administration or where they are provided as a mixture (compounding agent). According to the present invention, "combination use" does not only refer to exactly the same administration timing of the compound of the invention and an anti-tumor platinum complex. As long as the compound of the invention and the anti-tumor platinum complex are administered during a single administration schedule, both simultaneous and separate administrations thereof can be referred to as "combination use" When they are administered separately, the anti-tumor platinum complex may be administered after the compound of the invention. Alternatively, the compound of the invention may be administered after the anti-tumor platinum complex.

A pharmaceutical composition and/or a kit of the invention is useful as a pharmaceutical composition and/or a kit for treating cancer.

A pharmaceutical composition and/or a kit of the invention may be used as a therapeutic agent for cancer.

According to the present invention, a therapeutic agent for cancer comprises those that contain an anti-tumor drug, a drug for improving prognosis of cancer, a drug for preventing cancer recurrence, and an antimetastatic drug or the like. Pleferably, an anti-tumor drug can be used.

The effect of cancer treatment can be confirmed by observation of X-ray pictures, CT or the like, histopathologic diagnosis by biopsy, tumor marker value or the like.

A pharmaceutical composition and/or a kit of the invention may be administered to mammals (e.g., human, rat, rabbit, sheep, pig, cattle, cat, dog or monkey).

Examples of the types of cancers targeted by the therapeutic agent for cancer include, but not limited to, brain tumors (including hypophysial adenoma and glioma), head and neck cancer, cervical cancer, jaw cancer, maxillary cancer, submandibular gland cancer, oral cancers (including tongue cancer, mouth floor cancer, gingival cancer, buccal mucosa cancer and hard palate cancer), salivary gland cancer, sublingual gland cancer, parotid gland cancer, nasal cavity cancer, paranasal sinus cancers (including maxillary sinus cancer, frontal sinus cancer, ethmoid sinus cancer and sphenoid sinus cancer), pharyngeal cancers (including supraglottic cancer, glottic cancer and subglottic cancer), esophageal cancer, lung cancers (including bronchogenic cancer, non-small-cell lung cancers (including lung adenocarcinoma, squamous cell carcinoma and large cell lung cancer), small cell lung cancers (including oat cell (lymphoid) and intermediate cell types) and mixed small/large cell lung cancers), breast cancer, pancreas cancers (including pancreatic duct cancer), gastric cancers (including scirrhous gastric cancer and undifferentiated gastric cancer), biliary tract cancers (including bile duct cancer and gallbladder cancer), small intestinal or duodenal cancer, colorectal cancers (including colon cancer, rectal cancer, cecal cancer, sigmoid colon cancer, ascending colon cancer, transverse colon cancer and descending colon cancer), bladder cancer, renal cancers (including renal cell cancer), hepatic cancers (including hepatocellular cancer and intrahepatic bile duct cancer), prostate cancer, uterine cancers (including uterine cervix cancer and uterine body cancer), ovarian cancer, thyroid gland cancer, pharyngeal cancers (including nasopharyngeal cancer, oropharyngeal cancer and hypopharyngeal cancer), sarcomas (e.g., osteosarcoma, chondrosarcoma, Kaposi's sarcoma, myosarcoma, angiosarcoma, fibrosarcoma, etc.), malignant lymphomas (including Hodgkin's lymphoma and non-Hodgkin's lymphoma), leukemias (e.g., chronic myelocytic leukemia (CML), acute myelocytic leukemia (AML), chronic lymphocytic leukemia (CLL), acute lymphocytic leukemia (ALL), lymphoma, multiple myeloma (MM) and myelodysplastic syndrome), skin cancers (basal cell cancer, squamous cell carcinoma, malignant melanoma, mycosis fungoides, Sezary's syndrome, solar keratosis, Bowen's disease and Paget's disease) and melanoma.

The pharmaceutical composition and/or the kit of the invention may be administered orally or parenterally. Upon use of the pharmaceutical composition and/or the kit of the invention, the dosage of the compound of the invention, differs depending on the degree of the symptom, age, sex, weight and sensitivity difference of the patient, administration mode, administration period, administration interval, nature, prescription and type of the pharmaceutical formulation and the type of the active ingredient. Usually, but without limitation, the dosage is 0.1-1000 mg/day, preferably 0.5-100 mg/day and more preferably 1-30 mg/day for an adult (weight 60 kg), which may be administered usually once to three times a day.

An anti-tumor platinum complex may be administered according to known clinical practice. The dosage and dosing schedule may be altered according to a specific symptom or all symptoms of the patient's disease. The dosage may appropriately be reduced according to age, symptoms or incidence of side effects. Upon use of the pharmaceutical composition and/or the kit of the invention, an anti-tumor platinum complex may usually, but not limited, be administered for 10-2000 mg/m$^2$/day, preferably 50-1000 mg/m$^2$/day and more preferably 100-500 mg/m$^2$/day for an adult, which may be administered usually once to three times a day. The dosage needs to be reduced if undue toxicity occurs in the patient. The dosage and dosing schedule may be altered when one or more additional chemotherapeutic agents are used in addition to the combination therapy of the invention. The dosing schedule may be determined by the physician in charge of the treatment of the specific patient.

The amount of the compound of the invention used is not particularly limited, and differs depending on the individual combination with the anti-tumor platinum complex. For example, the amount of the compound of the invention is about 0.0001-10000 times (weight ratio), more preferably about 0.001-1000 times (weight ratio) of the amount of the anti-tumor platinum complex.

More specifically, when the compound of the invention is combined with cisplatin, the dosage of the compound of the invention is not particularly limited and may be administered, for example, for 0.1-1000 mg/day, preferably 0.5-100 mg/day and more preferably 1-30 mg/day for an adult (60 kg) and cisplatin may be administered for 10-2000 mg/m$^2$/day, preferably 50-1000 mg/m$^2$/day and more preferably 100-500 mg/m$^2$/day for an adult (60 kg) while the dosage of the compound of the invention is set to about 0.0001-10000 times (weight ratio), more preferably about 0.001-1000 times (weight ratio) of that of cisplatin.

Furthermore, when the compound of the invention is combined with carboplatin, the dosage of the compound of the invention is not particularly limited and may be administered, for example, for 0.1-1000 mg/day, preferably 0.5-100 mg/day and more preferably 1-30 mg/day for an adult (60 kg) and carboplatin may be administered for 10-2000 mg/m$^2$/day, preferably 50-1000 mg/m$^2$/day and more preferably 100-500 mg/m$^2$/day for an adult (60 kg) while the dosage of the compound of the invention is set to about 0.0001-10000 times (weight ratio), more preferably about 0.001-1000 times (weight ratio) of that of carboplatin.

The pharmaceutical composition of the invention may be made into a solid oral formulation, an injection or the like.

Furthermore, the compound of the invention and the anti-tumor platinum complex included in the kit of the invention may each be made into a solid oral formulation, an injection or the like.

The form of the formulation included in the kit of the invention is not particularly limited as long as it contains the compound of the invention and/or the anti-tumor platinum complex.

In order to prepare a solid oral formulation, the principal agent may be added with an excipient, and if necessary, a binder, a disintegrant, a lubricant, a colorant, a flavoring agent or the like, and then made into a tablet, a coated tablet, granule, subtle granule, powder, a capsule or the like according to a conventional method.

Examples of excipients used include lactose, cornstarch, sucrose, glucose, sorbit, crystalline cellulose and silicon dioxide; examples of binders used include polyvinyl alcohol, ethyl cellulose methyl cellulose, gum arabic, hydroxypropyl cellulose and hydroxypropylmethyl cellulose; examples of lubricants include magnesium stearate, talc and silica; examples of colorants include those that are allowed to be added to pharmaceutical preparations; examples of flavoring agents include cocoa powder, menthol, aromatic acid, peppermint oil, camphor and cinnamon powder. Of course, if necessary, these tablets and granule may be coated appropriately with sugar coating, gelatin coating or else.

When an injection is to be prepared, if necessary, the principal agent may be added with a pH adjuster, a buffer, a suspending agent, a solubilizing aid, a stabilizer, an isotonizing agent, a preservative or the like, and may be made into an injectable form for an intravenous, subcutaneous or intramuscular injection by a conventional technique. In this case, if necessary, it may be prepared into a lyophilized form by a conventional technique.

Examples of suspending agents may include methyl cellulose, Polysorbate 80, hydroxyethyl cellulose, gum arabic, powdered tragacanth, sodium carboxy methyl cellulose and polyoxyethylene sorbitan monolaurate.

Examples of solubilizing aids may include polyoxyethylene hydrogenated castor oil, Polysorbate 80, nicotine acid amide, polyoxyethylene sorbitan monolaurate, macrogol, and ethyl ester of castor oil fatty acid.

Examples of stabilizers may include sodium sulfite and sodium metasulfite; and examples of preservatives may include methyl paraoxybenzoate, ethyl paraoxybenzoate, sorbic acid, phenol, cresol and chlorocresol.

In the kit of the invention, the compound of the invention or a formulation containing the compound of the invention may be mixed with a formulation containing the anti-tumor platinum complex, or they may be kept separately and packed together. The order of administrations of the above formulations is not particularly limited, and they may be administered simultaneously or one after the other.

In addition to the compound of the invention and the anti-tumor platinum complex, the pharmaceutical composition and/or the kit of the invention can also comprise a packaging container, an instruction, a package insert or the like. The packaging container, the instruction, the package insert or the like may be printed with description of a combination for using the substances in combination, and description of usage and dose for using separate substances in combination upon administration or for use of them as a mixture. The usage and dose may be described by referring to the related description above.

The kit of the invention may comprise. (a) at least one selected from the group consisting of a packaging container, an instruction and a package insert describing combination use of the compound of the invention with the anti-tumor platinum complex; and (b) a pharmaceutical composition comprising the compound of the invention. This kit is useful for treating cancer. The pharmaceutical composition comprising the compound of the invention is useful for treating cancer. The packaging container, the instruction, the package insert of the like may be printed with description for using the compounds in combination, and description of usage and dose for using separate substances in combination upon administration or for use of them as a mixture. The usage and dose may be described by referring to the related description above.

The present invention also comprises use of a compound of the invention for producing a pharmaceutical composition in combination with an anti-tumor platinum complex. According to the use of the invention, the pharmaceutical composition is useful for treating cancer.

The present invention also comprises a compound of the invention for a pharmaceutical composition in combination with an anti-tumor platinum complex. The pharmaceutical composition is useful for treating cancer. The present invention also comprises a compound of the invention for preventing or treating cancer in combination with an anti-tumor platinum complex. The route and the method for administering the compound of the invention and the anti-tumor platinum complex are not particularly limited but reference may be made to the description of the pharmaceutical composition and/or kit of the invention above.

The present invention also comprises a method for preventing or treating cancer comprising simultaneously or separately administering effective amounts of a compound of the invention and an anti-tumor platinum complex to a patient. According to the method of the invention for preventing or treating cancer, the route and the method for administering the compound of the invention and the anti-tumor platinum complex are not particularly limited but reference may be made to the description of the pharmaceutical composition and/or kit of the invention above.

The present invention also comprises a pharmaceutical composition comprising a compound of the invention which is simultaneously or separately administered with an anti-tumor platinum complex to a patient. For the pharmaceutical composition of the invention, the route and the method for administering the compound of the invention and the anti-tumor platinum complex are not particularly limited but reference may be made to the description of the pharmaceutical composition and/or kit of the invention above.

EXAMPLES

Hereinafter, the present invention will be illustrated by way of specific examples, although the invention should not be limited thereto.

Example 1

Combination Use of E7080 and Cisplatin in Subcutaneous Transplanted Models (In Vivo) of Non-Small-Cell Lung Cancer Cell Line (A549)

Human non-small-cell lung cancer cell line A549 (purchased from Dainippon Sumitomo Pharma Co., Ltd) was cultured in RPMI1640 (containing 10% FBS) in a 5% carbon dioxide gas incubator at 37° C. to about 80% confluence, and then the cells were collected with trypsin-EDTA. A $1\times10^8$ cells/mL suspension was prepared with a phosphate buffer, which was further added with matrigel matrix (purchased from Becton, Dickinson and Co.) to give a $5\times10^7$ cells/mL suspension, and each 0.2 mL of the resulting cell suspension was subcutaneously transplanted to a nude mouse at the side of its body. Eleven days after the transplantation, 4-(3-chloro-4-(cyclopropylaminocarbonyl)aminophenoxy)-7-methoxy-6-quinolinecarboxamide (hereinafter, also referred to as "E7080") was orally administered for 3, 10 or 30 mg/kg, once a day for four weeks, while 10 mg/kg of cisplatin was administered into the tail vein once a day. The major and minor axes of tumors were measured with Digimatic caliper (Mitsutoyo Corporation), and tumor volumes and relative tumor volumes were calculated according to the following formulae:

Tumor Volume (TV)=Major axis of tumor(mm)×(Minor axis of tumor)$^2$(mm$^2$)/2

Relative Tumor Volume (RTV)=Tumor volume on measurement day/Tumor volume on the first administration day.

Synergistic effect was determined to be present in the combination group when a statistically significant (p<0.05) interaction was observed in two-way ANOVA analysis. In addition, even if synergistic effect was not observed, additive effect was determined to be present when higher anti-tumor effect than that obtained upon administration of E7080 or cisplatin alone was observed.

Figure 2:
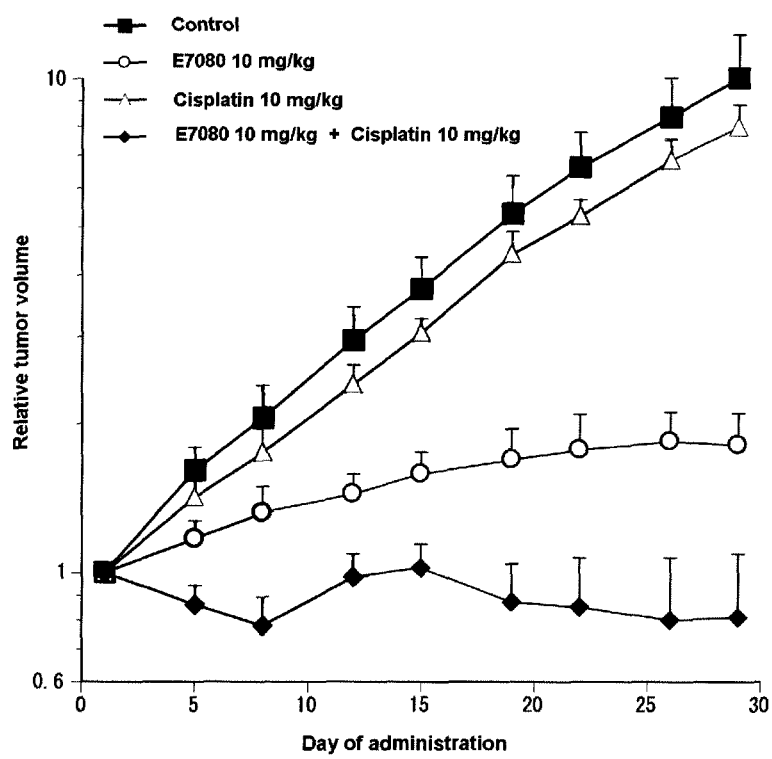
FIG. 2 shows the effect of combination use of E7080 and cisplatin on subcutaneous transplanted (in vivo) models of non-small-cell lung cancer cell lines (A549).
Figure 3:
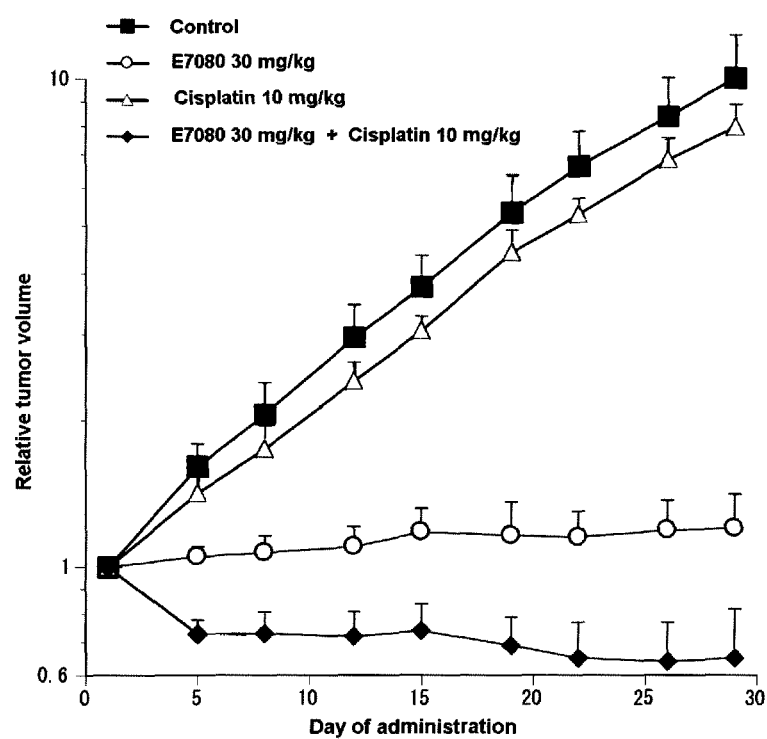
FIG. 3 shows the effect of combination use of E7080 and cisplatin on subcutaneous transplanted (in vivo) models of non-small-cell lung cancer cell lines (A549).

As a result, E7080 showed additive or synergistic effect when used in combination with cisplatin, and their combination use showed a superior anti-tumor effect as compared with those obtained with E7080 or cisplatin alone (Tables 1, 2 and 3, and FIGS. 1, 2 and 3).

TABLE 1

| Administered compound | Relative tumor volume on Day 29 Average ± standard deviation | Two-way ANOVA |
|---|---|---|
| Control (untreated) | 10.07 ± 2.22 | |
| E7080 3 mg/kg | 2.24 ± 0.34 | |
| Cisplatin 10 mg/kg | 7.99 ± 0.88 | |
| E7080 3 mg/kg + Cisplatin 10 mg/kg | 1.45 ± 0.41 | p = 0.142 Additive effect |

TABLE 2

| Administered compound | Relative tumor volume on Day 29 Average ± standard deviation | Two-way ANOVA |
|---|---|---|
| Control (untreated) | 10.07 ± 2.22 | |
| E7080 10 mg/kg | 1.81 ± 0.29 | |
| Cisplatin 10 mg/kg | 7.99 ± 0.88 | |
| E7080 10 mg/kg + Cisplatin 10 mg/kg | 0.81 ± 0.28 | p = 0.00205 Synergistic effect |

TABLE 3

| Administered compound | Relative tumor volume on Day 29 Average ± standard deviation | Two-way ANOVA |
|---|---|---|
| Control (untreated) | 10.07 ± 2.22 | |
| E7080 30 mg/kg | 1.20 ± 0.21 | |
| Cisplatin 10 mg/kg | 7.99 ± 0.88 | |
| E7080 30 mg/kg + Cisplatin 10 mg/kg | 0.65 ± 0.17 | p = 0.0272 Synergistic effect |

Tables 1, 2 and 3 show anti-tumor effects obtained by the use of E7080 alone, the use of cisplatin alone and the combination use of E7080 and cisplatin in subcutaneous transplanted A549 models. The first day of administration was considered Day 1.

According to the obtained results, the combination of E7080 and cisplatin can provide a pharmaceutical composition and a kit that show a remarkable anti-tumor activity, which may be used for treating cancer.

Example 2

Combination Use of E7080 and Carboplatin in Subcutaneous Transplanted Models (In Vivo) of Non-Small-Cell Lung Cancer Cell Line (A549)

Human non-small-cell lung cancer cell line A549 (purchased from Dainippon Sumitomo Pharma Co., Ltd) was cultured in RPMI1640 (containing 10% FBS) in a 5% carbon dioxide gas incubator at 37° C. to about 80% confluence, and then the cells were collected with trypsin-EDTA. A $1 \times 10^8$ cells/mL suspension was prepared with a phosphate buffer, which was further added with matrigel matrix (purchased from Becton, Dickinson and Co.) to give a $5 \times 10^7$ cells/mL suspension, and each 0.2 mL of the resulting cell suspension was subcutaneously transplanted to a nude mouse at the side of its body. Eleven days after the transplantation, 4-(3-chloro-4-(cyclopropylaminocarbonyl)aminophenoxy)-7-methoxy-6-quinolinecarboxamide (E7080) was orally administered for 3 or 10 mg/kg, once a day for four weeks, while 100 mg/kg of carboplatin was administered into the tail vein on the first day. The major and minor axes of tumors were measured with Digimatic caliper (Mitsutoyo Corporation), and tumor volumes and relative tumor volumes were calculated according to the following formulae:

Tumor Volume (TV)=Major axis of tumor(mm)×(Minor axis of tumor)$^2$(mm$^2$)/2

Relative Tumor Volume (RTV)=Tumor volume on measurement day/Tumor volume on the first administration day.

Synergistic effect was determined to be present in the combination group when a statistically significant (p<0.05) interaction was observed in two-way ANOVA analysis. In addition, even if synergistic effect was not observed, additive effect was determined to be present when higher anti-tumor effect than that obtained upon administration of E7080 or carboplatin alone was observed.

Figure 4:
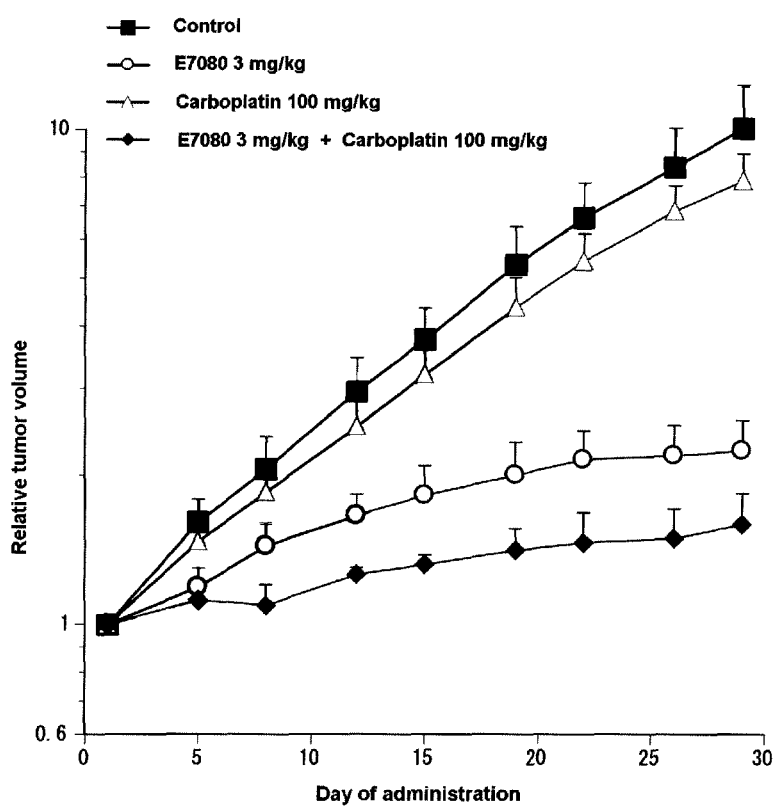
FIG. 4 shows the effect of combination use of E7080 and carboplatin on subcutaneous transplanted (in vivo) models of non-small-cell lung cancer cell lines (A549).
Figure 5:
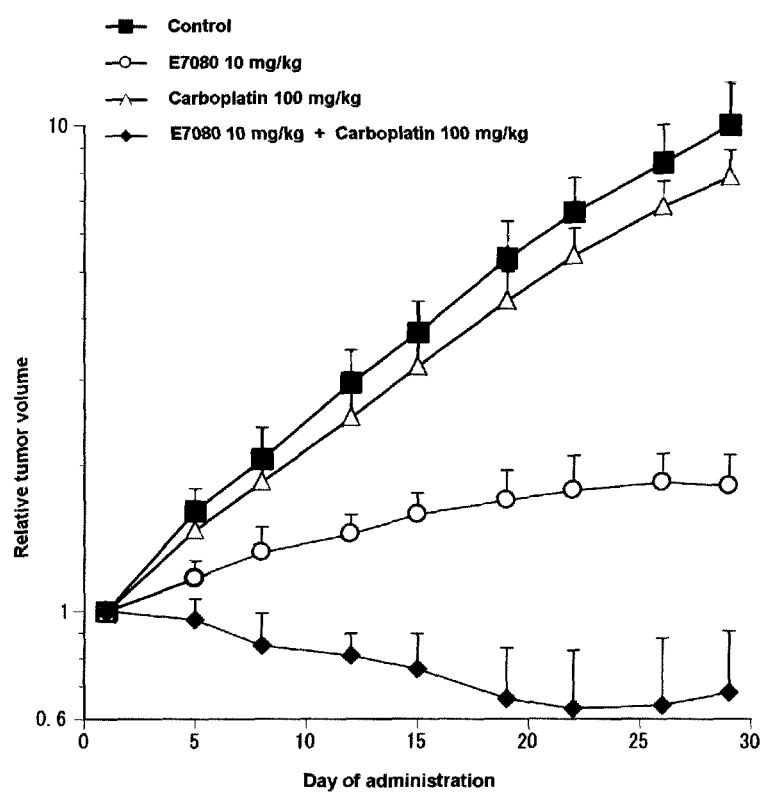
FIG. 5 shows the effect of combination use of E7080 and carboplatin on subcutaneous transplanted (in vivo) models of non-small-cell lung cancer cell lines (A549).

As a result, E7080 showed additive or synergistic effect when used in combination with carboplatin, and their combination use showed a superior anti-tumor effect as compared with those obtained with E7080 or carboplatin alone (Tables 4 and 5, and FIGS. 4 and 5).

TABLE 4

| Administered compound | Relative tumor volume on Day 29 Average ± standard deviation | Two-way ANOVA |
|---|---|---|
| Control (untreated) | 10.07 ± 2.22 | |
| E7080 3 mg/kg | 2.24 ± 0.34 | |
| Carboplatin 100 mg/kg | 7.87 ± 1.05 | |
| E7080 3 mg/kg + Carboplatin 100 mg/kg | 1.59 ± 0.25 | p = 0.417 Additive effect |

TABLE 5

| Administered compound | Relative tumor volume on Day 29 Average ± standard deviation | Two-way ANOVA |
|---|---|---|
| Control (untreated) | 10.07 ± 2.22 | |
| E7080 10 mg/kg | 1.81 ± 0.29 | |
| Carboplatin 100 mg/kg | 7.87 ± 1.05 | |
| E7080 10 mg/kg + Carboplatin 100 mg/kg | 0.68 ± 0.23 | p = 0.000715 Synergistic effect |

Tables 4 and 5 show anti-tumor effects obtained by the use of E7080 alone, the use of carboplatin alone and the combination use of E7080 and carboplatin in subcutaneous transplanted A549 models. The first day of administration was considered Day 1.

According to the obtained results, the combination of E7080 and carboplatin can provide a pharmaceutical composition and a kit that show a remarkable anti-tumor activity, which may be used for treating cancer, Reference Example Hereinafter, a method for producing a formulation of one of the compounds represented by General Formula (I), i.e., 4-(3-chloro-4-(cyclopropylaminocarbonyliaminophenoxy)-7-methoxy-6-quinolinecarboxamide, will be described as a reference example.

(Production of Pharmaceutical Composition)
(1) 1 mg Tablet 24 g of crystal (C) of methanesulfonate of 4-(3-chloro-4-(cyclopropylaminocarbonyl)aminophenoxy)-7-methoxy-6-quinolinecarboxamide (hereinafter, also referred to as "crystal (C)", which was produced according to the method described in Example 7 of WO2005/063713) and 192 g of light anhydrous silicic acid (antigelling agent sold under the trade name of AEROSIL (Registered Trademark) 200, Nippon Aerosil Co., Ltd.) were mixed with 20 L Super Mixer, and then 1236 g of D-mannitol (excipient, Towa-Kasei Co., Ltd.), 720 g of crystalline cellulose (excipient sold under the trade name of Avicel PH101, Asahi Kasei Corporation) and 72 g of hydroxypropylcellulose (binder sold under the trade name of HPC-L, Nippon Soda Co., Ltd.) were further added and mixed together. Subsequently, a suitable amount of anhydrous ethanol was added to obtain a granulated body containing crystal (C). This granulated body was dried in a rack dryer (60° C.), and then size-regulated using PowerMILL to obtain granules. Together with the granules, 120 g of croscarmellose sodium (disintegrant sold under the trade name of Ac-Di-Sol, FMC International Inc.) and 36 g of sodium stearyl fumarate (lubricant, JRS Pharma LP) were placed and mixed together in a 20 L tumbler mixer, and molded with a tablet machine to obtain tablets with a total mass of 100 mg per tablet. Furthermore, the tablets were coated using aqueous 10% Opadry yellow (OPADRY 03F42069 YELLOW, Colorcon Japan) solution as a coating solution with a tablet coating machine, thereby obtaining coated tablets with a total mass of 105 mg per tablet.

(2) 10 mg Tablet

Sixty grams of crystal (C) and 192 g of light anhydrous silicic acid (antigelling agent sold under the trade name of AEROSIL (Registered Trademark) 200, Nippon Aerosil Co., Ltd.) were mixed with 20 L Super Mixer, and then 1200 g of D-mannitol (excipient, Towa-Kasei Co., Ltd.), 720 g of crystalline cellulose (excipient sold under the trade name of Avicel PH101, Asahi Kasei Corporation) and 72 g of hydroxypropylcellulose (binder sold under the trade name of HPC- L, Nippon Soda Co., Ltd.) were further added and mixed together. Subsequently, a suitable amount of anhydrous ethanol was added to obtain a granulated body containing crystal (C). This granulated body was dried in a rack dryer (60° C.), and then size-regulated using PowerMILL to obtain granules. Together with the granules, 120 g of croscarmellose sodium (disintegrant sold under the trade name of Ac-Di-Sol, FMC International Inc.) and 36 g of sodium stearyl fumarate (lubricant, JRS Pharma LP) were placed and mixed together in a 20 L tumbler mixer, and molded with a tablet machine to obtain tablets with a total mass of 400 mg per tablet. Furthermore, the tablets were coated using aqueous 10% Opadry yellow (OPADRY 03F42069 YELLOW, Colorcon Japan) solution as a coating solution with a tablet coating machine, thereby obtaining coated tablets with a total mass of 411 mg per tablet.

(3) 100 mg Tablet 31.4 g of crystal (C) and 4 g of light anhydrous silicic acid (antigelling agent sold under the trade name of AEROSEL (Registered Trademark) 200, Nippon Aerosil Co., Ltd.) were mixed with 1 L Super Mixer, and then 40.1 g of anhydrous calcium hydrogen phosphate (excipient, Kyowa Chemical Industry Co., Ltd.), 10 g of low substituted hydroxypropylcellulose (binder sold under the trade name of L-HPC (LH-21), Shin-Etsu Chemical Co., Ltd.) and 3 g of hydroxypropylcellulose (binder sold under the trade name of HPC-L, Nippon Soda Co., Ltd.) were further added and mixed together.

Subsequently, a suitable amount of anhydrous ethanol was added to obtain a granulated body containing crystal (C). This granulated body was dried in a rack dryer (60° C.), and then granulated using PowerMILL to obtain granules. Together with the granules, 10 g of croscarmellose sodium (disintegrant sold under the trade name of Ac-Di-Sol, FMC International Inc.) and 1.5 g of sodium stearyl fumarate (lubricant, JRS Pharma LP) were mixed and molded with a tablet machine to obtain tablets with a total mass of 400 mg per tablet.

INDUSTRIAL APPLICABILITY

According to the present invention, there is provided a pharmaceutical composition and a kit that exhibit excellent anti-tumor effect. Specifically, the present invention provides a pharmaceutical composition and/or a kit comprising a compound represented by General Formula (I), a pharmacologically acceptable salt thereof or a solvate thereof in combination with an anti-tumor platinum complex, which can be used for the treatment of cancer.

The invention claimed is:

1. A pharmaceutical composition comprising a combination of:
    (i) 4-(3-chloro-4-(cyclopropylaminocarbonyl)aminophenoxy)-7-methoxy-6-quinolinecarboxamide, a pharmacologically acceptable salt thereof or a solvate thereof; and
    (ii) cisplatin or carboplatin.

2. The pharmaceutical composition according to claim 1, wherein the 4-(3-chloro-4-(cyclopropyloaminocarbonyl)aminophenoxy)-7-methoxy-6-quinolinecarboxamide, pharmacologically acceptable salt thereof or solvate thereof is a methanesulfonate of 4-(3-chloro-4-(cyclopropyloaminocarbonyl)aminophenoxy)-7-methoxy-6-quinolinecarboxamide.

3. A pharmaceutical composition comprising:
    4-(3-chloro-4-(cyclopropyloaminocarbonyl)aminophenoxy)-7-methoxy-6-quinolinecarboxamide, a pharmacologically acceptable salt thereof or a solvate thereof that is simultaneously or separately administered to a patient with an anti-tumor platinum complex selected from the group consisting of cisplatin or carboplatin.

4. The pharmaceutical composition according to claim 3, wherein the 4-(3-chloro-4-(cyclopropyloaminocarbonyl)aminophenoxy)-7-methoxy-6-quinolinecarboxamide, pharmacologically acceptable salt thereof or solvate thereof is a methanesulfonate of 4-(3-chloro-4-(cyclopropyloaminocarbonyl)aminophenoxy)-7-methoxy-6-quinolinecarboxamide.

5. A method for treating lung cancer characterized by simultaneously or separately administering, to a patient in need thereof, an effective amount of:
    (i) 4-(3-chloro-4-(cyclopropyloaminocarbonyl)aminophenoxy)-7-methoxy-6-quinolinecarboxamide, a pharmacologically acceptable salt thereof or a solvate thereof; and
    (ii) an anti-tumor platinum complex selected from the group consisting of cisplatin or carboplatin.

6. A method according to claim 5, wherein the 4-(3-chloro-4-(cyclopropyloaminocarbonyl)aminophenoxy)-7-methoxy-6-quinolinecarboxamide, pharmacologically acceptable salt thereof or solvate thereof is a methanesulfonate of 4-(3-chloro-4-(cyclopropyloaminocarbonyl)aminophenoxy)-7-methoxy-6-quinolinecarboxamide.

* * * * *

UNITED STATES PATENT AND TRADEMARK OFFICE
CERTIFICATE OF CORRECTION

| | |
|---|---|
| PATENT NO. | : 8,952,035 B2 |
| APPLICATION NO. | : 12/741682 |
| DATED | : February 10, 2015 |
| INVENTOR(S) | : Yuji Yamamoto |

It is certified that error appears in the above-identified patent and that said Letters Patent is hereby corrected as shown below:

<u>Title page, left column</u>

Insert item 60,

--Related U.S. Application Data

(60) Provisional application No. 60/986,641, filed on November 9, 2007--.

<u>In the claims</u>

<u>Column 24, claim 1</u>

Line 7, delete "cyclopropyloaminocarbonyl" and replace it with --cyclopropylaminocarbonyl--.

<u>Column 24, claim 2</u>

Line 13, delete "cyclopropyloaminocarbonyl" and replace it with --cyclopropylaminocarbonyl--.

Line 16, delete "cyclopropyloaminocarbonyl" and replace it with --cyclopropylaminocarbonyl--.

<u>Column 24, claim 3</u>

Line 19, delete "cyclopropyloaminocarbonyl" and replace it with --cyclopropylaminocarbonyl--.

<u>Column 24, claim 4</u>

Line 26, delete "cyclopropyloaminocarbonyl" and replace it with --cyclopropylaminocarbonyl--.

Line 29, delete "cyclopropyloaminocarbonyl" and replace it with --cyclopropylaminocarbonyl--.

<u>Column 24, claim 5</u>

Line 34, delete "cyclopropyloaminocarbonyl" and replace it with --cyclopropylaminocarbonyl--.

Signed and Sealed this
Fourth Day of August, 2015

Michelle K. Lee
*Director of the United States Patent and Trademark Office*

CERTIFICATE OF CORRECTION (continued)
U.S. Pat. No. 8,952,035 B2

Column 24, claim 6

Line 41, delete "cyclopropyloaminocarbonyl" and replace it with --cyclopropylaminocarbonyl--.

Line 44, delete "cyclopropyloaminocarbonyl" and replace it with --cyclopropylaminocarbonyl--.